US008389226B2

(12) United States Patent
Ray et al.

(10) Patent No.: US 8,389,226 B2
(45) Date of Patent: *Mar. 5, 2013

(54) METHODS AND COMPOSITIONS FOR DIAGNOSIS, STRATIFICATION, AND MONITORING OF ALZHEIMER'S DISEASE AND OTHER NEUROLOGICAL DISORDERS IN BODY FLUIDS

(76) Inventors: Sandip Ray, Spotswood, NJ (US); Anton Wyss-Coray, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/031,120

(22) Filed: Feb. 18, 2011

(65) Prior Publication Data

US 2011/0212854 A1    Sep. 1, 2011

Related U.S. Application Data

(63) Continuation of application No. 12/480,222, filed on Jun. 8, 2009, now abandoned, which is a continuation of application No. 11/148,595, filed on Jun. 8, 2005, now abandoned, which is a continuation-in-part of application No. 10/993,813, (Continued)

(51) Int. Cl.
*G01N 33/567* (2006.01)
*G01N 33/48* (2006.01)
*G01N 31/00* (2006.01)
*A61B 5/00* (2006.01)

(52) U.S. Cl. ............ 435/7.21; 702/19; 702/23; 600/300
(58) Field of Classification Search .................. None
See application file for complete search history.

(56) References Cited

U.S. PATENT DOCUMENTS

| | | | |
|---|---|---|---|
| 4,683,202 A | 7/1987 | Mullis | |
| 4,728,605 A | 3/1988 | Fudenberg et al. | |
| 5,874,312 A | 2/1999 | Sredni et al. | |
| 6,027,896 A | 2/2000 | Roses et al. | |
| 6,114,133 A | 9/2000 | Seubert et al. | |
| 6,130,048 A | 10/2000 | Nixon | |
| 6,183,971 B1 | 2/2001 | Sasada et al. | |
| 6,210,895 B1 | 4/2001 | Schipper et al. | |
| 6,251,639 B1 | 6/2001 | Kurn | |
| 6,358,681 B2 | 3/2002 | Ginsberg et al. | |
| 6,451,547 B1 | 9/2002 | Jackowski et al. | |
| 6,461,831 B1 | 10/2002 | Small et al. | |
| 6,465,195 B1 | 10/2002 | Holtzman et al. | |
| 6,475,161 B2 | 11/2002 | Teicher et al. | |
| 6,495,335 B2 | 12/2002 | Chojkier et al. | |
| 6,692,918 B2 | 2/2004 | Kurn | |
| 6,699,677 B1 | 3/2004 | Schall et al. | |
| 7,070,945 B2 | 7/2006 | Jackowski et al. | |
| 7,598,049 B2 * | 10/2009 | Ray et al. ............ | 435/7.21 |
| 7,608,406 B2 | 10/2009 | Valkirs et al. | |
| 2003/0119074 A1 | 6/2003 | Jackowski et al. | |
| 2006/0094064 A1 | 5/2006 | Ray et al. | |
| 2007/0037200 A1 | 2/2007 | Ray et al. | |

FOREIGN PATENT DOCUMENTS

| | | |
|---|---|---|
| EP | 1 050 758 | 11/2000 |
| WO | WO-02/44732 | 6/2002 |
| WO | WO-2005/052592 | 6/2005 |
| WO | WO-2006/133423 | 12/2006 |

OTHER PUBLICATIONS

Phillips et al., Neuron, 7:695-702, 1991.*
Masliah et al. Neurobiology of Aging, 16[4]:549-556, 1995.*
Carta et al., Psychother Psychosom, 71 [4]:233-236, 2002.*
Intebi et al., NeuroImmunoModulation, 10[6]:351-358, 2002-2003.*
Abraham, J.A. et al. (1986). "Human Basic Fibroblast Factor: Nucleotide Sequence and Genomic Organization," EMBO J. 5(10):2523-2528.
Agrawal, R. et al. (May 1993). "Mining Association Rules Between Sets of Items in Large Databases," Proc. of the 1993 ACM SIGMOD Conference on Management of Data, Washington, D.C., pp. 207-216.
Behan et al. (1970). "Serum Proteins, Amyloid and Alzheimer's Disease," Journal of the American Academy of Geriatrics Society, 18(10):792-797,1970.
Bertram, L. et al. (Jan. 2007). "Systematic Meta-analyses of Alzheimer Disease Genetic Association Studies: The AlzGene Database," Nature Genetics 39(1):17-23 + 76 supplemental pages.
Bimonte-Nelson, H.A. et al. (Jun. 2003). "Testosterone, but not Nonaromatizable Dihydrotestosterone, Improves Working Memory and Alters Nerve Growth Factor Levels in Aged Male Rats," Exp. Neurol. 181(2):301-312.
Blaber, S.I. et al. (Jan. 29, 2002). "Enzymatic Properties of Rat Myelencephalon-Specific Protease," Biochemistry 41(4):1165-1173.
Borroni, B. et al. (2006). "Predicting Alzheimer Dementia in Mild Cognitive Impairment Patients Are Biomarkers Useful?" European Journal of Pharmacology 545-73-80.
Brattstrom, D. (Jul. 2002). "Elevated Preoperative Serum Levels of Angiogenic Cytokines Correlate to Larger Primary Tumours and Poorer Survival in Non-Small Cell Lung Cancer Patients," Lung Cancer 37(1):57-63.
Burbach, G.J. et al. (Mar. 10, 2004). "Induction of Brain-Derived Neurotrophic Factor in Plaque-Associated Glial Cells of Aged APP23 Transgenic Mice," J. Neurosci. 24(1Q):2421-2430.
Capsoni, S. et al. (Jun. 6, 2000). "Alzheimer-Like Neurodegeneration in Aged Antinerve Growth Factor Transgenic Mice," Proc. Natl. Acad. Sci. U.S.A. 97(12):6826-6831.
Chan E., et al. Integrating Transcriptomics and Proteomics, Genomics and Proteomics, Apr. 1, 2006.

(Continued)

*Primary Examiner* — Daniel E Kolker
*Assistant Examiner* — Stacey N MacFarlane

(57) ABSTRACT

The inventors have discovered a collection of proteinaceous biomarkers ("AD biomarkers") which can be measured in peripheral biological fluid samples to aid in the diagnosis of neurodegenerative disorders, particularly Alzheimer's disease and mild cognitive impairment (MCI). The invention further provides methods of identifying candidate agents for the treatment of Alzheimer's disease by testing prospective agents for activity in modulating AD biomarker levels.

6 Claims, 4 Drawing Sheets

Related U.S. Application Data filed on Nov. 19, 2004, now Pat. No. 7,598,049.

(60) Provisional application No. 60/523,796, filed on Nov. 19, 2003, provisional application No. 60/566,783, filed on Apr. 30, 2004, provisional application No. 60/566,782, filed on Apr. 30, 2004.

(56) References Cited

OTHER PUBLICATIONS

Cheung, V. et al. (Mar. 2003), "Natural variation in human gene expression assessed in lumphoblastoid cells," Nature Genetics33:422-425.
Citron, M. et al. (Jan. 1997). "Mutant Presenitins of Alzheimer's Disease Increase Production of 42-Residue Amyloid B-Protein in Both Transfected Cells and Transgenic Mice," Nat. Med. 3(1):67-72.
Cobb et al. (2002). "Sepsis gene expression profiling: Murine splenic compared with hepatic responses determined by using complementary DNA microarrays," Crit Care Med. Dec. 2002;30(12):2711-21.
Collins, T. et al. (Aug. 22, 1985). "Cultured Human Endothelial Cells Express Platelet-Derived Growth Factor B Chain. cDNA Cloning and Structural Analysis," Nature 316(6030):748-750.
D'Ascenzo, M. et al. (Dec. 2005). "Alzheimer's Disease Cerebrospinal Fluid Biomarker Discovery: A Proteomics Approach," Curr. Opin. Mol. Ther. 7(6):557-564.
de Boer, L. et al. (2004). "Mutations in the NSD1 Gene in Patients with Soto s Syndrome Associate with Endocrine and Paracrine Alterations in the IGF System," European Journal of Endocrinology 151:333-341.
Docherty, A.J.P. et al. (Nov. 7, 1985). "Sequence of Human Tissue Inhibitor of Metalloproteinases and its Identity to Erythroid-Potentiating Activity," Nature 318(6041): 66-69.
Draghici, S. (2003). Data Analysis Tools for DNA Microarrays. Chapman & Hall/CRC, pp. 229, 247-248, and 295.
Ebadi, M. et al. (Apr.-May 1997). "Neurotrophins and Their Receptors in Nerve Injury and Repair," Neurochem. Int. 30(4-5):347-374.
Fahnestock, M. et al. (2002). "Neurotrophic Factors and Alzheimer's Disease: Are we Focusing on the Wrong Molecule?," J. Neural Transm. (62 Suppl.):241-252.
Fiala, M. et al. (Jul. 1998). "Amyloid-(3 Induces Chemokine Secretion and Monocyte Migration Across a Human Blood-Brain Barrier Model," Mol. Med. 4(7):480-489.
Folstein, M.F. et al. (1975). "'Mini-Mental State': A Practical Method for Grading the Cognitive State of Patients for the Clinician," J. Psychiat. Res. 12:189-198.
Foster, D.C. et al. (Dec. 1994). "Human Thrombopoietin: Gene Structure, cDNA Sequence, Expression, and Chromosomal Localization," Proc. Natl. Acad. Sci. USA. 91(26): 13023-13027.
Frank et al. (2003). "Biological markers for therapeutic trals in Alzheimer's disease Proceedings of the biological markers working group; NIA initiative on neuroimaging in Alzheimer's disease," Neurobiology of Aging, 24:521-536, 2003.
Frey, H.J. et al. (Dec. 2005), "Problems Associated with Biological Markers of Alzheimer's Disease," Neurochem. Res. 30(12):1501-1510.
Galasko, D. (Oct. 2001). "Biological Markers and the Treatment of Alzheimer's Disease," Journal of Molecular Neuroscience 17(2): 119-125.
Gasson, J.C. et al. (Jun. 27, 1985). "Molecular Characterization and Expression of the Gene Encoding Human Erythroid-Potentiating Activity," Nature 315 (6022): 768-771.
Gibbs, R.B. (Mar. 23, 1998). "Levels of trkA and BDNF mRNA, but not NGF mRNA, Fluctuate Across the Estrous Cycle and Increase in Response to Acute Hormone Replacement," Brain Res. 787(2):259-268.
Gibbs, R.B. (Nov. 9, 1998). "Levels of trkA and BDNF mRNA, but not NGF mRNA, Fluctuate Across the Estrous Cycle and Increase in Response to Acute Hormone Replacement," Erratum, Brain Res. 810(1-2): 294.
Gottardo, R. et al. (2003). "Statistical Analysis of Microarray Data: A Bayesian Approach," Biostatistics 4(4):597-620.
Gray, A. et al. (Jun. 23, 1983). "Nucleotide Sequence of Epidermal Growth Factor cDNA Predicts a 128,000-Molecular Weight Protein Precursor," Nature 303:722-725.
Gray, P.W. et al. (Dec. 20/27, 1984). "Cloning and Expression of cDNA for Human Lymphotoxin, a Lymphokine with Tumour Necrosis Activity," Nature 312(5996):721-724.
Hartbauer, M. et al. (2001). "Antiapoptotic Effects of the Peptidergic Drug Cerebrolysin on Primary Cultures of Embryonic Chick Cortical Neurons," J. Neural Transm. 108(4):459-473.
Hasegawa et al., (2000). "Increased Soluble Tumor Necrosis Factor Receptor Levels in the Serum of Elderly People" Gerontology, 46: 185-188, Jul./Aug. 2000.
Hastie, T. et al. (2001). "Supervised Harvesting of Expression Trees," Genome Biology 2(I):research0003.1-0003.12.
Heese, K. et al. (2000). "Induction of Rat L-Phosphoserine Phosphatase by Amyloid-13 (1-42) is Inhibited by Interleukin-11," Neurosci Lett. 288(1):37-40.
Hellweg, R. et al. (1994). "Neurotrophic Factors in Memory Disorders," Life Sci. 55(25-26):2165-2169.
Higgins, G.A. et al. (2003). "Transgenic Mouse Models of Alzheimer's Disease: Phenotype and Application," Behav. Pharmacol. 14(5-6):419-438.
Ho, L. et al. (Apr. 2005). "From Proteomics to Biomarker Discovery in Alzheimer's Disease," Brain Research Reviews 48:360-369.
Hohlfeld, R. et al. (2000). "The Neuroprotective Effect of Inflammation: Implications for the Therapy of Multiple Sclerosis," J. Neuroimmunol. 107:161-166.
Hohn, A. et al. (Mar. 22, 1990). "Identification and Characterization of a Novel Member of the Nerve Growth Factor/Brain-Derived Neurotrophic Factor Family," Nature 344(6264):339-341.
Hoshikawa, Y. et al. (2003). "Hypoxia Induces Different Genes in the Lungs of Rats Compared with Mice," Erratum—Corrigendum—Physiol. Genomics 13:79.
Hsieh, S.Y. et al. (May 2006). "Systematical Evaluation of the Effects of Sample Collection Procedures on Low-Molecular-Weight Serum/Plasma Proteome Profiling," Proteomics 6(10):3169-3198.
Huberman, M. et al. (1994). "Correlation of Cytokine Secretion by Mononuclear Cells of Alzheimer Patients and Their Disease Stage," J. Neuroimmunol. 52(2):147-152.
Intebi, A.D. et al. (2002-2003). "Alzheimer's Disease Patients Display Gender Dimorphism in Circulating Anorectic Adipokines," NeuroImmunoModulation 10(6):351-358.
International Search Report mailed Aug. 3, 2005 for PCT Application No. PCT/US2004/039275 filed Nov. 19, 2004, 3 pages.
Kim, S.H. et al. (Dec. 9, 2002). "Brain-Derived Neurotrophic Factor Can Act as a Pronecrotic Factor Through Transcriptional and Translational Activation of NADPH Oxidase," J. Cell Biol. 159(5): 821-31.
Kingham, PJ et al. (1999). "Apoptotic Pathways Mobilized in Microglia and Neurones as a Consequence of Chromogranin A-Induced Microglial Activation," J. Neurochem. 73(2):538-547.
Kohonen, T. (Jan. 1982). "Self-Organized Formation of Topologically Correct Feature Maps," Biological Cybernetics 43(1):59-69.
Kovacs, E. (Mar. 2001). "The Serum Levels of IL-12 and IL-16 in Cancer Patients. Relation to the Tumour Stage and Previous Therapy," Biomedicine & Pharmacotherapy 55(2):111-116.
Lakatos, P. et al. (May 2000). "Serum Insulin-Like Growth Factor-I, Insulin-Like Growth Factor Binding Proteins, and Bone Mineral Content in Hyperthyroidism," Thyroid 10(5):417-423.
Lang, U.E. et al. (Mar. 2, 2004; Dec. 29, 2003). "State of the Art of the Neurotrophin Hypothesis in Psychiatric Disorders: Implications and Limitations," J. Neural Transm. 111(3): 387-411.
Langenfeld, E.M. et al. (Sep. 2003). "The Mature Bone Morphogenetic Protein-2 is Aberrantly Expressed in Non-Small Cell Lung Carcinomas and Stimulates Tumor Growth of A549 Cells," Carcinogenesis 24(9):1445-1454.
Laske, C. et al. (2006). "Stage-Dependent BDNF Serum Concentrations in Alzheimer's Disease," J. Neural Transm. 113:1217-1224.
Lee, S.Y. et al. (May 2003, e-pub. Mar. 5, 2003). "1713-Estradiol Activates ICI 182,780-Sensitive Estrogen Receptors and Cyclic GMP-Dependent Thioredoxin Expression for Neuroprotection," FASEB J. 17(8):947-948.

Li, X.-L. et al. (Sep. 2, 2002). "Impairment of Long-term Potentiation and Spatial Memory in Leptin Receptor-Deficient Rodents," *Neuroscience* 113 (3): 607-615.

Lorigados, L. et al. (Jul. 1992). "Two-Site Enzyme Immunoassay for (3NGF Applied to Human Patient Sera," *J. Neurosci. Res.* 32(3):329339.

Marics, I. et al. (Mar. 1989). "Characterization of the HST-related *FGF* .6 Gene, a New Member of the Fibroblast Growth Factor Gene Family," *Oncogene* 4 (3 ):335-340.

Masliah, E. et al. (Jul./Aug. 1995). "PDGF is Associated with Neuronal and Glial Alterations of Alzheimer's Disease," *Neurobiol. Aging* 16(4):549-556.

Masuzaki, H. et al. (Jul. 1995). "Human *Obese* Gene Expression: Adipocyte-Specific Expression and Regional Differences in the Adipose Tissue," *Diabetes* 44(7):855-858.

Michalski, B. et al. (Mar. 17, 2003). "Pro-Brain-Derived Neurotrophic Factor is Decreased in Parietal Cortex in Alzheimer's Disease," *Mol. Brain Res.* 111(1-2):148-154.

Mohan, S. et al. (Aug. 1997). "Serum Insulin-Like Growth Factor Binding Protein (IGFBP)-4 and IGFBP-5 Levels in Aging and Age-Associated Diseases," *Endocrine* 7(1):87-91.

Mroczko, B. et al. (May 2001). "Granulocyte-Colony Stimulating Factor and Macrophage-Colony Stimulating Factor in Patients with Non-Small-Cell Lung Cancer," *Clin. Chem Lab. Med.* 39(5);374-379.

Murase, K.et al. (Jun. 1994). "Neurotrophin-3 (NT-3) Levels in the Developing Rat Nervous System and in Human Samples," *Clin. Chim. Acta* 227(1-2):23-36.

Nonaka, N et al. (Dec. 9, 2002). "Regional Differences in PACAP Transport Across the Blood-Brain Barrier in Mice: A Possible Influence of Strain, Amyloid (3 Protein, and Age," *Peptides* 23:2197-2202.

Oddo, S. et al. (Jul. 31, 2003). "Triple-Transgenic Model of Alzheimer's Disease with Plaques and Tangles: Intracellular A(3 and Synaptic Dysfunction," *Neuron* 39(3):409-421.

Olson, L. (Nov. 1993). "NGF and the Treatment of Alzheimer's Disease," *Exp. Neurol.* 124(1):5-15.

Pasinetti, G.M. et al. (2001). "From cDNA Microarrays to High-Throughput Proteomics. Implications in the Search for Preventive Initiatives to Slow the Clinical Progression of Alzheimer's Disease Dementia," *Restorative Neurology and Neuroscience* 18(2, 3):137142.

Patel, N.S. et al. (Mar. 11, 2005) "Inflammatory Cytokine Levels Correlate with Amyloid Load in Transgenic Mouse Models of Alzheimer's Disease," *J. Neuroinflammation* 2(1):9. (10 total pages).

Phillips, H.S. et al. (Nov. 1991). "BDNF mRNA Is Decreased in the Hippocampus of Individuals with Alzheimer's Disease," *Neuron* 7(5):695-702.

Ping, S.E. et al. (Jul. 1, 2002; e-pub. May 15, 2002). "Estrogen Treatment Suppresses Forebrain P75 Neurotrophin Receptor Expression in Aged, Noncycling Female Rats," *J. Neurosci. Res.* 69(1):5160.

Power, D.A. et al. (Mar.-Apr. 2001). "Circulating Leptin Levels and Weight Loss in Alzheimer's Disease Patients," *Dement. Geriatr. Cogn. Disord.* 12(2):167-170.

Qin, X. et al. (Sep. 4, 1998). "Structure-Function Analysis of the Human Insulin-Like Growth Factor Binding Protein-4," *The Journal of Biological Chemistry* 273 (36):23509-23516.

R&D Systems, Inc. (Jun. 18, 2003). "Quantikine® HS: Human G-CSF Immunoassay, Catalog No. HSCSO," located at http://archive.org/web/20030618210843/http://www.mdsystems.com/asp/csearch.asp?anyall=1&keywords=Quanitkine+HS, last visited on Mar. 16, 2005, 16 pages.

Ray, S. et al. (Manuscript submitted Sep. 26, 2006). "Early Alzheimer' s Disease Defined by Patterns of Cellular Communication Factors in Plasma," *Nature*, 17 pages.

Reiriz, J. et al. (Mar. 2002). "BMP-2 and cAMP Elevation Confer Locus Coeruleus Neurons Responsiveness to Multiple Neurotrophic Factors," *J. Neurobiol.* 50(4 ): 291-304.

Rikkert, M.G. et al. (Mar. 2003). "Geriatric Syndromes: Medical Misnomer or Progress in Geriatrics?," *Neth. J. Med.* 61(3):83-87.

Robakis, N.K. et al. (1991). "Expression of the Alzheimer's Amyloid Precursor in Brain Tissue and Effects of NGF and EGF on its Metabolism," *Clin. Neuropharmacol.* 14(Suppl. 1): S15-S23.

Roher A.E. et al. (Apr. 2000). "Cortical Cholinergic Denervation Elicits Vascular A13 Deposition," *Ann. N. Y. Acad. Sci.* 903:366-373.

Rosenthal, A. et al. (Sep. 1991). "Primary Structure and Biological Activity of Human Brain-Derived Neurotrophic Factor," *Endocrinology* 129(3 ): 1289-1294.

Sanna, V. et al. (Jan. 2003). "Leptin Surge Precedes Onset of Autoimmune Encephalomyelitis and Correlates with Development of Pathogenic T Cell Responses," *The Journal of Clinical Investigation* 111(2): 241-250.

Schall, T.J et al. (Apr. 20, 1990). "Molecular Cloning and Expression of a Receptor for Human Tumor Necrosis Factor," *Cell* 6I(2):36 1-370.

Schall, T.J. et al. (Aug. 1, 1988). "A Human T Cell-Specific Molecule is a Member of a New Gene Family," *I. Immunol.* 141(3):1018-1025.

Simpkins, J.W. et al. (Sep. 22, 1997). "Role of Estrogen Replacement Therapy in Memory Enhancement and the Prevention of Neuronal Loss Associated With Alzheimer's Disease," *Am. J. Med.* 103 (3 A): 19S-25S.

Singh, M. et al. (May 1995). "The Effect of Ovariectomy and Estradiol Replacement on Brain-Derived Neurotrophic Factor Messenger Ribonucleic Acid Expression in Cortical and Hippocampal Brain Regions of Female Sprague-Dawley Rats," *Endocrinology* 136(5):2320-2324.

Sjogren, M. et al. (2003). "Advances in the Detection of Alzheimer's Disease Useof Cerebrospinal Fluid Biomarkers," *Clinica Chimica Acta* 332(1-2): 1-10.

Stetler-Stevenson, W.G. et al. (Aug. 15, 1990). "Tissue Inhibitor of Metalloproteinases-2 (TIMP-2) mRNA Expression in Tumor Cell Lines and Human Tumor Tissues," *J. Biol. Chem.* 265(23):1393313938.

Taga, T. et al. (Aug. 11, 1989). "Interleukin-6 Triggers the Association of Its Receptor With a Possible Signal Transducer, gpI30," *Cell* 58(3):573-581.

Takahama et al Clin Cancer Res 1999, 5(9): 2506-10.

Tarkowski et al. "Local and systemic GM-CSF increase in Alzheimer's disease and vascular dementia," Acta Neurol Scand. 2001;103(3):166-74.

ten Dijke, P. et al. (Jul. 1988). "Identification of Another Member of the Transforming Growth Factor Type (3 Gene Family," *Proc. Natl. Acad. Sci. U.S.A.* 85(13):4715-4719.

Teunissen, C.E. et al. (2002). "Biochemical Markers Related to Alzheimer's Dementia in Serum and Cerebrospinal Fluid," *Neurobiol. Aging* 23:485-508.

Tham, A et al. (1993). "Insulin-Like Growth Factors and Insulin-Like Growth Factor Binding Proteins in Cerebrospinal Fluid and Serum of Patients with Dementia of the Alzheimer Type," *Journal of Neural Transmission* 5(3):165-176.

Thavasu, P.W. et al. (Aug. 30, 1992). "Measuring Cytokine Levels in Blood. Importance of Anticoagulants, Processing, and Storage Conditions," *J.Immunol. Methods* 153(1-20:115-124.

Tong, L. et al. (Jul. 28, 2004). "13-Amyloid Peptide at Sublethal Concentrations Downregulates Brain-Derived Neurotrophic Factor Functions in Cultured Cortical Neurons," *J. Neurosci.* 24(30):67996809.

Turner, R.S. (Sep. 2003). "Biomarkers of Alzheimer's Disease and Mild Cognitive Impairment: Are We There Yet?" *Experimental Neurology* 183(1):7-10.

Tusher, V.G. et al. (Apr. 24, 2001). "Significant Analysis of Microarrays Applied to the Ionizing Radiation Response," *Proc. Natl. Acad. Sci. USA.* 98(9):5116-5121.

Tuszynski, M.H. et al. (Apr. 1996). "Gene Therapy in the Adult Primate Brain: Intraparenchymal Grafts of Cells Genetically Modified to Produce Nerve Growth Factor Prevent Cholinergic Neuronal Degeneration," *Gene Ther.* 3 (4): 305-314.

Verdier, Y et al. (May 2004). "Amyloid 13-Peptide Interactions with Neuronal and Glial Cell Plasma Membrane: Binding Sites and Implications for Alzheimer's Disease," *J. Pept. Sci.* 10(5):229-248.

Verdier, Y. et al. (2004). "Binding Sites of Amyloid 13-Peptide in Cell Plasma Membrane and Implications for Alzheimer's Disease," *Curr. Protein Pept. Sci.* 5(1): 19-31.

Wang, W. et al. (May 1998). "Molecular Cloning and Functional Characterization of Human MIP-16, a New C-C Chemokine Related to Mouse CCF-18 and C10," *J. Clin. Immunol.* 18(3):214-222.

Windisch, M. et al. (1998). "Neurotrophic Activities and Therapeutic Experience with a Brain Derived Peptide Preparation," *J. Neural Transm. Suppl.* 53:289-298.

Wirdefeldt, K. et al. (Jul. 26, 2003). "A Linkage Study of Candidate Loci in Familial Parkinson's Disease," BMC Neurol. 3, seven pages.

Xia, M. et al. (Jul. 1998). "Immunohistochemical Study of the 13-Chemokine Receptors CCR3 and CCR5 and Their Ligands in Normal and Alzheimer's Disease Brains," *Am. J. Pathol.* 153(1):3137.

Yang, Y.C. et al. (Oct. 10, 1986). "Human IL-3 (Multi-CSF): Identification by Expression Cloning of a Novel Hematopoietic Growth Factor Related to Murine IL-3," Cell 47(1):3-10.

Yoshikawa, W. et al. (Mar. 15, 1999). "Characterization of Free a-and (3-Chains of Recombinant Macrophage-Stimulating Protein," *Arch. Biochem. Biophys.* 363(2):356-360.

Yoshimura, T. et al. (Jul. 25, 1993). "Cloning, Sequencing, and Expression of Human Macrophage Stimulating Protein (MSP, MST I) Confirms MSP as a Member of the Family of Kringle Proteins and Locates the MSP Gene on Chromosome 3," *J. Biol. Chem.* 268(21):15461-15468.

Zsebo, K.M. et al. (Oct. 5, 1990). "Stem Cell Factor is Encoded at the S/Locus of the Mouse and is the Ligand for the c-kit Tyrosine Kinase Receptor," *Cell* 63 (I): 213-224.

Errahali et al., J Interferon Cytokine Res. 29(4), Apr. 2009 [abstract only].

Ray et al., Nature medicine 13(11): 1359-1362, epublished on Oct. 14, 2007.

\* cited by examiner

METHODS AND COMPOSITIONS FOR DIAGNOSIS, STRATIFICATION, AND MONITORING OF ALZHEIMER'S DISEASE AND OTHER NEUROLOGICAL DISORDERS IN BODY FLUIDS

CROSS-REFERENCE TO RELATED APPLICATIONS

This application is a continuation application of U.S. Patent application Ser. No. 12/480,222, filed Jun. 8, 2009, which is a continuation application of U.S. Patent application Ser. No. 11/148,595, filed Jun. 8, 2005, which is a continuation in part application of U. S. patent application Ser. No. 10/993,813, filed Nov. 19, 2004 which claims benefit of U.S. Provisional Patent Application No. 60/523,796, filed Nov. 19, 2003, U.S. Provisional Patent Application Serial No. 60/566,783, filed Apr. 30, 2004, and U.S. Provisional Patent Application No. 60/566,782, filed Apr. 30, 2004, all of which are incorporated by reference herein in their entireties.

STATEMENT REGARDING FEDERALLY SPONSORED RESEARCH OR DEVELOPMENT

Not applicable.

REFERENCE TO A COMPACT DISK APPENDIX

Not applicable

BACKGROUND OF THE INVENTION

An estimated 4.5 million Americans have Alzheimer's Disease ("AD"). By 2050, the estimated range of AD prevalence will be 11.3 million to 16 million. Currently, the societal cost of AD to the U.S. is $100 billion per year, including $61 billion borne by U.S. businesses. Neither Medicare nor most private health insurance covers the long-term care most patients need.

Alzheimer's Disease is a neurodegenerative disease of the central nervous system associated with progressive memory loss resulting in dementia. Two pathological characteristics are observed in AD patients at autopsy: extracellular plaques and intracellular tangles in the hippocampus, cerebral cortex, and other areas of the brain essential for cognitive function. Plaques are formed mostly from the deposition of amyloid beta ("A$\beta$"), a peptide derived from amyloid precursor protein ("APP"). Filamentous tangles are formed from paired helical filaments composed of neurofilament and hyperphosphorylated tau protein, a microtubule-associated protein. It is not clear, however, whether these two pathological changes are only associated with the disease or truly involved in the degenerative process. Late-onset/sporadic AD has virtually identical pathology to inherited early-onset/familial AD (FAD), thus suggesting common pathogenic pathways for both forms of AD. To date, genetic studies have identified three genes that cause autosomal dominant, early-onset AD, amyloid precursor protein ("APP"), presenilin 1 ("PS1"), and presenilin 2 ("PS2"). A fourth gene, apolipoprotein E ("ApoE"), is the strongest and most common genetic risk factor for AD, but does not necessarily cause it. All mutations associated with APP and PS proteins can lead to an increase in the production of A$\beta$ peptides, specifically the more amyloidogenic form, A$\beta_{42}$. In addition to genetic influences on amyloid plaque and intracellular tangle formation, environmental factors (e.g., cytokines, neurotoxins, etc.) may also play important roles in the development and progression of AD.

The main clinical feature of AD is a progressive cognitive decline leading to memory loss. The memory dysfunction involves impairment of learning new information which is often characterized as short-term memory loss. In the early (mild) and moderate stages of the illness, recall of remote well-learned material may appear to be preserved, but new information cannot be adequately incorporated into memory. Disorientation to time is closely related to memory disturbance.

Language impairments are also a prominent part of AD. These are often manifest first as word finding difficulty in spontaneous speech. The language of the AD patient is often vague, lacking in specifics and may have increased automatic phrases and clichës. Difficulty in naming everyday objects is often prominent. Complex deficits in visual function are present in many AD patients, as are other focal cognitive deficits such as apraxia, acalculia and left-right disorientation. Impairments of judgment and problems solving are frequently seen.

Non-cognitive or behavioral symptoms are also common in AD and may account for an event larger proportion of caregiver burden or stress than the cognitive dysfunction. Personality changes are commonly reported and range from progressive passivity to marked agitation. Patients may exhibit changes such as decreased expressions of affection. Depressive symptoms are present in up to 40%. A similar rate for anxiety has also been recognized. Psychosis occurs in 25%. In some cases, personality changes may predate cognitive abnormality.

Currently, the primary method of diagnosing AD in living patients involves taking detailed patient histories, administering memory and psychological tests, and ruling out other explanations for memory loss, including temporary (e.g., depression or vitamin $B_{12}$ deficiency) or permanent (e.g., stroke) conditions. These clinical diagnostic methods, however, are not foolproof.

One obstacle to diagnosis is pinpointing the type of dementia; AD is only one of seventy conditions that produce dementia. Because of this, AD cannot be diagnosed with complete accuracy until after death, when autopsy reveals the disease's characteristic amyloid plaques and neurofibrillary tangles in a patient's brain. In addition, clinical diagnostic procedures are only helpful after patients have begun displaying significant, abnormal memory loss or personality changes. By then, a patient has likely had AD for years.

Given the magnitude of the public health problem posed by AD, considerable research efforts have been undertaken to elucidate the etiology of AD as well as to identify biomarkers (secreted proteins or metabolites) that can be used to diagnose and/or predict whether a person is likely to develop AD. Because AD the CNS is relatively isolated from the other organs and systems of the body, most research (in regards to both disease etiology and biomarkers) has focused on events, gene expression, biomarkers, etc. within the central nervous system. With regards to biomarkers, the proteins amyloid beta and tau are probably the most well characterized. Research has shown that cerebrospinal fluid ("CSF") samples from AD patients contain higher than normal amounts of tau, which is released as neurons degenerate, and lower than normal amounts of beta amyloid, presumably because it is trapped in the brain in the form of amyloid plaques. Because these biomarkers are released into CSF, a lumbar puncture (or "spinal tap") is required to obtain a sample for testing.

A number of U.S. patents have been issued relating to methods for diagnosing AD, including U.S. Pat. Nos. 4,728, 605, 5,874,312, 6,027,896, 6,114,133, 6,130,048, 6,210,895, 6,358,681, 6,451,547, 6,461,831, 6,465,195, 6,475,161, and 6,495,335. Additionally, a number of reports in the scientific literature relate to certain biochemical markers and their correlation/association with AD, including Fahnestock et al., 2002, *J. Neural. Transm. Suppl.* 2002(62):241-52; Masliah et al., 1195, *Neurobiol. Aging* 16(4):549-56; Power et al., 2001, *Dement. Geriatr. Cogn. Disord.* 12(2):167-70; and Burbach et al., 2004, *J. Neurosci.* 24(10):2421-30. Additionally, Li et al. (2002, *Neuroscience* 113(3):607-15) and Sanna et al. (2003, J. Clin. Invest. 111(2):241-50) have investigated Leptin in relation to memory and multiple sclerosis, respectively.

All patents and publications cited herein are incorporated by reference in their entirety.

BRIEF SUMMARY OF THE INVENTION

The inventors have discovered a collection of biochemical markers, present in the blood of individuals, including from the serum or plasma of individuals, which are altered in individuals with Alzheimer's Disease ("AD"). Accordingly, these biomarkers ("AD diagnosis biomarkers") may be used to assess cognitive function, to diagnose or aid in the diagnosis of AD and/or to measure progression of AD in AD patients. AD diagnosis markers may be used individually or in combination for diagnosing or aiding in the diagnosis of AD. The invention provides methods for the diagnosis of AD or aiding the diagnosis of AD in an individual by measuring the amount of one or more AD diagnosis biomarkers in a biological fluid sample, such as a peripheral biological fluid sample from the individual and comparing the measured amount with a reference value for each AD diagnosis biomarker measured. The information thus obtained may be used to aid in the diagnosis or to diagnose AD in the individual. Accordingly, the present invention provides a method of aiding diagnosis of Alzheimer's disease ("AD"), comprising comparing a measured level of at least one AD diagnosis biomarker in a biological fluid sample from an individual to a reference level for the biomarker, wherein the AD diagnosis biomarker is selected from the group consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In some examples, the AD diagnosis biomarker is selected from the group consisting of basic fibroblast growth factor (bFGF); BB homodimeric platelet derived growth factor (PDGF-BB); brain derived neurotrophic factor (BDNF); epidermal growth factor (EGF), fibroblast growth factor 6 (FGF-6), interleukin-3 (IL-3), soluble interleukin-6 receptor (sIL-6R), leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-(33), and tumor necrosis factor beta (TNF-β). In other examples, the AD diagnosis marker is selected from the group consisting of BDNF, sIL-6R, IL-8, leptin, MIP-1δ, PDGF-BB, and TIMP-1. In yet other examples, the AD diagnosis marker is selected from the group consisting of sIL-6R, IL-8, and TIMP-1. In further examples, the AD diagnosis marker is selected from the group consisting of BDNF, MIP-1δ, and TIMP-1. In additional examples, the AD diagnosis marker is selected from the group consisting of BDNF, PDGF-BB, leptin and RANTES. In additional examples, the AD diagnosis marker comprises BDNF, PDGF-BB, leptin and RANTES. In additional examples, the method comprises comparing the measuring level of at least two AD diagnosis biomarkers to a reference level for the biomarkers. In additional examples, the method comprises comparing the measuring level of at least three AD diagnosis biomarkers to a reference level for the biomarkers. In further examples, the method comprises comparing the measuring level of at least four AD diagnosis biomarkers to a reference level for the biomarkers. In additional examples, comparing the measured level to a reference level for each AD diagnosis biomarker measured comprises calculating the fold difference between the measured level and the reference level. In some examples, a method further comprises comparing the fold difference for each AD diagnosis biomarker measured with a minimum fold difference level. In some examples, the method further comprises the step of obtaining a value for the comparison of the measured level to the reference level. Provided herein are computer readable formats comprising the values obtained by the method as described herein.

Provided herein are methods of aiding diagnosis of Alzheimer's disease ("AD"), comprising comparing a measured level of at least four AD diagnosis biomarkers, wherein said biomarkers comprise BDNF, PDGF-BB, leptin and RANTES, in a biological fluid sample from an individual to a reference level for each AD diagnosis biomarker. In some examples, AD is diagnosed when BDNF is decreased at least about 20% as compared to a reference level of BDNF. In other examples, AD is diagnosed when Leptin is decreased at least about 25% as compared to a reference level of Leptin. In additional examples, AD is diagnosed when RANTES is decreased at least about 16% as compared to a reference level of RANTES. In further examples, severe AD is diagnosed when PDGF-BB is decreased at least about 85% as compared to a reference level of PDGF-BB. In yet further examples, the biological fluid sample is a peripheral biological fluid sample.

Provided herein are methods for monitoring progression of Alzheimer's disease (AD) in an AD patient, comprising: comparing a measured level of at least one AD diagnosis biomarker in a biological fluid sample from an individual to a reference level for the biomarker, wherein the AD diagnosis biomarker is selected from the group consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In some examples, the AD diagnosis biomarker is selected from the group consisting of basic fibroblast growth factor (bFGF); BB homodimeric platelet derived growth factor (PDGF-BB); brain derived neurotrophic factor (BDNF); epidermal growth factor (EGF), fibroblast growth factor 6 (FGF-6), interleukin-3 (IL-3), soluble interleukin-6 receptor (sIL-6R), leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), and tumor necrosis factor beta (TNF-β). In other examples, the AD diagnosis marker is selected from the group consisting of BDNF, PDGF-BB, leptin and RANTES.

The inventors have also discovered methods of identifying individuals with mild cognitive deficit (MCI), a clinically recognized disorder considered distinct from AD in which cognition and memory are mildly deficient. The inventors have found that the biomarker RANTES is decreased in individuals with MCI. Individuals with MCI can be distinguished from those with AD by measuring biomarkers which are reduced in AD patients, but not those individuals with MCI (e.g., Leptin). Accordingly, the invention provides methods for diagnosing or aiding in the diagnosis of MCI by obtaining a measured value for the level of RANTES in a peripheral biological fluid sample and comparing that measured value against a reference value. In certain embodiments, such methods include obtaining a measuring value for Leptin levels in the peripheral biological fluid sample and comparing that measured level against a reference value. The information thus obtained may be used to aid in the diagnosis or to diagnose MCI in the individual.

Further, the inventors have discovered methods of stratifying AD patients (i.e., sorting individuals with a probable diagnosis of AD or diagnosed with AD into different classes of AD) by obtaining measured values for brain derived neurotrophic factor (BDNF) and BB-homodimer platelet derived growth factor (PDGF-BB) levels in a peripheral biological fluid sample from an AD patient. The measured levels of these two biomarkers are compared with reference values. The information thus obtained may be used to aid in stratification of the AD diagnosis (or probable AD diagnosis) of the individual. Accordingly, the present invention provides methods for stratifying Alzheimer's disease (AD) in an individual, comprising comparing measured values for brain derived neurotrophic factor (BDNF) and BB homodimeric platelet derived growth factor (PDGF-BB) levels in a biological fluid sample from said patient with reference values for BDNF and PDGF-BB. In some examples, the biological fluid sample is a peripheral fluid sample, including blood, serum or plasma. In other examples, the method further comprises comparing measured values for leptin and Rantes levels with reference values for leptin and Rantes, wherein reference values for BDNF, PDGF-BB, leptin and Rantes are for samples from individuals with MMSE scores from 25 to 28, wherein an increase in leptin and PDGF-BB levels and wherein levels of BDNF and RANTES stay substantially the same indicate mild AD as indicated by an MMSE score of 20-25. In additional examples, the method further comprises comparing measured values for leptin and Rantes levels with reference values for leptin and Rantes, wherein reference values for BDNF, PDGF-BB, leptin and Rantes are for samples from individuals with MMSE scores from 20-25, wherein a decrease in Rantes, BDNF, and PDGF levels and wherein levels of Leptin stays substantially the same indicate moderate AD as indicated by an MMSE score of 10-20.

In one aspect, the invention provides methods of aiding in the diagnosis of Alzheimer's disease ("AD") by obtaining a measured level of at least one AD diagnosis biomarker in a peripheral biological fluid sample from an individual, where the AD diagnosis biomarker is from the group consisting of basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), and tumor necrosis factor beta (TNF-β), and comparing the measured level to the reference level. In some embodiments, measured levels are obtained for at least two, three, four, or five AD diagnosis biomarkers. In some embodiments, the comparison of the measured value and the reference value includes calculating a fold difference between the measured value and the reference value. In some embodiments the measured value is obtained by measuring the level of the AD diagnosis biomarker(s) in the sample, while in other embodiments the measured value is obtained from a third party. Also provided are methods of aiding in the diagnosis of Alzheimer's disease ("AD") by comparing a measured level of at least one AD diagnosis biomarker in a peripheral biological fluid sample from an individual with a reference level. Further provided are methods of aiding in the diagnosis of Alzheimer's disease ("AD") by measuring a level of at least one AD diagnosis biomarker in a peripheral biological fluid sample from an individual, wherein a decrease as compared to a reference level suggests a diagnosis of AD.

In another aspect, the invention provides methods for aiding in the diagnosis of mild cognitive impairment (MCI) by obtaining a measured level for RANTES in a peripheral biological fluid sample from an individual, and comparing the measured level to a reference level. In some embodiments, the method for aiding in the diagnosis of MCI also includes obtaining a measured value for Leptin in the peripheral biological fluid sample and comparing measured value for Leptin to a reference level. In certain embodiments, the measured value is obtained by measuring the level of RANTES (and/or Leptin) in the sample, while in other embodiments, the measured value(s) is obtained from a third party. Also provided are methods of aiding in the diagnosis of mild cognitive impairment (MCI) by comparing a measured level for RANTES, and optionally Leptin, in a peripheral biological fluid sample from an individual with a reference level. Further provided are methods for aiding in the diagnosis of MCI by measuring a level for RANTES, and optionally Leptin, in a peripheral biological fluid sample from an individual, wherein a reduction in the RANTES level as compared to a reference level suggests a diagnosis of MCI (in embodiments in which Leptin in measured, a Leptin level that is equal to or greater than the reference level also suggests MCI).

In a further aspect, the invention provides methods for monitoring progression of Alzheimer's disease (AD) in an AD patient by obtaining a measured value for Leptin in a peripheral biological fluid sample; and comparing said measured value for Leptin with a reference value. In certain embodiments, the measured value is obtained by measuring the level of Leptin in the sample to produce, while in other embodiments, the measured value is obtained from a third party. Also provided are methods for monitoring progression of AD in an AD patient by comparing a measured value for Leptin in a peripheral biological fluid sample with a reference value. Further provided are methods for monitoring progression of AD in an AD patient by measuring a level for Leptin in a peripheral biological fluid sample, wherein a decrease in Leptin as compared with a reference value suggests progression (increased severity) of the AD. In some examples, the invention provides methods for monitoring progression of Alzheimer's disease (AD) in an AD patient by obtaining a measured value for Lymphotactin and/or IL-11 in a peripheral biological fluid sample; and comparing said measured value for Leptin with a reference value.

In another aspect, the invention provides methods for stratifying AD in an AD patient. In some embodiments, stratification between mild and more advanced AD is carried out by obtaining a measured value for brain derived neurotrophic factor (BDNF) levels in a peripheral biological fluid sample from an AD patient, and comparing the measured value with reference values for BDNF. In other embodiments, stratification between mild, moderate, and severe AD is carried out by obtaining levels for BDNF and BB homodimeric platelet derived growth factor (PDGF-BB), and comparing the measured levels with reference levels for BDNF and PDGF-BB. In certain embodiments, the measured value is obtained by measuring the level(s) of BDNF (and PDGF-BB) in the sample to produce the measured value(s), while in other embodiments, the measured value(s) is obtained from a third party. Also provided are methods for stratifying AD in an AD patient by comparing a BDNF (and, optionally, PDGF-BB) level in a peripheral biological fluid sample from an AD patient with a reference value for BDNF (and PDGF-BB when appropriate). Further provided are methods for stratifying AD in an AD patient by measuring a BDNF level (and, optionally, a PDGF-BB level) in a peripheral biological fluid sample, wherein a low level of BDNF (as compared to a reference value) suggests mild AD, a high level of BDNF (as compared to a reference value) suggests more advanced AD, a high level of BDNF and a low level of PDGF-BB (as compared to reference values) suggests moderate AD, and a high level of BDNF and a high level of PDGF-BB (as compared to reference values) suggests severe AD. In another aspect, the invention provides methods for stratifying AD in an AD patient. In some examples, stratification between mild and more advanced AD is carried out by obtaining a measured value for Lymphotactin and/or IL-11 levels in a peripheral biological fluid sample from an AD patient, and comparing the measured value with reference value for Lymphotactin and/or IL-11.

In some embodiments, the peripheral biological fluid sample is a blood sample. In certain embodiments the peripheral biological fluid sample is a plasma sample. In other embodiments, the peripheral biological fluid sample is a serum sample.

In yet another aspect, the invention provides methods of identifying candidate agents for treatment of Alzheimer's Disease by assaying a prospective candidate agent for activity in modulating an AD biomarker, where the AD biomarker is from the group consisting of basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF R11), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β). Provided herein are methods of identifying a candidate agent for treatment of Alzheimer's Disease, comprising: assaying a prospective candidate agent for activity in modulating an AD biomarker, said AD biomarker selected from the group consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In some examples, the AD biomarkers are selected from the group consisting of BDNF, PDGF-BB, Leptin and RANTES.

In a further aspect, the invention provides kits for diagnosing Alzheimer's disease (AD) including at least one reagent specific for an AD diagnosis marker, where the AD diagnosis biomarker is from the group consisting of basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β), and instructions for carrying out a method of aiding in the diagnosis of AD described herein. Provided herein are kits for use in the methods as disclosed herein, comprising at least one reagent specific for at least one AD diagnosis marker, said at least one AD diagnosis biomarker selected from the group consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R and instructions for carrying out methods provided herein. Additionally, provided herein are sets of reference values for AD diagnosis biomarkers comprising BDNF, PDGF-BB, Leptin and RANTES and set of reagents specific for AD diagnosis biomarkers, wherein said biomarkers comprise BDNF, PDGF-BB, Leptin and RANTES.

In another aspect, the invention provides kits for identifying individuals with mild cognitive impairment (MCI) including at least one reagent specific for RANTES; and instructions for carrying out method of aiding in the diagnosis of MCI described herein. In certain embodiments, kits for identifying individuals with MCI may also include a reagent specific for Leptin.

In yet another aspect, the invention provides kits for monitoring progression of Alzheimer's disease (AD) in AD patients including at least one reagent specific for Leptin; and instructions for carrying out a method of monitoring AD progression described herein.

In a further aspect, the invention provides kits for stratifying an Alzheimer's disease (AD) patients including at least one reagent specific for brain derived neurotrophic factor (BDNF), at least one reagent specific for BB homodimeric platelet derived growth factor (PDGF-BB), and instructions for carrying out a method of stratifying an AD patient described herein. In yet further examples, kits for use in the methods as described herein, comprise AD diagnosis markers are selected from the group consisting of BDNF, PDGF-BB, leptin and RANTES. In further examples of kits for use in the methods as disclosed herein, the reagent specific for the AD diagnosis biomarker is an antibody, or fragment thereof, that is specific for said AD diagnosis biomarker. In further examples kits for use in the methods disclosed herein further comprise at least one reagent specific for a biomarker that measures sample characteristics.

Provided herein are surfaces comprising attached thereto, at least one reagent specific for each AD diagnosis biomarker in a set of AD diagnosis biomarkers, wherein said set of AD diagnosis biomarkers comprises BDNF, PDGF-BB, leptin and RANTES. Provided herein are surfaces comprising attached thereto, at least one reagent specific for each AD diagnosis biomarker in a set of AD diagnosis biomarkers, wherein said set of AD diagnosis biomarkers consists of BDNF, PDGF-BB, leptin and RANTES; and at least one reagent specific for a biomarker that measures sample characteristics. In further examples, provided herein are surfaces wherein said reagent specific for said AD diagnosis biomarker is an antibody, or fragment thereof, that is specific for said AD diagnosis biomarker.

Provided herein are combinations comprising the surfaces as described herein having attached thereto at least one reagent specific for each AD diagnosis biomarker and a peripheral biological fluid sample from an individual. In some examples, the individual is at least 60, 65, 70, 75, 80, or 85 years of age.

Provided herein are methods for obtaining values for the comparison of the measured level to the reference level of biological fluid samples. The present invention provides computer readable formats comprising the values obtained by the methods described herein.

Provided herein are methods of aiding diagnosis of Alzheimer's disease ("AD"), comprising comparing a measured level of at least one AD diagnosis biomarker selected from the group consisting of the biomarkers listed in Tables 9A1-9A2 and 9B in a biological fluid sample from an individual to a reference level for each AD diagnosis biomarker. In some examples, provided herein are methods of aiding diagnosis of Alzheimer's disease ("AD"), comprising comparing a measured level of at least one AD diagnosis biomarker in a biological fluid sample from an individual to a reference level for the biomarker, wherein the AD diagnosis biomarker is selected from the group consisting of BTC; SDF-1; MCP-2; IFN-gamma; IGFBP-4; IGF-1SR; IL-8; GM-CSF; and ANG-2. In some examples, provided herein are methods that comprise comparing a measured level of at least two, three, four or five AD diagnosis biomarker in a biological fluid sample from an individual to a reference level for the biomarker, wherein the AD diagnosis biomarker is selected from the group consisting of BTC; SDF-1; MCP-2; IFN-gamma; IGFBP-4; IGF-1SR; IL-8; GM-CSF; and ANG-2. In some examples, the at least one AD diagnosis biomarker is selected from the group consisting of biomarkers IFN-gamma and IL-8. In other examples, provided herein are methods of aiding diagnosis of Alzheimer's disease ("AD"), comprising comparing a measured level of at least one AD diagnosis biomarker in a biological fluid sample from an individual to a reference level for the biomarker, wherein the AD diagnosis biomarker is selected from the group consisting of sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and FGF-6. Provided herein are methods of aiding diagnosis of Alzheimer's disease ("AD"), comprising comparing a measured level of at least one AD diagnosis biomarker in a biological fluid sample from an individual to a reference level for the biomarker, wherein the AD diagnosis biomarker is selected from the group consisting of lymphotactin and IL-11. In some examples, the biological fluid sample is a peripheral biological fluid sample. In additional examples, the biological fluid sample is plasma. Provided herein are methods of aiding diagnosis of a neurodegenerative disease comprising obtaining measured values of one or more biomarkers shown in Table 12A-12B with a q-value % of less than 1.5, and comparing the measured value to a reference value.

Provided herein are methods for monitoring progression of Alzheimer's disease (AD) in an AD patient, comprising comparing a measured level of at least one AD diagnosis biomarker in a biological fluid sample from an individual to a reference level for the biomarker, wherein the AD diagnosis biomarker is selected from the group consisting of the biomarkers listed in Tables 9A1-9A2 and 9B. In some examples, the reference level is a level obtained from a biological fluid sample from the same AD patient at an earlier point in time. In other examples, the biological fluid sample is a peripheral biological fluid sample. In yet additional examples, the biological fluid sample is plasma. In further examples, the at least one AD diagnosis biomarker is selected from the group consisting of BTC; SDF-1; MCP-2; IFN-gamma; IGFBP-4; IGF-1SR; IL-8; GM-CSF; and ANG-2. In additional examples, the at least one AD diagnosis biomarker is selected from the group consisting of IFN-gamma and IL-8. In further examples, the at least one AD diagnosis biomarker is selected from the group consisting of biomarkers sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and FGF-6. In additional examples, provided herein are methods for monitoring progression of Alzheimer's disease (AD) in an AD patient, comprising, comparing a measured level of at least one AD diagnosis biomarker in a biological fluid sample from an individual to a reference level for the biomarker, wherein the AD diagnosis biomarker is selected from the group consisting of lymphotactin and IL-11.

Provided herein are methods for stratifying Alzheimer's disease (AD) in an individual, comprising, comparing measured levels for at least one biomarker in a biological fluid sample from an individual to a reference level for the biomarker, wherein the AD diagnosis biomarker is selected from the group consisting of lymphotactin and IL-11. In some examples, the biological fluid sample is a peripheral fluid sample. In other examples, the biological fluid sample is plasma.

Provided herein are methods of identifying a candidate agent(s) for treatment of Alzheimer's Disease, comprising: assaying a prospective candidate agent for activity in modulating at least one AD diagnosis biomarker in a biological fluid sample from an individual, wherein the AD diagnosis biomarker is selected from the group consisting of the biomarkers listed in Tables 9A1-9A2 and 9B. In some examples, the at least one AD diagnosis biomarker is selected from the group consisting of biomarkers BTC; SDF-1; MCP-2; IFN-gamma; IGFBP-4; IGF-1SR; IL-8; GM-CSF; and ANG-2. In other examples, the at least one AD diagnosis biomarker is selected from the group consisting of biomarkers IFN-gamma and IL-8. In further examples, the at least one AD diagnosis biomarker is selected from the group consisting of biomarkers sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and FGF-6. In additional examples, the at least one AD diagnosis biomarker is selected from the group consisting of biomarkers lymphotactin and IL-11. In some examples, the assay is performed in vivo.

In additional examples, provided herein are kits for use in the methods as described herein, such as for example, aiding in the diagnosis of AD or diagnosing AD comprising, at least one reagent specific for at least one AD diagnosis marker, wherein said at least one AD diagnosis biomarker is selected from the group consisting of the biomarkers listed in Tables 9A1-9A2 and 9B, and instructions for carrying out the method, such as for example, aiding in the diagnosis of AD or diagnosing AD. In some examples of kits as described herein, the at least one AD diagnosis biomarker is selected from the group consisting of BTC; SDF-1; MCP-2; IFN-gamma; IGFBP-4; IGF-1SR; IL-8; GM-CSF; and ANG-2. In other examples, the at least one AD diagnosis biomarker is selected from the group consisting of IFN-gamma and IL-8. In further examples, the at least one AD diagnosis biomarker is selected from the group consisting of sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and FGF-6. In further examples, the at least one AD diagnosis biomarker is selected from the group consisting of lymphotactin and IL-11. In further examples, a kit comprises at least one reagent specific for each of at least two AD diagnosis markers; at least one reagent specific for each of at least three AD diagnosis markers; at least one reagent specific for each of at least four AD diagnosis markers, or at least one reagent specific for each of at least five AD diagnosis markers. In further examples, the reagent specific for the AD diagnosis biomarker is an antibody, or fragment thereof, that is specific for said AD diagnosis biomarker. In further examples, the kit detects common variants of the biomarkers listed in Tables 9A1-9A2 and 9B, wherein a common variant indicates a protein that is expressed in at least 5 or more of the population in industrialized nations. In further examples, a kit for use in the methods disclosed herein further comprises a biomarker for normalizing data. In some examples, the biomarker for normalizing data is selected from the group consisting of TGF-beta and TGF-beta3.

Provided herein are surfaces comprising attached thereto, at least one reagent specific for an AD diagnosis biomarker selected from the group consisting of the biomarkers listed in Table 7, wherein the AD diagnosis marker is characterized by the following criteria: Correlation: greater than 90% (r=0.9 to r=0.99) with the biomarker clusters 0-8 listed in Tables 9A1-9A2 and 9B; P-value less than 0.001 up to 0.05; Fold change greater than 20%; and a Score greater than 1 (for markers that increase) or less than 1 (for markers that decrease). Provided herein are combinations comprising a surface and a peripheral biological fluid sample from an individual. In some examples, the individual is at least 60, 65, 70, 75, 80, or 85.

Provided herein are methods for identifying at least one biomarker useful for the diagnosis of a neurological disease, comprising, obtaining measured values from a set of peripheral biological fluid samples for a plurality of biomarkers, wherein said set of peripheral biological fluid samples is divisible into subsets on the basis of a neurological disease; comparing the measured values from each subset for at least one biomarker; and identifying at least one biomarker for which the measured values are significantly different between the subsets. In some examples, neurological disease is AD.

BRIEF DESCRIPTION OF THE DRAWINGS

FIG. 1B Leptin; and FIG. 1C RANTES, selected from the list from Table 3 shown herein in the Examples. 95 plasma samples from individuals having AD and having mean MMSE scores of 20, and mean age of 74, was compared to plasma sample from 88 age-matched controls having mean MMSE score of 30. Non-parametric, unpaired t tests comparing the mean concentration of each protein was used to determine statistical significance (p-value).

DETAILED DESCRIPTION OF THE INVENTION

Figure 1A:
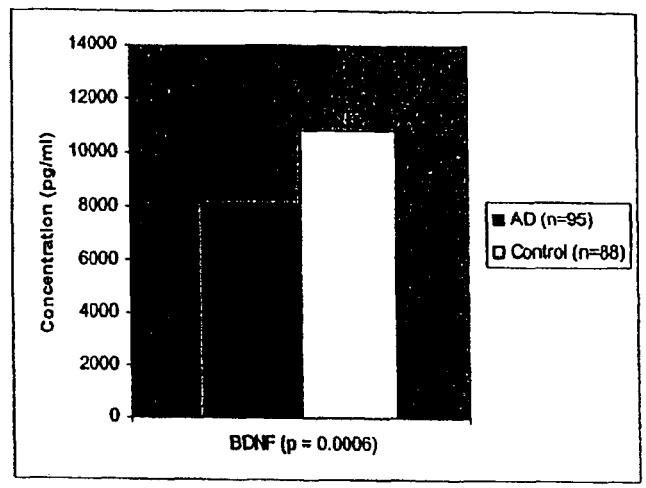
FIGS. 1A-1C show ELISA results for 3 proteins, FIG. 1A BDNF.

Inflammation and injury responses are invariably associated with neuron degeneration in AD, Parkinson's Disease (PD), frontotemporal dementia, cerebrovascular disease, multiple sclerosis, and neuropathies. The brain and CNS are not only immunologically active in their own accord, but also have complex peripheral immunologic interactions. Fiala et al. (1998 Mol Med. July; 4(7):480-9) has shown that in Alzheimer's disease, alterations in the permeability of the blood-brain barrier and chemotaxis, in part mediated by chemokines and cytokines, may permit the recruitment and transendothelial passage of peripheral cells into the brain parenchyma. A paradigm of the blood-brain barrier was constructed utilizing human brain endothelial and astroglial cells with the anatomical and physiological characteristics observed in vivo. This model was used to test the ability of monocytes/macrophages to transmigrate when challenged by A beta 1-42 on the brain side of the blood-brain barrier model. In that model A beta 1-42 and monocytes on the brain side potentiated monocyte transmigration from the blood side to the brain side. In some individuals, circulating monocytes/macrophages, when recruited by chemokines produced by activated microglia and macrophages, could add to the inflammatory destruction of the brain in Alzheimer's disease.

The inventors assert that the monitoring for relative concentrations of many secreted markers measured simultaneously in the serum is a more sensitive method for monitoring the progression of disease than the absolute concentration of any single biochemical markers have been able to achieve. A composite or array embodying the use of 5, 10, 20, 30, 40, 50, 60, 70, 80, 90, 100, 110, 120, 130, 140, 150, 160, 170, 180, 190, 200 markers in Table 7 simultaneously, consisting of antibodies bound to a solid support or protein bound to a solid support, for the detection of inflammation and injury response markers associated with neuron degeneration in AD, PD, frontotemporal dementia, cerebrovascular disease, multiple sclerosis, and neuropathies.

The inventors have discovered a collection of biochemical markers (collectively termed "AD biomarkers") useful for diagnosis of AD, aiding in diagnosis of AD, monitoring AD in AD patients (e.g., tracking disease progression in AD patients, which may be useful for tracking the effect of medical or surgical therapy in AD patients), stratifying AD patients, and diagnosing or aiding in the diagnosis of mild cognitive impairment (MCI) as well as diagnosing or aiding in the diagnosis of cognitive impairment. The AD biomarkers are present in biological fluids of individuals. In some examples, the AD biomarkers are present in peripheral biological fluids (e.g., blood) of individuals, allowing collection of samples by procedures that are relatively non-invasive, particularly as compared to the lumbar puncture procedure commonly used to collect cerebrospinal fluid samples.

DEFINITIONS

As used herein, the terms "Alzheimer's patient", "AD patient", and "individual diagnosed with AD" all refer to an individual who has been diagnosed with AD or has been given a probable diagnosis of Alzheimer's Disease (AD).

As used herein, the phrase "AD biomarker" refers to a biomarker that is an AD diagnosis biomarker.

The term "AD biomarker polynucleotide", as used herein, refers to any of: a polynucleotide sequence encoding a AD biomarker, the associated trans-acting control elements (e.g., promoter, enhancer, and other gene regulatory sequences), and/or mRNA encoding the AD biomarker.

As used herein, methods for "aiding diagnosis" refer to methods that assist in making a clinical determination regarding the presence, or nature, of the AD or MCI, and may or may not be conclusive with respect to the definitive diagnosis. Accordingly, for example, a method of aiding diagnosis of AD can comprise measuring the amount of one or more AD biomarkers in a biological sample from an individual.

As used herein, the term "stratifying" refers to sorting individuals into different classes or strata based on the features of a neurological disease. For example, stratifying a population of individuals with Alzheimer's disease involves assigning the individuals on the basis of the severity of the disease (e.g., mild, moderate, advanced, etc.).

As used herein, the term "predicting" refers to making a finding that an individual has a significantly enhanced probability of developing a certain neurological disease.

As used herein, the phrase "neurological disease" refers to a disease or disorder of the central nervous system. Neurological diseases include multiple sclerosis, neuropathies, and neurodegenerative disorders such as AD, Parkinson's disease, amyotrophic lateral sclerosis (ALS), mild cognitive impairment (MCI) and frontotemporal dementia.

As used herein, "biological fluid sample" encompasses a variety of fluid sample types obtained from an individual and can be used in a diagnostic or monitoring assay. The definition encompasses blood, cerebral spinal fluid (CSF), urine and other liquid samples of biological origin. The definition also includes samples that have been manipulated in any way after their procurement, such as by treatment with reagents, solubilization, or enrichment for certain components, such as proteins or polynucleotides.

As used herein, the term "peripheral biological fluid sample" refers to a biological fluid sample that is not derived from the central nervous system (i.e., is not a CSF sample) and includes blood samples and other biological fluids not derived from the CNS.

A "blood sample" is a biological sample which is derived from blood, preferably peripheral (or circulating) blood. A blood sample may be, for example, whole blood, plasma or serum.

An "individual" is a mammal, more preferably a human. Mammals include, but are not limited to, humans, primates, farm animals, sport animals, rodents and pets.

A "Normal" individual or sample from a "Normal" individual as used herein for quantitative and qualitative data refers to an individual who has or would be assessed by a physician as not having AD or MCI, and has an Mini-Mental State Examination (MMSE) (referenced in Folstein et al., *J. Psychiatr. Res* 1975; 12:1289-198) score or would achieve a MMSE score in the range of 25-30. A "Normal" individual is generally age-matched within a range of 5 to 10 years, including but not limited to an individual that is age-matched, with the individual to be assessed.

An "individual with mild AD" is an individual who (a) has been diagnosed with AD or has been given a diagnosis of probable AD, and (b) has either been assessed with the Mini-Mental State Examination (MMSE) (referenced in Folstein et al., *J. Psychiatr. Res* 1975; 12:1289-198) and scored 22-27 or would achieve a score of 22-27 upon MMSE testing. Accordingly, "mild AD" refers to AD in a individual who has either been assessed with the MMSE and scored 22-27 or would achieve a score of 22-27 upon MMSE testing.

An "individual with moderate AD" is an individual who (a) has been diagnosed with AD or has been given a diagnosis of probable AD, and (b) has either been assessed with the MMSE and scored 16-21 or would achieve a score of 16-21 upon MMSE testing. Accordingly, "moderate AD" refers to AD in a individual who has either been assessed with the MMSE and scored 16-21 or would achieve a score of 16-21 upon MMSE testing.

An "individual with severe AD" is an individual who (a) has been diagnosed with AD or has been given a diagnosis of probable AD, and (b) has either been assessed with the MMSE and scored 12-15 or would achieve a score of 12-15 upon MMSE testing. Accordingly, "severe AD" refers to AD in a individual who has either been assessed with the MMSE and scored 12-15 or would achieve a score of 12-15 upon MMSE testing.

As used herein, the term "treatment" refers to the alleviation, amelioration, and/or stabilization of symptoms, as well as delay in progression of symptoms of a particular disorder. For example, "treatment" of AD includes any one or more of: elimination of one or more symptoms of AD, reduction of one or more symptoms of AD, stabilization of the symptoms of AD (e.g., failure to progress to more advanced stages of AD), and delay in progression (i.e., worsening) of one or more symptoms of AD.

As used herein, the phrase "fold difference" refers to a numerical representation of the magnitude difference between a measured value and a reference value for an AD biomarker. Fold difference is calculated mathematically by division of the numeric measured value with the numeric reference value. For example, if a measured value for an AD biomarker is 20 nanograms/milliliter (ng/ml), and the reference value is 10 ng/ml, the fold difference is 2 (20/10=2). Alternatively, if a measured value for an AD biomarker is 10 nanograms/milliliter (ng/ml), and the reference value is 20 ng/ml, the fold difference is 10/20 or −0.50 or −50%).

As used herein, a "reference value" can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the individual with AD, MCI or cognitive impairment, but at an earlier point in time, or a value obtained from a sample from an AD patient other than the individual being tested, or a "normal" individual, that is an individual not diagnosed with AD. The reference value can be based on a large number of samples, such as from AD patients or normal individuals or based on a pool of samples including or excluding the sample to be tested.

As used herein, "a", "an", and "the" can mean singular or plural (i.e., can mean one or more) unless indicated otherwise.

Methods of the Invention

Methods for Identifying Biomarkers

The invention provides methods for identifying one or more biomarkers useful for diagnosis, aiding in diagnosis, stratifying, assessing risk, monitoring, and/or predicting a neurological disease. In certain aspects of the invention, levels of a group of biomarkers are obtained for a set of peripheral biological fluid samples from one or more individuals. The samples are selected such that they can be segregated into one or more subsets on the basis of a neurological disease (e.g., samples from normal individuals and those diagnosed with amyotrophic lateral sclerosis or samples from individuals with mild Alzheimer's disease and those with severe Alzheimer's disease and/or other neurological diseases, such as neurodegenerative diseases). The measured values from the samples are compared to each other to identify those biomarkers which differ significantly amongst the subsets. Those biomarkers that vary significantly amongst the subsets may then be used in methods for aiding in the diagnosis, diagnosis, stratification, monitoring, and/or prediction of neurological disease. In other aspects of the invention, measured values for a set of peripheral biological fluid samples from one or more individuals (where the samples can be segregated into one or more subsets on the basis of a neurological disease) are compared, wherein biomarkers that vary significantly are useful for aiding in the diagnosis, diagnosis, stratification, monitoring, and/or prediction of neurological disease. In further aspects of the invention, levels of a set of peripheral biological fluid samples from one or more individuals (where the samples can be segregated into one or more subsets on the basis of a neurological disease) are measured to produced measured values, wherein biomarkers that vary significantly are useful for aiding in the diagnosis, diagnosis, stratification, monitoring, and/or prediction of neurological disease.

The instant invention utilizes a set of peripheral biological fluid samples, such as blood samples, that are derived from one or more individuals. The set of samples is selected such that it can be divided into one or more subsets on the basis of a neurological disease. The division into subsets can be on the basis of presence/absence of disease, stratification of disease (e.g., mild vs. moderate), or subclassification of disease (e.g., relapsing/remitting vs. progressive relapsing). Biomarkers measured in the practice of the invention may be any proteinaceous biological marker found in a peripheral biological fluid sample. Tables 7 and 8 contain a collection of exemplary biomarkers. Additional biomarkers are described herein in the Examples.

Accordingly, the invention provides methods identifying one or more biomarkers which can be used to aid in the diagnosis, to diagnose, detect, stratify, and/or predict neurological diseases such as neurodegenerative disorders. The methods of the invention are carried out by obtaining a set of measured values for a plurality of biomarkers from a set of peripheral biological fluid samples, where the set of peripheral biological fluid samples is divisible into at least two subsets in relation to a neurological disease, comparing said measured values between the subsets for each biomarker, and identifying biomarkers which are significantly different between the subsets.

The process of comparing the measured values may be carried out by any method known in the art, including Significance Analysis of Microarrays, Tree Harvesting, CART, MARS, Self Organizing Maps, Frequent Item Set, or Bayesian networks.

In one aspect, the invention provides methods for identifying one or more biomarkers useful for the diagnosis of a neurological disease by obtaining measured values from a set of peripheral biological fluid samples for a plurality of biomarkers, wherein the set of peripheral biological fluid samples is divisible into subsets on the basis of a neurological disease, comparing the measured values from each subset for at least one biomarker; and identifying at least one biomarker for which the measured values are significantly different between the subsets. In some embodiments, the comparing process is carried out using Significance Analysis of Microarrays. In certain embodiments, the neurodegenerative disease is from the group consisting of Alzheimer's disease, Parkinson's disease, Huntington's disease, and amyotrophic lateral sclerosis (ALS).

In another aspect, the invention provides methods for identifying at least one biomarker useful for aiding in the diagnosis of a neurological disease by obtaining measured values from a set of peripheral biological fluid samples for a plurality of biomarkers, wherein the set of peripheral biological fluid samples is divisible into subsets on the basis of a neurological disease, comparing the measured values from each subset for at least one biomarker; and identifying biomarkers for which the measured values are significantly different between the subsets.

In a further aspect, the invention provides methods for identifying at least one biomarker useful for the stratification of a neurological disease by obtaining measured values from a set of peripheral biological fluid samples for a plurality of biomarkers, wherein the set of peripheral biological fluid samples is divisible into subsets on the basis of strata of a neurological disease, comparing the measured values from each subset for at least one biomarker; and identifying biomarkers for which the measured values are significantly different between the subsets.

In another aspect, the invention provides methods for identifying at least one biomarker useful for the monitoring of a neurological disease by obtaining measured values from a set of peripheral biological fluid samples for a plurality of biomarkers, wherein the set of peripheral biological fluid samples is divisible into subsets on the basis of strata of a neurological disease, comparing the measured values from each subset for at least one biomarker; and identifying biomarkers for which the measured values are significantly different between the subsets. In other examples, the measured values are obtained from peripheral biological fluid samples of varying sources.

In yet another aspect, the invention provides methods for identifying at least one biomarker useful for the prediction of a neurological disease by obtaining measured values from a set of peripheral biological fluid samples for a plurality of biomarkers, wherein the set of peripheral biological fluid samples is divisible into subsets on the basis of a neurological disease, comparing the measured values from each subset for at least one biomarker; and identifying biomarkers for which the measured values are significantly different between the subsets. In other examples, the measured values are obtained from peripheral biological fluid samples of varying sources.

Methods of Assessing Cognitive Function

Provided herein are methods for assessing cognitive function, assessing cognitive impairment, diagnosing or aiding diagnosis of cognitive impairment by obtaining measured levels of one or more AD diagnosis biomarkers in a biological fluid sample from an individual, such as for example, a peripheral biological fluid sample from an individual, and comparing those measured levels to reference levels. Reference to "AD diagnosis markers" "AD biomarker" and "Biomarker" (used interchangeably herein) are terms of convenience to refer to the markers described herein and their use, and is not intended to indicate the markers are only used to diagnose AD. As this disclosure makes clear, these biomarkers are useful for, for example, assessing cognitive function, assessing MCI, assessing risk of developing AD, stratifying AD, etc. AD biomarkers include but are not limited to secreted proteins or metabolites present in a person's biological fluids (that is, a biological fluid sample), such as for example, blood, including whole blood, plasma or serum; urine; cerebrospinal fluid; tears; and saliva. Biological fluid samples encompass clinical samples, and also includes serum, plasma, and other biological fluids. A blood sample may include, for example, various cell types present in the blood including platelets, lymphocytes, polymorphonuclear cells, macrophages, erythrocytes.

As described herein, assessment of results can depend on whether the data were obtained by the qualitative or quantitative methods described herein and/or type of reference point used. For example, as described in Example 4, qualitative measurement of AD biomarker levels relative to another reference level, which may be relative to the level of another AD biomarker, may be obtained. In other methods described herein, such as in Example 7, quantitative or absolute values, that is protein concentration levels, in a biological fluid sample may be obtained. "Quantitative" result or data refers to an absolute value (see Example 7), which can include a concentration of a biomarker in pg/ml or ng/ml of molecule to sample. An example of a quantitative value is the measurement of concentration of protein levels directly for example by ELISA. "Qualitative" result or data provides a relative value which is as compared to a reference value. In some examples herein (Example 4), qualitative measurements are assessed by signal intensity on a filter. In some examples herein, multiple antibodies specific for AD biomarkers are attached to a suitable surface, e.g. as slide or filter. As described herein in Examples 11 and 12, qualitative assessment of results may include normalizing data. In this disclosure, various sets of biomarkers are described. It is understood that the invention contemplates use of any of these sets, any one or more members of the sets, as well as markers comprising the sets.

In one aspect, the present invention provides methods of aiding diagnosis of Alzheimer's disease ("AD") and diagnosing AD, by obtaining measured levels of one or more AD diagnosis biomarkers in a biological fluid sample from an individual, such as for example, a peripheral biological fluid sample from an individual, and comparing those measured levels to reference levels. In some examples, a peripheral biological fluid sample is plasma.

In some examples, the AD diagnosis biomarkers are selected from the group shown in Table 7. In some examples, the AD diagnosis biomarkers are selected from the group GCSF; IFN-g; IGFBP-1; BMP-6; BMP-4; Eotaxin-2; IGFBP-2; TARC; RANTES; ANG; PARC; Acrp30; AgRP (ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; and EGF-R. In some examples, the AD diagnosis biomarker(s) is/are selected from the group shown in Table 8. Additionally, Tables 9A1-9A2 and 9B provide a listing of biomarkers (clustered by methods as described herein) in order of highest ranked biomarker to lowest ranked biomarker within each cluster based on score value) that are significantly increased (9A1-9A2) or decreased (9B) in AD compared to age-matched normal controls plus other non-AD forms of neurodegeneration, such as for example PD and PN (that is, as compared to all controls). Generally, a significant increase in a biomarker as compared to an appropriate control is indicative of AD, and a significant decrease in a biomarker as compared to an appropriate control is indicative of AD. The columns from left to right in Tables 9A1-9A2 and 9B are Biomarker name, Score(d); Fold change; q-value(%); and cluster number. Any one or more of the biomarkers listed in Tables 9A1-9A2 and 9B, that is, reagents specific for the biomarker, can be used in the methods disclosed herein, such as for example, for aiding in the diagnosis of or diagnosing AD. In some examples, any one or more of the biomarkers listed in Tables 9A1-9A2 and 9B can be used to diagnose AD as distinguished from other non-AD neurodegenerative diseases or disorders, such as for example PD and PN.

Tables 10A1-10A2 and 10B provide a listing of biomarkers (not clustered and in order of highest ranked biomarker to lowest ranked biomarker based on score value) that are significantly increased (10A1-10A2) or decreased (10B) in AD compared to healthy age-matched controls. The columns from left to right in Tables 10A1-10A2 and 10B, Tables 11A1-11A2 and 11B, and Tables 12A-12B are Biomarker name, Score(d); Fold change; and q-value(%). Based on Tables 10A1-10A2 and 10B, identified biomarkers that are significantly increased in AD as compared to healthy age-matched controls include (in descending order based on score): BTC; ANG-2; MIF; IGFBP-6; spg130; CTACK; IGFBP3; MIP-1a; TRAIL R4; IL-12 p40; AR; NT-4; VEGF-D; OSM; OST; IL-11; sTNF R1; I-TAC; Eotaxin; TECK; PIGF; bNGF; Lymphotactin; MIP-3b; HCC-4; ICAM-3; DTK; IL-1 RI; IGF-1 SR; GRO; GITR-Light; HGF; IL-1R4/ST; IL-2 Ra; ENA-78; and FGF-9. Based on Tables 10A1-10A2 and 10B, identified biomarkers that are significantly decreased in AD as compared to healthy age-matched controls include (in descending order based on score): MCP-2; M-CSF; MCP-3; MDC; MCP-4; IL-1b; IL-4; IL-1a; BLC; CK b8-1; IL-2; IL-15; MIP3a; MIG; SCF; IL-6; IL-16; Eotaxin-3; I-309; TGF-beta; TGF-alpha; GDNF; LIGHT; SDF; IFG-1; Fractalkine; IL-5; Flt-3 ligand; GM-CSF; and GCP-2. Any one or more of the biomarkers listed in Tables 10A1-10A2 and 10B, that is, reagents specific for the biomarker, can be used in the methods disclosed herein, such as for example, for aiding in the diagnosis of or diagnosing AD. In some examples, biomarkers are selected for use in methods disclosed herein, such as for example, for aiding in the diagnosis of or diagnosing AD that have a p-value of equal to or less than 0.05, (or a q-value (%) of equal to or less than 5.00). For Table 10A1-10A2 (biomarkers increased or positively correlated) biomarkers GRO, GITR-Light, IGFBP, HGF, IL-1R4/ST, IL-2Ra, ENA-78, and FGF-9 have a P-value of greater than 0.05. Accordingly, in some examples, positively correlated biomarkers for use in the methods as disclosed herein, such as for example, for aiding in the diagnosis of or diagnosing AD are selected from the group consisting of biomarkers listed in Table 10A1-10A2, excluding biomarkers GRO, GITR-Light, IGFBP, HGF, IL-1R4/ST, IL-2Ra, ENA-78, and FGF-9. For Table 10B (biomarkers decreased or negatively correlated) biomarkers BMP-4, Flt-3 ligand, GM-CSF, IGFBP-4, GCP-2, and TARC have a p-value of greater than 0.05. Accordingly, in some examples, negatively correlated biomarkers for use in the methods as disclosed herein, such as for example, for aiding in the diagnosis of or diagnosing AD are selected from the group consisting of biomarkers listed in Table 10B, excluding biomarkers BMP-4, Flt-3 ligand, GM-CSF, IGFBP-4, GCP-2, and TARC.

Tables 11A1-11A2 and 11B provide a listing of biomarkers (not clustered and in order of highest ranked biomarker to lowest ranked biomarker based on score value) that are significantly increased (11A1-11A2) or decreased (11B) in AD compared to age-matched degenerative controls. Based on Tables 11A1-11A2 and 11B, identified biomarkers that are significantly increased in AD as compared to age-matched other non-AD neurodegenerative controls include (in descending order based on score): TRAIL R4; Eotaxin; IL-12 p40; BTC-1; MIF; OST; MIP-1a; sTNF R1; IL-11; Lymphotactin; NT-4; VEFG-D; HGF; IGFBP3; IGFBP-1; OSM; IL-1R1; PIGF; IGF-1 SR; CCL-28; IL-2 Ra; IL-12 p70; GRO; IGFBP-6; IL-17; CTACK; I-TAC; ICAM-3; ANG-2; MIP-3b; FGF-9; HCC-4; IL-1R4/ST; GITR; and DTK. Based on Tables 11A1-11A2 and 11B, identified biomarkers that are significantly decreased in AD as compared to age-matched other non-AD neurodegenerative controls include (in descending order based on score): MCP-2; M-CSF; MCP-3; MDC; MCP-4; IL-1b; IL-4; IL-1a; BLC; CKb8-1; IL-2; IL-15; MIP3a; MIG; SCF; IL-6; IL-16; Eotaxin-3; I-309; TGF-beta; TNF-alpha; GDNF; LIGHT; SDF-1; IFG-1; Fractalkine; IL-5; Fit-3 Ligand; GM-CSF; and GCP-2. Any one or more of the biomarkers listed in Tables 11A1-11A2 and 11B, that is, reagents specific for the biomarkers, can be used in the methods disclosed herein, such as for example, for aiding in the diagnosis of or diagnosing AD. For Table 11A1-11A2 (biomarkers increased or positively correlated) biomarkers IL-1ra, IL-2ra, PARC, FAS, IL-12 p70, NAP-2, GRO, NT-3, IGFBP-6, TIMP-1, IL-17, IGFBP-2, CTACK, I-TAC, ICAM-3, ANG-2, FGF-4, MIP-3b, FGF-9, HCC-4, IL-1R4/ST, ANG, GITR, DTK, IL-6 R, EGF-R have a p-value of greater than 0.05. Accordingly, in some examples, positively correlated biomarkers for use in the methods as disclosed herein for aiding in the diagnosis of or diagnosing AD are selected from the group consisting of biomarkers listed in Table 11A1-11A2, excluding biomarkers IL-1ra, IL-2ra, PARC, FAS, IL-12 p'70, NAP-2, GRO, NT-3, IGFBP-6, TIMP-1, IL-17, IGFBP-2, CTACK, I-TAC, ICAM-3, ANG-2, FGF-4, MIP-3b, FGF-9, HCC-4, IL-1R4/ST, ANG, GITR, DTK, IL-6 R, EGF-R. For Table 11B (biomarkers decreased or negatively correlated) biomarkers IL-1a, MCP-2, IGFBP-4, spg130, SDF-1, M-CSF, MIP-1d, IL-10, GM-CSF, TNF-a, MDC, FGF-6, TNF-b, IFN-gamma, and GDNF have a p-value of less than 0.05. Accordingly, in some examples, negatively correlated biomarkers for use in the methods as disclosed herein, such as for example, for aiding in the diagnosis of or diagnosing AD are selected from the group consisting of biomarkers IL-1a, MCP-2, IGFBP-4, spg130, SDF-1, M-CSF, MIP-1d, IL-10, GM-CSF, TNF-a, MDC, FGF-6, TNF-b, IFN-gamma, and GDNF that have a p-value of less than 0.05. It is contemplated that biomarkers having a p-value of greater than 0.05 may also be used in the methods as described herein as long as appropriate controls are used. In some examples, methods comprise the use of at least one biomarker having a p-value of greater than 0.05 along with at least one biomarker having a p-value of less than 0.05.

Tables 12A-12B provide a listing of biomarkers (not clustered and in order of highest ranked biomarker to lowest ranked biomarker based on score value) that are significantly increased (12A) or decreased (12B) in AD plus other non-AD neurodegenerative controls with reference to age matched controls. Any one or more of the biomarkers listed in Tables 12A-12B, that is, reagents specific for the biomarker, can be used in the methods disclosed herein, such as for example, for aiding in the diagnosis of or diagnosing neurodegenerative diseases, including AD. In further examples, the AD diagnosis biomarker is selected from Lymphotactin and IL-11 and in other examples, comprises Lymphotactin and IL-11. In further examples, an AD diagnosis markers is selected from the group consisting of: BTC; SDF-1; MCP-2; IFN-gamma; IGFBP-4; IGF-1SR; IL-8; GM-CSF; and ANG-2, as described in the Examples. In further examples, an AD diagnosis marker is selected from the group consisting of IFN-gamma and IL-8, as described in the Examples. In yet other examples, an AD diagnosis biomarker is selected from the group consisting of biomarkers sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and FGF-6, as described in the Examples. In further examples, an AD diagnosis biomarker is selected from the group consisting of BDNF, PDGF-BB, Leptin and RANTES. As shown herein in the examples, quantitative Leptin and BDNF levels have a statistically significant positive correlation with MMSE scores; quantitative PDGF-BB levels have a statistically significant negative correlation with MMSE scores in men; and quantitative RANTES levels have a statistically significant positive correlation with PDGF-BB and BDNF. In some examples, the AD diagnosis biomarkers for use in methods of aiding diagnosis of Alzheimer's disease ("AD") and diagnosing AD include two or more of the following 4 biomarkers: BDNF, PDGF-BB, Leptin and RANTES. In further examples, the AD diagnosis biomarkers for use in methods of aiding diagnosis of Alzheimer's disease ("AD") and diagnosing AD comprise Leptin and RANTES; Leptin and BDNF; Leptin and PDGF-BB; Leptin, RANTES and BDNF; Leptin, RANTES and PDGF-BB; Leptin, BDNF and PDGF-BB; RANTES and BDNF; RANTES and PDGF-BB; RANTES, BDNF, and PDGF-BB; BDNF and PDGF-BB; or Leptin, RANTES, BDNF and PDGF-BB. In some examples, the AD diagnosis markers for use in methods of aiding diagnosis of AD or diagnosing AD comprise Leptin, RANTES, BDNF and PDGF-BB. In other examples, the AD diagnosis markers for use in methods of aiding diagnosis of AD or diagnosing AD consist essentially of or consist of Leptin, RANTES, BDNF and PDGF-BB.

In some examples, provided herein are methods of aiding diagnosis of neurological disease, such as neurodegenerative disease, and diagnosing neurological disease, such as neurodegenerative disease, by obtaining measured levels of one or more AD diagnosis biomarkers shown in Tables 12A-12B (biomarkers that are increased or decreased, respectively) in neurodegenerative controls compared to healthy age-matched controls) in a biological fluid sample from an individual, such as for example, a peripheral biological fluid sample from an individual, and comparing those measured levels to reference levels. Such methods may be used for example, as an initial screening for neurological disease. In some examples, methods for aiding diagnosis of AD and/or diagnosing AD as described herein may be used before or concurrently with methods for aiding diagnosis of neurological disease and/or diagnosing neurological disease or after, for example, as a secondary screen. Additionally or alternatively, methods of aiding diagnosis of AD or diagnosing AD and/or distinguishing AD from other non-AD neurological diseases may comprise obtaining measured levels of one or more AD diagnosis biomarkers shown in Tables 9A1-9A2 and 9B in a biological fluid sample from an individual, such as for example, a peripheral biological fluid sample from an individual, and comparing those measured levels to reference levels. In some examples, a peripheral biological fluid sample is plasma.

Methods of assessing cognitive function, aiding diagnosis of AD and diagnosing AD as described herein may comprise any of the following steps of obtaining a biological fluid sample from an individual, measuring the level of at least one AD diagnosis biomarker in the sample and comparing the measured level to an appropriate reference; obtaining measured levels of at least one AD diagnosis biomarker in a sample and comparing the measured level to an appropriate reference; comparing measured levels of at least one AD diagnosis biomarker obtained from a sample to an appropriate reference; measuring the level of at least one AD diagnosis biomarker in a sample; measuring the level of at least one AD diagnosis biomarker in a sample and comparing the measured level to an appropriate reference; diagnosing AD based on comparison of measured levels to an appropriate reference; or obtaining a measured value for at least one AD diagnosis biomarker in a sample. Comparing a measured level of an AD diagnosis biomarker to a reference level or obtaining a measured value for an AD diagnosis biomarker in a sample may be performed for 1, 2, 3, 4, 5, 6, 7, 8, 9, 10, or more AD diagnosis biomarker(s). The present invention also provides methods of evaluating results of the analytical methods described herein. Such evaluation generally entails reviewing such results and can assist, for example, in advising regarding clinical and/or diagnostic follow-up and/or treatment options. The present invention also provides methods for assessing a biological fluid sample for an indicator of any one or more of the following: cognitive function and/or impairment; MCI; AD; extent of AD, such as, for example, mild, moderate, severe; progression of AD; by measuring the level of or obtaining the measured level of or comparing a measured level of an AD diagnosis biomarker as described herein. Methods of assessing cognitive impairment includes the ADAS-COG, which is generally accepted to be equivalent to MMSE scoring.

Provided herein are methods for assessing the efficacy of treatment modalities in individuals, or population(s) of individuals, such as from a single or multiple collection center(s), subject to impaired cognitive function and/or diagnosed with AD comprising anyone of the following steps: obtaining a biological fluid sample from the individual(s) subject to treatment; measuring the level of at least one AD diagnosis biomarker in the sample and comparing the measured level to an appropriate reference, which in some examples is a measured level of the biomarker in a fluid sample obtained from the individual(s) prior to treatment; obtaining measured levels of at least one AD diagnosis biomarker in a sample from the individual(s) and comparing the measured level to an appropriate reference; comparing measured levels of at least one AD diagnosis biomarker obtained from a sample from the individual(s) to an appropriate reference; measuring the level of at least one AD diagnosis biomarker in a sample from the individual(s); measuring the level of at least one AD diagnosis biomarker in a sample from the individual(s) and comparing the measured level to an appropriate reference; diagnosing efficacy of treatment based on comparison of measured levels to an appropriate reference; or obtaining a measured value for at least one AD diagnosis biomarker in a sample. Measured levels of at least one AD diagnosis biomarker may be obtained once or multiple times during assessment of the treatment modality.

For methods of diagnosing AD as described herein, the reference level is generally a predetermined level considered 'normal' for the particular AD diagnosis biomarker (e.g., an average level for age-matched individuals not diagnosed with AD or an average level for age-matched individuals diagnosed with neurological disorders other than AD and/or healthy age-matched individuals), although reference levels which are determined contemporaneously (e.g., a reference value that is derived from a pool of samples including the sample being tested) are also contemplated. Also provided are methods of aiding in the diagnosis of Alzheimer's disease ("AD") by comparing a measured level of at least one AD diagnosis biomarker in a biological fluid sample, such as, for example, a peripheral biological fluid sample from an individual with a reference level. Further provided are methods of aiding in the diagnosis of Alzheimer's disease ("AD") by measuring a level of at least one AD diagnosis biomarker in a biological fluid sample, such as, for example, a peripheral biological fluid sample from an individual. For the AD diagnosis biomarkers disclosed herein, a measurement for a marker which is below or above the reference level suggests (i.e., aids in the diagnosis of) or indicates a diagnosis of AD.

In another aspect, the invention provides methods of identifying individuals with mild cognitive impairment (MCI), by obtaining a quantitative measured level for RANTES in a biological fluid sample, such as, for example, a peripheral biological fluid sample from an individual, and comparing that level to a reference level. Generally, the reference level for RANTES is a predetermined level considered 'normal' for RANTES, and may be an age-matched normal level for RANTES, although reference levels which are determined contemporaneously (e.g., a reference value that is derived from a pool of samples including the sample being tested) are also contemplated. Also provided are methods of aiding in the diagnosis of MCI by comparing a quantitative measured level for RANTES in a biological fluid sample, such as, for example, a peripheral biological fluid sample from an individual with a reference level. Further provided are methods for aiding in the diagnosis of MCI by measuring a level for RANTES in a biological fluid sample, such as, for example, a peripheral biological fluid sample from an individual. A finding that the quantitative level of RANTES is low (below the reference level) in the biological fluid sample, such as, for example, the peripheral biological fluid sample from the individual suggests (i.e., aids in the diagnosis of) or indicates a diagnosis of MCI. In certain embodiments, such methods further include measuring, obtaining, and/or comparing the quantitative level of Leptin in the biological fluid sample, such as, for example, a peripheral biological sample. When both RANTES and Leptin levels are utilized, a finding that the quantitative RANTES level is low while the quantitative Leptin level is not (i.e., is substantially the same as or higher than the Leptin reference value) suggests (i.e., aids in the diagnosis of) or indicates a diagnosis of MCI. Accordingly the present invention provides methods for aiding in the diagnosis of mild cognitive impairment (MCI), comprising comparing a measured level for RANTES in a biological fluid sample obtained from an individual to a reference level. In some examples, the methods further comprise comparing a measured value for leptin in the biological fluid sample obtained from the individual to a reference level. In yet other examples, the methods further comprises measuring a level for leptin in said biological fluid sample, thereby producing said measured value for leptin. In yet other examples, the methods comprise measuring a level for RANTES in said biological fluid sample, thereby producing said measured value for RANTES. In yet other examples, the biological fluid sample is a peripheral fluid sample.

In a further aspect, the invention provides methods of monitoring progression of AD in an AD patient. As shown in Example 7, the inventors have found that quantitative levels of RANTES are decreased in AD patients with Questionable AD (MMSE=25-28); and that quantitative levels of RANTES are decreased in AD patients with mild AD (MMSE=20-25), and RANTES levels decrease further as the severity of the AD intensifies. An individual with "Questionable AD" as used herein for quantitative data (also called absolute measurement) is an individual who (a) has been diagnosed with AD or has been given a diagnosis of probable AD, and (b) has either been assessed with the Mini-Mental State Examination (MMSE) (referenced in Folstein et al., *J. Psychiatr. Res* 1975; 12:1289-198) and scored 25-28 or would achieve a score of 25-28 upon MMSE testing. Accordingly, "Questionable AD" refers to AD in a individual having scored 25-28 on the MMSE and or would achieve a score of 25-28 upon MMSE testing. The reference level may be a predetermined level considered 'normal' for the particular RANTES (e.g., an average level for age-matched individuals not diagnosed with AD or MCI), or may be a historical reference level for the particular patient (e.g., a RANTES level that was obtained from a sample derived from the same individual, but at an earlier point in time). Reference levels which are determined contemporaneously (e.g., a reference value that is derived from a pool of samples including the sample being tested) are also contemplated. Accordingly, the invention provides methods for monitoring progression of AD in an AD patient by obtaining a quantitative value for RANTES from a biological fluid sample, such as for example, a peripheral biological fluid sample and comparing measured value to a reference value. Also provided are methods for monitoring progression of AD in an AD patient by comparing a measured value for leptin in a biological fluid sample, such as for example, a peripheral biological fluid sample with a reference value. Further provided are methods for monitoring progression of AD in an AD patient by measuring a level for leptin in a biological fluid sample, such as for example, a peripheral biological fluid sample. A decrease in the measured value indicates or suggests (diagnoses or suggests a diagnosis) progression (e.g., an increase in the severity) of AD in the AD patient.

In a further aspect, the inventors have found that quantitative Leptin levels are decreased in AD patients with Questionable AD; and that the quantitative levels of Leptin are decreased in AD patients with mild AD, and quantitative Leptin levels decrease further as the severity of the AD intensifies; and the quantitative levels of Leptin are positively correlated with MMSE scores (as described in Example 7). The reference level may be a predetermined level considered 'normal' for the particular Leptin (e.g., an average level for age-matched individuals not diagnosed with AD or MCI), or may be a historical reference level for the particular patient (e.g., a Leptin level that was obtained from a sample derived from the same individual, but at an earlier point in time). Quantitative reference levels which are determined contemporaneously (e.g., a reference value that is derived from a pool of samples including the sample being tested) are also contemplated. Accordingly, the invention provides methods for monitoring progression of AD in an AD patient by obtaining a quantitative measured value for Leptin from a biological fluid sample, such as for example, a peripheral biological fluid sample and comparing measured value to a reference value. Also provided are methods for monitoring progression of AD in an AD patient by comparing a measured value for Leptin in a biological fluid sample, such as for example, a peripheral biological fluid sample with a reference value. Further provided are methods for monitoring progression of AD in an AD patient by measuring a level for Leptin in a biological fluid sample, such as for example, a peripheral biological fluid sample. A decrease in the quantitative measured value indicates or suggests (diagnoses or suggests a diagnosis) progression (e.g., an increase in the severity) of AD in the AD patient.

The inventors have found that quantitative BDNF levels are decreased in AD patients with mild AD, and that the quantitative BDNF levels in women are correlated with MMSE scores and BDNF levels decrease further as the severity of the AD intensifies (as described in Example 7). The reference level may be a predetermined level considered 'normal' for the particular BDNF (e.g., an average level for age-matched individuals not diagnosed with AD or MCI), or may be a historical reference level for the particular patient (e.g., a BDNF level that was obtained from a sample derived from the same individual, but at an earlier point in time). Reference levels which are determined contemporaneously (e.g., a reference value that is derived from a pool of samples including the sample being tested) are also contemplated. Accordingly, the invention provides methods for monitoring progression of AD in an AD patient by obtaining a quantitative measured value for BDNF from a biological fluid sample, such as for example, a peripheral biological fluid sample and comparing measured value to a reference value. Also provided are methods for monitoring progression of AD in an AD patient by comparing a quantitative measured value for BDNF in a biological fluid sample, such as for example, a peripheral biological fluid sample with a reference value. Further provided are methods for monitoring progression of AD in an AD patient by measuring a level for BDNF in a biological fluid sample, such as for example, a peripheral biological fluid sample. Generally speaking, a decrease in the measured value indicates or suggests (diagnoses or suggests a diagnosis) progression (e.g., an increase in the severity) of AD in the AD patient.

The inventors have found that quantitative PDGF-BB levels are decreased in AD patients with Questionable AD; that PDGF-BB levels are decreased in Questionable AB compared to Mild AD; and that the MMSE scores for male AD patients are negatively correlated with PDGF-BB levels (as described in Example 7). The reference level may be a predetermined level considered 'normal' for the PDGF-BB (e.g., an average level for age-matched male individuals not diagnosed with AD or MCI), or may be a historical reference level for the particular patient (e.g., a PDGF-BB level that was obtained from a sample derived from the same male individual, but at an earlier point in time). Reference levels which are determined contemporaneously (e.g., a reference value that is derived from a pool of samples including the sample being tested) are also contemplated. Accordingly, the invention provides methods for monitoring progression of AD in an AD patient by obtaining a measured value for PDGF-BB from a biological fluid sample from a male, such as for example, a peripheral biological fluid sample and comparing measured value to a reference value. Also provided are methods for monitoring progression of AD in an AD patient by comparing a measured value for PDGF-BB in a biological fluid sample, such as for example, a peripheral biological fluid sample with a reference value. Further provided are methods for monitoring progression of AD in an AD patient by measuring a level for PDGF-BB in a biological fluid sample, such as for example, a peripheral biological fluid sample. A decrease in the measured value indicates or suggests (diagnoses or suggests a diagnosis) progression (e.g., an increase in the severity) of AD in the AD patient.

Additionally, the invention provides methods of stratifying individuals diagnosed with (or having a probable diagnosis of) AD. The inventors have found that analysis of the levels of BDNF, or BDNF and PDGF-BB in biological fluid samples, such as, peripheral biological fluid samples provides information as to the severity of the AD in the AD patient from whom the peripheral biological fluid sample is derived. The reference values for BDNF and PDGF-BB used in these aspects of the invention are most commonly obtained from a population of AD patients other than the AD patient who is the source of the sample being tested (e.g., a mean or median value derived from a large number of AD patients), although reference levels for BDNF and PDGF-BB which are determined contemporaneously (e.g., a reference values that is derived from a pool of samples including the sample being tested) are also contemplated. Accordingly, the invention provides methods of stratifying AD patients into mild, and more advanced (e.g., moderate and severe) stages of AD ("staging") by obtaining a measured level for BDNF, and comparing the measured value with a reference value for BDNF. Accordingly, the invention provides methods of stratifying AD in an AD patient by obtaining a measured value for BDNF, and, optionally, PDGF-BB, in a biological fluid sample, such as a peripheral biological fluid sample, and comparing the measured level to a reference level. The invention also provides methods of stratifying AD in an AD patient by comparing a measured value for BDNF, and, optionally, PDGF-BB, in a biological fluid sample, such as a peripheral biological fluid sample with a reference value. The invention further provides methods of stratifying AD in an AD patient by measuring BDNF and, optionally, PDGF-BB, in a biological fluid sample, such as a peripheral biological fluid sample. As described in Example 4, and under the experimental conditions disclosed in Example 4 which provide qualitative results, samples which have BDNF levels lower than the reference level suggest or indicate mild AD, while samples with BDNF levels higher than the reference level suggest more advanced AD (i.e., moderate or severe AD). Amongst those samples with BDNF levels higher than the reference level, those also having PDGF-BB levels below the reference level suggest or indicate moderate AD, while those samples also having PDGF-BB levels above the reference level suggest or indicate severe AD. It has been found that for Questionable AD (MMSE score in the range of 25-28) the levels of Leptin and PDGF-BB increase significantly whereas BDNF and RANTES do not change significantly. It has been found that from Mild AD (MMSE score in the range of 20-25) to Moderate AD (MMSE score in the range of 10-20) the level of LEPTIN does not decline whereas the levels for RANTES, BDNF and PDGF-BB declines. Accordingly, in some embodiments (as defined by the above MMSE scores from Example 7), Mild AD is indicated in quantitative assays when the levels of Leptin and/or PDGF-BB increase significantly whereas BDNF and RANTES do not change significantly as compared to Questionable AD as a reference. Accordingly, in some embodiments, (as defined by the above MMSE scores from Example 7), Moderate AD is indicated when Leptin does not decline whereas the levels for RANTES, BDNF and PDGF declines as compared to Mild AD as a reference. Accordingly, provided herein are methods comprising comparing measured values for RANTES and Leptin levels in a biological fluid sample from said patient with reference values for RANTES and Leptin; comparing measured values for brain derived neurotrophic factor (BDNF), Leptin, and RANTES, levels in a biological fluid sample from said patient with reference values for BDNF, Leptin, and RANTES; comparing measured values for Leptin and BB homodimeric platelet derived growth factor (PDGF-BB) levels in a biological fluid sample from said patient with reference values for Leptin and PDGF-BB. Accordingly, the present invention provides methods for stratifying Alzheimer's disease (AD) in an individual, comprising comparing measured values for brain derived neurotrophic factor (BDNF) and BB homodimeric platelet derived growth factor (PDGF-BB) levels in a biological fluid sample from said patient with reference values for BDNF and PDGF-BB. In some examples, the methods further comprise comparing measured values for leptin and Rantes levels with reference values for leptin and Rantes, wherein reference values for BDNF, PDGF-BB, leptin and Rantes are for samples from individuals with MMSE scores from 25 to 28, wherein an increase in leptin and PDGF-BB levels and wherein levels of BDNF and RANTES stay substantially the same indicate mild AD as indicated by an MMSE score of 20-25. The present invention also provides methods of further comprising comparing measured values for leptin and Rantes levels with reference values for leptin and Rantes, wherein reference values for BDNF, PDGF-BB, leptin and Rantes are for samples from individuals with MMSE scores from 20-25, wherein a decrease in Rantes, BDNF, and PDGF levels and wherein levels of Leptin stays substantially the same indicate moderate AD as indicated by an MMSE score of 10-20. Additional biomarkers useful in methods for stratifying AD as described herein in an individual include Lymphotactin and IL-11. An AD biomarker that stays "substantially the same" means that there is not a significant change, and that the values stay about the same. In some embodiments, substantially the same is a change less than any of about 12%, 10%, 5%, 2%, 1%. In some embodiments, a significant change means not statistically significant using standard methods in the art. The methods described above are also applicable to methods for assessing progression of AD. It is understood that the cognitive function indicated by the markers herein can be by other measurements with results or indicia that corresponds to approximately the same level of cognitive function as the MMSE scores provided herein.

The present invention also provides methods of aiding diagnosis of Alzheimer's disease ("AD"), comprising comparing a measured level of at least one AD diagnosis biomarker in a biological fluid sample from an individual to a reference level for the biomarker for each biomarker measured, wherein the at least one AD diagnosis biomarker is selected from Table 7 and has a statistically significant positive correlation with MMSE scores that is comparable to BDNF and/or Leptin correlation with MMSE scores, and wherein the at least one AD diagnosis biomarker is not statistically correlated with age. An AD diagnosis biomarker that has a statistically significant positive correlation with MMSE scores that is comparable to BDNF and/or leptin correlation with MMSE scores means that the biomarker is an AD diagnosis marker. In some examples, the AD diagnosis biomarker is selected from the group of biomarkers consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R and in other examples is selected from the group of biomarkers consisting of basic fibroblast growth factor (bFGF); BB homodimeric platelet derived growth factor (PDGF-BB); brain derived neurotrophic factor (BDNF); epidermal growth factor (EGF), fibroblast growth factor 6 (FGF-6), interleukin-3 (IL-3), soluble interleukin-6 receptor (sIL-6R), leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), and tumor necrosis factor beta (TNF-β). Additional biomarkers are provided in Table 8. Additionally, Tables 9A1-9A2 and 9B provide a listing of biomarkers (clustered by methods as described herein) in order of highest ranked biomarker to lowest ranked biomarker within each cluster based on score value) that are significantly increased (9A1-9A2) or decreased (9B) in AD compared to age-matched normal controls plus other non-AD forms of neurodegeneration, such as for example PD and PN (that is, as compared to all controls). The columns from left to right in Tables 9A1-9A2 and 9B are Biomarker name, Score(d); Fold change; q-value(%); and cluster number. Any one or more of the biomarkers listed in Tables 9A1-9A2 and 9B, that is, reagents specific for the biomarker, can be used in the methods disclosed herein, such as for example, methods for aiding in the diagnosis of or diagnosing AD. In some examples, any one or more of the biomarkers listed in Tables 9A1-9A2 and 9B can be used to diagnose AD. In some examples, any one or more of the biomarkers listed in Tables 9A1-9A2 and 9B can be used to diagnose AD as distinguished from other non-AD neurodegenerative diseases or disorders, such as for example PD and PN.

Tables 10A1-10A2 and 10B provide a listing of biomarkers (not clustered and in order of highest ranked biomarker to lowest ranked biomarker based on score value) that are significantly increased (10A1-10A2) or decreased (10B) in AD compared to healthy age-matched controls. The columns from left to right in Tables 10A1-10A2 and 10B, Tables 11A1-11A2 and 11B, and Tables 12A-12B are Biomarker name, Score(d); Fold change; and q-value(%). Based on Tables 10A1-10A2 and 10B, identified biomarkers that are significantly increased in AD as compared to healthy age-matched controls include (in descending order based on score): BTC; ANG-2; MIF; IGFBP-6; spg130; CTACK; IGFBP3; MIP-1a; TRAIL R4; IL-12 p40; AR; NT-4; VEGF-D; OSM; OST; IL-11; sTNF R1; I-TAC; Eotaxin; TECK; PIGF; bNGF; Lymphotactin; MIP-3b; HCC-4; ICAM-3; DTK; IL-1 RI; IGF-1 SR; GRO; GITR-Light; HGF; IL-1R4/ST; IL-2 Ra; ENA-78; and FGF-9. Based on Tables 10A1-10A2 and 10B, identified biomarkers that are significantly decreased in AD as compared to healthy age-matched controls include (in descending order based on score): MCP-2; M-CSF; MCP-3; MDC; MCP-4; IL-1b; IL-4; IL-1a; BLC; CK b8-1; IL-2; IL-15; MIP3a; MIG; SCF; IL-6; IL-16; Eotaxin-3; I-309; TGF-beta; TGF-alpha; GDNF; LIGHT; SDF; IFG-1; Fractalkine; IL-5; Fit-3 ligand; GM-CSF; and GCP-2. Any one or more of the biomarkers listed in Tables 10A1-10A2 and 10B, that is, reagents specific for the biomarker, can be used in the methods disclosed herein, such as for example, for aiding in the diagnosis of or diagnosing AD. In some examples, biomarkers are selected for use in methods disclosed herein, such as for example, for aiding in the diagnosis of or diagnosing AD that have a p-value of equal to or less than 0.05, (or a q-value (%) of equal to or less than 5.00). For Table 10A1-10A2 (biomarkers increased or positively correlated) biomarkers GRO, GITR-Light, IGFBP, HGF, IL-1R4/ST, IL-2Ra, ENA-78, and FGF-9 have a P-value of greater than 0.05. Accordingly, in some examples, positively correlated biomarkers for use in the methods as disclosed herein for aiding in the diagnosis of or diagnosing AD are selected from the group consisting of biomarkers listed in Table 10A1-10A2, excluding biomarkers GRO, GITR-Light, IGFBP, HGF, IL-1R4/ST, IL-2Ra, ENA-78, and FGF-9. For Table 10B (biomarkers decreased or negatively correlated) biomarkers BMP-4, Fit-3 ligand, GM-CSF, IGFBP-4, GCP-2, and TARC have a p-value of greater than 0.05. Accordingly, in some examples, negatively correlated biomarkers for use in the methods as disclosed herein for aiding in the diagnosis of or diagnosing AD are selected from the group consisting of biomarkers listed in Table 10B, excluding biomarkers BMP-4, Fit-3 ligand, GM-CSF, IGFBP-4, GCP-2, and TARC.

Tables 11A1-11A2 and 11B provide a listing of biomarkers (not clustered and in order of highest ranked biomarker to lowest ranked biomarker based on score value) that are significantly increased (11A1-11A2) or decreased (11B) in AD compared to age-matched degenerative controls. Based on Tables 11A1-11A2 and 11B, identified biomarkers that are significantly increased in AD as compared to age-matched other non-AD neurodegenerative controls include (in descending order based on score): TRAIL R4; Eotaxin; IL-12 p40; BTC-1; MIF; OST; MIP-1a; sTNF R1; IL-11; Lymphotactin; NT-4; VEFG-D; HGF; IGFBP3; IGFBP-1; OSM; IL-1R1; PIGF; IGF-1 SR; CCL-28; IL-2 Ra; IL-12 p70; GRO; IGFBP-6; IL-17; CTACK; I-TAC; ICAM-3; ANG-2; MIP-3b; FGF-9; HCC-4; IL-1R4/ST; GITR; and DTK. Based on Tables 11A1-11A2 and 11B, identified biomarkers that are significantly decreased in AD as compared to age-matched other non-AD neurodegenerative controls include (in descending order based on score): MCP-2; M-CSF; MCP-3; MDC; MCP-4; IL-1b; IL-4; IL-1a; BLC; CKb8-1; IL-2; IL-15; MIP3a; MIG; SCF; IL-6; IL-16; Eotaxin-3; I-309; TGF-beta; TNF-alpha; GDNF; LIGHT; SDF-1; IFG-1; Fractalkine; IL-5; Fit-3 Ligand; GM-CSF; and GCP-2. Any one or more of the biomarkers listed in Tables 11A1-11A2 and 11B, that is, reagents specific for the biomarkers, can be used in the methods disclosed herein, such as for example, for aiding in the diagnosis of or diagnosing AD. For Table 11A1-11A2 (biomarkers increased or positively correlated) biomarkers IL-1ra, IL-2ra, PARC, FAS, IL-12 p'70, NAP-2, GRO, NT-3, IGFBP-6, TIMP-1, IL-17, IGFBP-2, CTACK, I-TAC, ICAM-3, ANG-2, FGF-4, MIP-3b, FGF-9, HCC-4, IL-1R4/ST, ANG, GITR, DTK, IL-6 R, EGF-R have a p-value of greater than 0.05. Accordingly, in some examples, positively correlated biomarkers for use in the methods as disclosed herein, such as for example, for aiding in the diagnosis of or diagnosing AD are selected from the group consisting of biomarkers listed in Table 11A1-11A2, excluding biomarkers IL-1ra, IL-2ra, PARC, FAS, IL-12 p'70, NAP-2, GRO, NT-3, IGFBP-6, TIMP-1, IL-17, IGFBP-2, CTACK, I-TAC, ICAM-3, ANG-2, FGF-4, MIP-3b, FGF-9, HCC-4, IL-1R4/ST, ANG, GITR, DTK, IL-6 R, EGF-R. For Table 11B (biomarkers decreased or negatively correlated) biomarkers IL-1a, MCP-2, IGFBP-4, spg130, SDF-1, M-CSF, MIP-1d, IL-10, GM-CSF, TNF-a, MDC, FGF-6, TNF-b, IFN-gamma, and GDNF have a p-value of less than 0.05. Accordingly, in some examples, negatively correlated biomarkers for use in the methods as disclosed herein for aiding in the diagnosis of or diagnosing AD are selected from the group consisting of biomarkers IL-1a, MCP-2, IGFBP-4, spg130, SDF-1, M-CSF, MIP-1d, IL-10, GM-CSF, TNF-a, MDC, FGF-6, TNF-b, IFN-gamma, and GDNF that have a p-value of less than 0.05.

Tables 12A-12B provide a listing of biomarkers (not clustered and in order of highest ranked biomarker to lowest ranked biomarker based on score value) that are significantly increased (12A) or decreased (12B) in AD plus other non-AD degenerative controls with reference to age matched controls. Any one or more of the biomarkers listed in Tables 12A-12B, that is, reagents specific for the biomarker, can be used in the methods disclosed herein, such as for example, for aiding in the diagnosis of or diagnosing neurological diseases, including AD. In further examples, the AD diagnosis biomarker is selected from Lymphotactin and IL-11 and in other examples, comprise Lymphotactin and IL-11. In further examples, an AD diagnosis markers is selected from the group consisting of BTC; SDF-1; MCP-2; IFN-gamma; IGFBP-4; IGF-1SR; IL-8; GM-CSF; and ANG-2, as described in the Examples. In further examples, an AD diagnosis marker is selected from the group consisting of IFN-gamma and IL-8, as described in the Examples. In yet other examples, an AD diagnosis biomarker is selected from the group consisting of biomarkers sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and FGF-6, as described in the Examples.

The results of the comparison between the measured value(s) and the reference value(s) are used to diagnose or aid in the diagnosis of AD or MCI, to stratify AD patients according to the severity of their disease, or to monitor progression of AD in an AD patient. Accordingly, if the comparison indicates a difference (that is, an increase or decrease) between the measured value(s) and the reference value(s) that is suggestive/indicative of AD or MCI, then the appropriate diagnosis is aided in or made. Conversely, if the comparison of the measured level(s) to the reference level(s) does not indicate differences that suggest or indicate a diagnosis of AD or MCI, then the appropriate diagnosis is not aided in or made. Likewise, when comparison of a measured level for Leptin in a sample derived from an AD patient is decreased in comparison to the reference value, diagnosis of progression of the patient's AD is made or aided in. Similarly, when the comparison of levels of BDNF and PDGF-BB levels in a sample obtained from an AD patient indicates or suggests a particular stage of AD, the diagnosis of the particular stage of AD (mild, moderate or severe) is aided in or made.

As will be understood by those of skill in the art, when, in the practice of the AD diagnosis methods of the invention (i.e., methods of diagnosing or aiding in the diagnosis of AD), more than one AD diagnosis biomarker is used but the markers do not unanimously suggest or indicate a diagnosis of AD, the 'majority' suggestion or indication (e.g., when the method utilizes five AD diagnosis biomarkers, 3 of which suggest/indicate AD, the result would be considered as suggesting or indicating a diagnosis of AD for the individual) is considered the result of the assay. However, in some embodiments in which measured values for at least two AD diagnosis biomarkers are obtained and one of the measured values is for Leptin, the measured value for Leptin must be less than the reference value to indicate or suggest a diagnosis of AD. As will be appreciated by one of skill in the art, methods disclosed herein may include the use of any of a variety of biological markers (which may or may not be AD markers) to determine the integrity and/or characteristics of the biological sample(s). For example, Leptin levels, which are generally higher in females, may be measured as a marker of gender.

In certain embodiments of the invention, levels for AD biomarkers are obtained from an individual at more than one time point. Such "serial" sampling is well suited for the aspects of the invention related to monitoring progression of AD in an AD patient. Serial sampling can be performed on any desired timeline, such as monthly, quarterly (i.e., every three months), semi-annually, annually, biennially, or less frequently. The comparison between the measured levels and the reference level may be carried out each time a new sample is measured, or the data relating to levels may be held for less frequent analysis.

As will be understood by those of skill in the art, biological fluid samples including peripheral biological fluid samples are usually collected from individuals who are suspected of having AD, or developing AD or MCI. The invention also contemplates samples from individuals for whom cognitive assessment is desired. Alternatively, individuals (or others involved in for example research and/or clinicians may desire such assessments without any indication of AD, suspected AD, at risk for AD. For example, a normal individual may desire such information. Such individuals are most commonly 65 years or older, although individuals from whom biological fluid samples, such as peripheral biological fluid samples are taken for use in the methods of the invention may be as young as 35 to 40 years old, when early onset AD or familial AD is suspected.

The invention also provides methods of screening for candidate agents for the treatment of AD and/or MCI by assaying prospective candidate agents for activity in modulating AD biomarkers. The screening assay may be performed either in vitro and/or in vivo. Candidate agents identified in the screening methods described herein may be useful as therapeutic agents for the treatment of AD and/or MCI.

The probability P that the composite is more predictive than any subset of markers present in the composite can be expressed mathematically as:

$$P=1-(1-P_1)(1-P_2)(1-P_3)\ldots(1-P_n)$$

Where the probability $P_1$, $P_2$, $P_n$ represent the probability of individual marker being able to predict clinical phenotypes, and where $1-P_n$ represents the complement of that probability. Any subset of the composite, will always therefore have a smaller value for P. In accordance with a further embodiment of the present invention, the relative concentrations in serum, CSF, or other fluids of the biomarkers cited in Table 7, and other Tables described herein, as a composite, or collective, or any subset of such a composite, composed of 5 (five) or more elements is more predictive than the absolute concentration of any individual marker in predicting clinical phenotypes, disease detection, stratification, monitoring, and treatment of AD, PD, frontotemporal dementia, cerebrovascular disease, multiple sclerosis, and neuropathies.

AD Diagnosis Biomarkers

Immune mechanisms are an essential part of the host defense system and typically feature prominently in the inflammatory response. A growing number of studies are discovering intriguing links between the immune system and the CNS. For example, it has become clear that the CNS is not entirely sheltered from immune surveillance and that various immune cells can traverse the blood-brain barrier. Invading leukocytes can attack target antigens in the CNS or produce growth factors that might protect neurons against degeneration (Hohlfeld et al., 2000, *J. Neuroimmunol.* 107, 161-166). These responses are elicited through a variety of protein mediators, including but not limited to cytokines, chemokines, neurotrophic factors, collectins, kinins, and acute phase proteins in the immune and inflammatory systems, in intercellular communication across neurons, glial cells, endothelial cells and leukocytes. Without being bound by theory, it is hypothesized that the cytokines, chemokines, neurotrophic factors, collectins, kinins, and acute phase proteins listed in Table 7 are differentially expressed in serum associated with neurodegenerative and inflammatory diseases such as Alzheimer's, Parkinson's disease, Multiple Sclerosis, and neuropathies. Cytokines are a heterogeneous group of polypeptide mediators that have been associated with activation of numerous functions, including the immune system and inflammatory responses. Peripheral cytokines also penetrate the blood-brain barrier directly via active transport mechanisms or indirectly via vagal nerve stimulation. Cytokines can act in an autocrine manner, affecting the behavior of the cell that releases the cytokine, or in a paracrine manner, affecting the behavior of adjacent cells. Some cytokines can act in an endocrine manner, affecting the behavior of distant cells, although this depends on their ability to enter the circulation and on their half-life. The cytokine families include, but are not limited to, interleukins (IL-1 alpha, IL-1 beta, IL1ra and IL-2 to IL-18), tumor necrosis factors (TNF-alpha and TNF-beta), interferons (INF-alpha, beta and gamma), colony stimulating factors (G-CSF, M-CSF, GM-CSF, IL-3 and some of the other ILs), and growth factors (EGF, FGF, PDGF, TGF alpha, TGF betas, BMPs, GDFs, CTGF, and ECGF).

The inventors have discovered a collection of biochemical markers present in peripheral bodily fluids that may be used to assess cognitive function, including diagnose or aid in the diagnosis of AD. These "AD diagnosis markers" include, but are not limited to GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In other examples, these "AD diagnosis biomarkers" are: basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β). In other examples, the AD diagnosis markers include one or more of Leptin, RANTES, PDFG-BB and BDNF.

Additionally, Tables 9A1-9A2 and 9B provide a listing of biomarkers (clustered by methods as described herein) in order of highest ranked biomarker to lowest ranked biomarker within each cluster based on score value) that are significantly increased (9A1-9A2) or decreased (9B) in AD compared to age-matched normal controls plus other non-AD forms of neurodegeneration, such as for example PD and PN (that is, as compared to all controls). The columns from left to right in Tables 9A1-9A2 and 9B are Biomarker name, Score (d); Fold change; q-value(%); and cluster number. Any one or more of the biomarkers listed in Tables 9A1-9A2 and 9B, that is, reagents specific for the biomarker, can be used in the methods disclosed herein, such as for example, for aiding in the diagnosis of or diagnosing AD. In some examples, any one or more of the biomarkers listed in Tables 9A1-9A2 and 9B can be used to diagnose AD as distinguished from other non-AD neurodegenerative diseases or disorders, such as for example PD and PN.

Tables 10A1-10A2 and 10B provide a listing of biomarkers (not clustered and in order of highest ranked biomarker to lowest ranked biomarker based on score value) that are significantly increased (10A1-10A2) or decreased (10B) in AD compared to healthy age-matched controls. The columns from left to right in Tables 10A1-10A2 and 10B, Tables 11A1-11A2 and 11B, and Tables 12A-12B are Biomarker name, Score(d); Fold change; and q-value(%). Based on Tables 10A1-10A2 and 10B, identified biomarkers that are significantly increased in AD as compared to healthy age-matched controls include (in descending order based on score): BTC; ANG-2; MIF; IGFBP-6; spg130; CTACK; IGFBP3; MIP-1a; TRAIL R4; IL-12 p40; AR; NT-4; VEGF-D; OSM; OST; IL-11; sTNF R1; I-TAC; Eotaxin; TECK; PIGF; bNGF; Lymphotactin; MIP-3b; HCC-4; ICAM-3; DTK; IL-1 RI; IGF-1 SR; GRO; GITR-Light; HGF; IL-1R4/ST; IL-2 Ra; ENA-78; and FGF-9. Based on Tables 10A1-10A2 and 10B, identified biomarkers that are significantly decreased in AD as compared to healthy age-matched controls include (in descending order based on score): MCP-2; M-CSF; MCP-3; MDC; MCP-4; IL-1b; IL-4; IL-1a; BLC; CK b8-1; IL-2; IL-15; MIP3a; MIG; SCF; IL-6; IL-16; Eotaxin-3; I-309; TGF-beta; TGF-alpha; GDNF; LIGHT; SDF; IFG-1; Fractalkine; IL-5; Flt-3 ligand; GM-CSF; and GCP-2. Any one or more of the biomarkers listed in Tables 10A1-10A2 and 10B, that is, reagents specific for the biomarker, can be used in the methods disclosed herein, such as for example, for aiding in the diagnosis of or diagnosing AD. In some examples, biomarkers are selected for use in methods disclosed herein for aiding in the diagnosis of or diagnosing AD that have a p-value of equal to or less than 0.05, (or a q-value (%) of equal to or less than 5.00). For Table 10A1-10A2 (biomarkers increased or positively correlated) biomarkers GRO, GITR-Light, IGFBP, HGF, IL-1R4/ST, IL-2Ra, ENA-78, and FGF-9 have a P-value of greater than 0.05. Accordingly, in some examples, positively correlated biomarkers for use in the methods as disclosed herein for aiding in the diagnosis of or diagnosing AD are selected from the group consisting of biomarkers listed in Table 10A1-10A2, excluding biomarkers GRO, GITR-Light, IGFBP, HGF, IL-1R4/ST, IL-2Ra, ENA-78, and FGF-9. For Table 10B (biomarkers decreased or negatively correlated) biomarkers BMP-4, Flt-3 ligand, GM-CSF, IGFBP-4, GCP-2, and TARC have a p-value of greater than 0.05. Accordingly, in some examples, negatively correlated biomarkers for use in the methods as disclosed herein for aiding in the diagnosis of or diagnosing AD are selected from the group consisting of biomarkers listed in Table 10B, excluding biomarkers BMP-4, Flt-3 ligand, GM-CSF, IGFBP-4, GCP-2, and TARC.

Tables 11A1-11A2 and 11B provide a listing of biomarkers (not clustered and in order of highest ranked biomarker to lowest ranked biomarker based on score value) that are significantly increased (11A1-11A2) or decreased (11B) in AD compared to age-matched degenerative controls. Based on Tables 11A1-11A2 and 11B, identified biomarkers that are significantly increased in AD as compared to age-matched other non-AD neurodegenerative controls include (in descending order based on score): TRAIL R4; Eotaxin; IL-12 p40; BTC-1; MIF; OST; MIP-1a; sTNF R1; IL-11; Lymphotactin; NT-4; VEFG-D; HGF; IGFBP3; IGFBP-1; OSM; IL-1R1; PIGF; IGF-1 SR; CCL-28; IL-2 Ra; IL-12 p70; GRO; IGFBP-6; IL-17; CTACK; I-TAC; ICAM-3; ANG-2; MIP-3b; FGF-9; HCC-4; IL-1R4/ST; GITR; and DTK. Based on Tables 11A1-11A2 and 11B, identified biomarkers that are significantly decreased in AD as compared to age-matched other non-AD neurodegenerative controls include (in descending order based on score): MCP-2; M-CSF; MCP-3; MDC; MCP-4; IL-1b; IL-4; IL-1a; BLC; CKb8-1; IL-2; IL-15; MIP3a; MIG; SCF; IL-6; IL-16; Eotaxin-3; I-309; TGF-beta; TNF-alpha; GDNF; LIGHT; SDF-1; IFG-1; Fractalkine; IL-5; Flt-3 Ligand; GM-CSF; and GCP-2. Any one or more of the biomarkers listed in Tables 11A1-11A2 and 11B, that is, reagents specific for the biomarkers, can be used in the methods disclosed herein, such as for example, for aiding in the diagnosis of or diagnosing AD. For Table 11A1-11A2

(biomarkers increased or positively correlated) biomarkers IL-1ra, IL-2ra, PARC, FAS, IL-12 p'70, NAP-2, GRO, NT-3, IGFBP-6, TIMP-1, IL-17, IGFBP-2, CTACK, I-TAC, ICAM-3, ANG-2, FGF-4, MIP-3b, FGF-9, HCC-4, IL-1R4/ST, ANG, GITR, DTK, IL-6 R, EGF-R have a p-value of greater than 0.05. Accordingly, in some examples, positively correlated biomarkers for use in the methods as disclosed herein for aiding in the diagnosis of or diagnosing AD are selected from the group consisting of biomarkers listed in Table 11A1-11A2, excluding biomarkers IL-1ra, IL-2ra, PARC, FAS, IL-12 p70, NAP-2, GRO, NT-3, IGFBP-6, TIMP-1, IL-17, IGFBP-2, CTACK, I-TAC, ICAM-3, ANG-2, FGF-4, MIP-3b, FGF-9, HCC-4, IL-1R4/ST, ANG, GITR, DTK, IL-6 R, EGF-R. For Table 11B (biomarkers decreased or negatively correlated) biomarkers IL-1a, MCP-2, IGFBP-4, spg130, SDF-1, M-CSF, MIP-1d, IL-10, GM-CSF, TNF-a, MDC, FGF-6, TNF-b, IFN-gamma, and GDNF have a p-value of less than 0.05. Accordingly, in some examples, negatively correlated biomarkers for use in the methods as disclosed herein for aiding in the diagnosis of or diagnosing AD are selected from the group consisting of biomarkers IL-1a, MCP-2, IGFBP-4, spg130, SDF-1, M-CSF, MIP-1d, IL-10, GM-CSF, TNF-a, MDC, FGF-6, TNF-b, IFN-gamma, and GDNF that have a p-value of less than p equal to or less than 0.05.

Tables 12A-12B provide a listing of biomarkers (not clustered and in order of highest ranked biomarker to lowest ranked biomarker based on score value) that are significantly increased (12A) or decreased (12B) in AD plus other non-AD degenerative controls with reference to age matched controls. Any one or more of the biomarkers listed in Tables 12A-12B, that is, reagents specific for the biomarker, can be used in the methods disclosed herein, such as for example, for aiding in the diagnosis of or diagnosing neurological diseases, including AD. In further examples, the AD diagnosis biomarker is selected from Lymphotactin and IL-11 and in other examples, comprise Lymphotactin and IL-11. In further examples, an AD diagnosis markers is selected from the group consisting of BTC; SDF-1; MCP-2; IFN-gamma; IGFBP-4; IGF-1SR; IL-8; GM-CSF; and ANG-2, as described in the Examples. In further examples, an AD diagnosis marker is selected from the group consisting of IFN-gamma and IL-8, as described in the Examples. In yet other examples, an AD diagnosis biomarker is selected from the group consisting of biomarkers sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and FGF-6, as described in the Examples.

The AD diagnosis biomarkers discovered by the inventors are all known molecules. Brain derived neurotrophic factor (BDNF) is described in, for example Rosenthal et al., 1991, Endocrinology 129(3):1289-94. Basic fibroblast growth factor (bFGF) is described in, for example Abraham et al., 1986, EMBO J. 5(10):2523-28. Epidermal growth factor (EGF) is described in, for example Gray et al., 1983, Nature 303(5919):722-25. Fibroblast growth factor 6 (FGF-6) is described in, for example Marics et al., 1989, Oncogene 4(3): 335-40. Interleukin-3 (IL-3) is described in, for example Yang et al., 1986, Cell 47(1):3-10. Soluble interleukin-6 receptor (sIL-6R) is described in, for example, Taga et al., 1989, Cell 58(3):573-81. Leptin (also known as "ob") is described in, for example Masuzaki et al. 1995, Diabetes 44(7):855-58. Macrophage inflammatory protein-1 delta (MIP-1δ) is described in, for example Wang et al., 1998, J. Clin. Immunol. 18(3): 214-22. Macrophage stimulating protein alpha chain (MSP-α) is described in, for example, Yoshimura et al., 1993, J. Biol. Chem. 268 (21), 15461-68, and Yoshikawa et al., 1999, Arch. Biochem. Biophys. 363(2):356-60. Neutrophil activating peptide-2 (NAP-2) is described in, for example Walz et al., 1991, Adv. Exp. Med. Biol. 305:39-46. Neurotrophin-3 (NT-3) is described in, for example Hohn et al., 1990, Nature 344 (6264):339-41. BB homodimeric platelet derived growth factor (PDGF-BB) is described in, for example Collins et al., 1985, Nature 316(6030):748-50. RANTES is described in, for example Schall et al., 1988, J. Immunol. 141(3):1018-25. Stem cell factor (SCF) is described in, for example Zseboet al., 1990, Cell 63(1):213-24. Soluble tumor necrosis factor receptor-2 (sTNF RII) is described in, for example Schall et al., 1990, Cell 61(2):361-70. Transforming growth factor-beta 3 (TGF-β3) is described in, for example ten Dijke et al., 1988, Proc. Natl. Acad. Sci. U.S.A. 85 (13):4715-19. Tissue inhibitor of metalloproteases-1 (TIMP-1) is described in, for example, Docherty et al., 1985, Nature 318(6041):66-69 and Gasson et al., 1985, Nature 315(6022):768-71. Tissue inhibitor of metalloproteases-2 (TIMP-2) is described in, for example, Stetler-Stevenson et al., 1190, J. Biol. Chem. 265 (23):13933-38. Tumor necrosis factor beta (TNF-β) is described in, for example Gray et al., 1984, Nature 312(5996):721-24. Thrombopoietin (TPO) is described in, for example, Foster et al., 1994, Proc. Natl. Acad. Sci. U.S.A. 91(26):13023-27.

Although the inventors have found acceptable levels of sensitivity and specificity with single AD diagnosis biomarkers for practice of the AD diagnosis methods, the effectiveness (e.g., sensitivity and/or specificity) of the methods of the AD diagnosis methods of the instant invention are generally enhanced when at least two AD diagnosis biomarkers are utilized. In some examples, the methods of the AD diagnosis methods of the instant invention are generally enhanced when at least four AD diagnosis biomarkers are utilized. Multiple AD diagnosis biomarkers may be selected from the AD diagnosis biomarkers disclosed herein by a variety of methods, including "q value" and/or by selecting for cluster diversity. AD diagnosis biomarkers may be selected on the basis of "q value", a statistical value that the inventors derived when identifying the AD diagnosis biomarkers (see Table 3 in Example 1). "q values" for selection of AD diagnosis biomarkers range from less than about 0.0001 to about 0.05 and in some examples, range from about 0.01 to about 0.05. Alternately (or additionally), AD diagnosis biomarkers may be selected to preserve cluster diversity of selected proteins or sample diversity. The inventors have separated the AD diagnosis biomarkers into a number of clusters (see Table 1). Additional clusters of AD diagnosis markers are found in Tables 9A1-9A2 and 9B. Here the clusters are formed by qualitative measurements for each biomarker which are most closely correlated. As used herein, "correlate" or "correlation" is a simultaneous change in value of two numerically valued random variables such as MMSE scores and quantitative protein concentrations or qualitative protein concentrations. As used herein "discriminate" or "discriminatory" is refers to the quantitative or qualitative difference between two or more samples for a given variable. The cluster next to such a cluster is a cluster that is most closely correlated with the cluster. The correlations between biomarkers and between clusters can represented by a hierarchical tree generated by unsupervised clustering using a public web based software called wCLUTO available at: cluto.ccgb.umn.edu/cgi-bin/wCluto/wCluto.cgi. If more than one AD diagnosis biomarker is selected for testing, in some examples, the AD diagnosis biomarkers selected are at least partially diverse (i.e., the AD diagnosis biomarkers represent at least two different clusters, for example, a set of AD diagnosis biomarkers comprising Leptin, BDNF and/or PDGF-BB from cluster 4 in Table 1 and RANTES from cluster 3 of Table 1), and in some instances the AD diagnosis biomarkers are completely diverse (i.e. no two of the selected AD diagnosis biomarkers are from the same cluster). Accordingly, the invention provides a number of different embodiments for diagnosing or aiding in the diagnosis of AD.

TABLE 1

| Cluster | Biomarker |
|---------|-----------|
| 0 | bFGF |
| 1 | TPO |
| 2 | FGF-6 |
|   | IL-3 |
|   | sIL-6 R |
|   | MIP-1d |
|   | sTNF RII |
|   | TNF-b |
| 3 | RANTES |
|   | TIMP-1 |
|   | TIMP-2 |
| 4 | BDNF |
|   | EGF |
|   | LEPTIN(OB) |
|   | MSP-α |
|   | NAP-2 |
|   | NT-3 |
|   | PDGF-BB |
|   | SCF |
|   | TGF-b3 |

In some embodiments, the level of a single AD diagnosis biomarker in a peripheral biological fluid sample is obtained and the measured level is compared to a reference level to diagnose or aid in diagnosing AD. In certain embodiments where measured level for a single AD diagnosis biomarker is obtained for the practice of the invention, the measured level is for RANTES in the peripheral biological fluid sample.

In other embodiments, the levels of at least two AD diagnosis biomarkers in a peripheral biological fluid sample are obtained and compared to reference levels for each of the markers. Accordingly, the invention provides methods for diagnosing and/or aiding in the diagnosis of AD by measuring the levels of at least 2, 3, 4, 5, 6, 7, 8, 9, 10, 11, 12, 15, or 20 AD diagnosis biomarkers and comparing the measured levels with reference levels. Exemplary embodiments utilize 2, 3, 4, or 5 AD diagnosis biomarkers. In some embodiments, provided herein are methods for diagnosing and/or aiding in the diagnosis of AD by measuring the levels of at least Leptin, RANTES, BDGF, and PDGF-BB. In other examples, provided herein are methods, such as for example, for diagnosing and/or aiding in the diagnosis of AD by measuring the levels of at least one biomarker selected from the group consisting of Lymphotactin and IL-11. In other examples, biomarkers comprise Lymphotactin and IL-11. In further examples, an AD diagnosis markers is selected from the group consisting of BTC; SDF-1; MCP-2; IFN-gamma; IGFBP-4; IGF-1SR; IL-8; GM-CSF; and ANG-2, as described in the Examples. In further examples, an AD diagnosis marker is selected from the group consisting of IFN-gamma and IL-8, as described in the Examples. In yet other examples, an AD diagnosis biomarker is selected from the group consisting of biomarkers sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and FGF-6, as described in the Examples. For those embodiments which utilize more than one AD diagnosis biomarker (i.e., those embodiments in which measured values are obtained for more than one AD diagnosis biomarker), exemplary combinations of AD diagnosis biomarkers shown in Table 3 include (1) Leptin in combination with any of the other AD diagnosis biomarkers (i.e., Leptin and BDNF, Leptin and bFGF, Leptin and EGF, Leptin and FGF-6, Leptin and IL-3, Leptin and sIL-6R, Leptin and MIP-1δ, Leptin and MSP-α, Leptin and NAP-2, Leptin and NT-3, Leptin and PDGF-BB, Leptin and RANTES, Leptin and SCF, Leptin and sTNR RII, Leptin and TGF-133, Leptin and TIMP-1, Leptin and TIMP-2, Leptin and TNF-β, and Leptin and TPO), (2) RANTES in combination with any of the other AD diagnosis biomarkers (i.e., RANTES and BDNF, RANTES and bFGF, RANTES and EGF, RANTES and FGF-6, RANTES and IL-3, RANTES and sIL-6R, RANTES and Leptin, RANTES and MIP-1δ, RANTES and MSP-α, RANTES and NAP-2, RANTES and NT-3, RANTES and PDGF-BB, RANTES and SCF, RANTES and sTNR RII, RANTES and TGF-133, RANTES and TIMP-1, RANTES and TIMP-2, RANTES and TNF-β, and RANTES and TPO); (3) PDGF-BB and any of the other AD diagnosis biomarkers (i.e., PDGF-BB and BDNF, PDGF-BB and bFGF, PDGF-BB and EGF, PDGF-BB and FGF-6, PDGF-BB and IL-3, PDGF-BB and sIL-6R, PDGF-BB and Leptin, PDGF-BB and MIP-1δ, PDGF-BB and MSP-α, PDGF-BB and NAP-2, PDGF-BB and NT-3, PDGF-BB and RANTES, PDGF-BB and SCF, PDGF-BB and sTNR RII, PDGF-BB and TGF-β3, PDGF-BB and TIMP-1, PDGF-BB and TIMP-2, PDGF-BB and TNF-β, and PDGF-BB and TPO); (4) BDNF in combination with any of the other AD diagnosis biomarkers (i.e., BDNF and bFGF, BDNF and EGF, BDNF and FGF-6, BDNF and IL-3, BDNF and sIL-6R, BDNF and Leptin, BDNF and MIP-1δ, BDNF and MSP-α, BDNF and NAP-2, BDNF and NT-3, BDNF and PDGF-BB, BDNF and RANTES, BDNF and SCF, BDNF and sTNR RII, BDNF and TGF-β3, BDNF and TIMP-1, BDNF and TIMP-2, BDNF and TNF-β, and BDNF and TPO); (5) RANTES, PDGF-BB, and NT-3; (6) Leptin, PDGF-BB, and RANTES; (7) BDNF, PDGF-BB, and RANTES; (8) BDNF, Leptin, and RANTES; (9) BDNF, Leptin, and PDGF-BB; (10) PDGF-BB, EGF, and NT-3; (11) PDGF-BB, NT 3, and Leptin; (12) BDNF, Leptin, PDGF-BB, RANTES; and (13) RANTES, PDGF-BB, NT-3, EGF, NAP-2, and Leptin. Additional exemplary combinations of AD diagnosis biomarkers include (14) Leptin in combination with any of the other AD diagnosis biomarkers disclosed herein (i.e., Leptin and GCSF, Leptin and IFN-γ, Leptin and IGFBP-1, Leptin and BMP-6, Leptin and BMP-4, Leptin and Eotaxin-2, Leptin and IGFBP-2, Leptin and TARC, Leptin and ANG, Leptin and PARC, Leptin and Acrp30, Leptin and AgRP(ART), Leptin and ICAM-1, Leptin and TRAIL R3, Leptin and uPAR, Leptin and IGFBP-4, Leptin and IL-1Ra, Leptin and AXL, Leptin and FGF-4, Leptin and CNTF, Leptin and MCP-1, Leptin and MIP1b, Leptin and VEGF-B, Leptin and IL-8, Leptin and FAS and Leptin and EGF-R), (15) RANTES in combination with any of the other AD diagnosis biomarkers disclosed herein (i.e., RANTES and GCSF, RANTES and IFN-γ, RANTES and IGFBP-1, RANTES and BMP-6, RANTES and BMP-4, RANTES and Eotaxin-2, RANTES and IGFBP-2, RANTES and TARC, RANTES and ANG, RANTES and PARC, RANTES and Acrp30, RANTES and AgRP(ART), RANTES and ICAM-1, RANTES and TRAIL R3, RANTES and uPAR, RANTES and IGFBP-4, RANTES and IL-1Ra, RANTES and AXL, RANTES and FGF-4, RANTES and CNTF, RANTES and MCP-1, RANTES and MIP1b, RANTES and VEGF-B, RANTES and IL-8, RANTES and FAS and RANTES and EGF-R), (16) PDGF-BB in combination with any of the other AD diagnosis biomarkers disclosed herein (i.e., PDGF-BB and GCSF, PDGF-BB and IFN-γ, PDGF-BB and IGFBP-1, PDGF-BB and BMP-6, PDGF-BB and BMP-4, PDGF-BB and Eotaxin-2, PDGF-BB and IGFBP-2, PDGF-BB and TARC, PDGF-BB and ANG, PDGF-BB and PARC, PDGF-BB and Acrp30, PDGF-BB and AgRP(ART), PDGF-BB and ICAM-1, PDGF-BB and TRAIL R3, PDGF-BB and uPAR, PDGF-BB and IGFBP-4, PDGF-BB and IL-1Ra, PDGF-BB and AXL, PDGF-BB and FGF-4, PDGF-BB and CNTF, PDGF-BB and MCP-1, PDGF-BB and MIP1b, PDGF-BB and VEGF-B, PDGF-BB and IL-8, PDGF-BB and FAS and PDGF-BB and EGF-R), (17) BDNF in combination with any of the other AD diagnosis biomarkers disclosed herein (i.e., BDNF and GCSF, BDNF and IFN-γ, BDNF and IGFBP-1, BDNF and BMP-6, BDNF and BMP-4, BDNF and Eotaxin-2, BDNF and IGFBP-2, BDNF and TARC, BDNF and ANG, BDNF and PARC, BDNF and Acrp30, BDNF and AgRP(ART), BDNF and ICAM-1, BDNF and TRAIL R3, BDNF and uPAR, BDNF and IGFBP-4, BDNF and IL-1Ra, BDNF and AXL, BDNF and FGF-4, BDNF and CNTF, BDNF and MCP-1, BDNF and MIP1b, BDNF and VEGF-B, BDNF and IL-8, BDNF and FAS and BDNF and EGF-R).

Measuring Levels of AD Biomarkers

There are a number of statistical tests for identifying biomarkers which vary significantly between the subsets, including the conventional t test. However, as the number of biomarkers measured increases, it is generally advantageous to use a more sophisticated technique, such as SAM (see Tusher et al., 2001, *Proc. Natl. Acad. Sci. U.S.A.* 98(9):5116-21). Other useful techniques include Tree Harvesting (Hastie et al., *Genome Biology* 2001, 2:research0003.1-0003.12), Self Organizing Maps (Kohonen, 1982b, *Biological Cybernetics* 43(1):59-69), Frequent Item Set (Agrawal et al., 1993 "Mining association rules between sets of items in large databases." In Proc. of the ACM SIGMOD Conference on Management of Data, pages 207-216, Washington, D.C., May 1993), Bayesian networks (Gottardo, Statistical analysis of microarray data, A Bayesian approach. Biostatistics (2001), 1,1, pp 1-37), and the commercially available software packages CART and MARS.

The SAM technique assigns a score to each biomarker on the basis of change in expression relative to the standard deviation of repeated measurements. For biomarkers with scores greater than an adjustable threshold, the algorithm uses permutations of the repeated measurements to estimate the probability that a particular biomarker has been identified by chance (calculated as a "q-value"), or a false positive rate which is used to measure accuracy. The SAM technique can be carried out using publicly available software called Significance Analysis of Microarrays (see www-stat class.stanford.edu/~tibs/clickwrap/sam.html).

A biomarkers is considered "identified" as being useful for aiding in the diagnosis, diagnosis, stratification, monitoring, and/or prediction of neurological disease when it is significantly different between the subsets of peripheral biological samples tested. Levels of a biomarker are "significantly different" when the probability that the particular biomarker has been identified by chance is less than a predetermined value. The method of calculating such probability will depend on the exact method utilizes to compare the levels between the subsets (e.g., if SAM is used, the q-value will give the probability of misidentification, and the p value will give the probability if the t test (or similar statistical analysis) is used). As will be understood by those in the art, the predetermined value will vary depending on the number of biomarkers measured per sample and the number of samples utilized. Accordingly, predetermined value may range from as high as 50% to as low as 20, 10, 5, 3, 2, or 1%.

As described herein, the level of at least one AD diagnosis biomarker is measured in a biological sample from an individual. The AD biomarker level(s) may be measured using any available measurement technology that is capable of specifically determining the level of the AD biomarker in a biological sample. The measurement may be either quantitative or qualitative, so long as the measurement is capable of indicating whether the level of the AD biomarker in the peripheral biological fluid sample is above or below the reference value.

The measured level may be a primary measurement of the level a particular biomarker a measurement of the quantity of biomarker itself (quantitative data, such as in Example 7), such as by detecting the number of biomarker molecules in the sample) or it may be a secondary measurement of the biomarker (a measurement from which the quantity of the biomarker can be but not necessarily deduced (qualitative data, such as Example 4), such as a measure of enzymatic activity (when the biomarker is an enzyme) or a measure of mRNA coding for the biomarker). Qualitative data may also be derived or obtained from primary measurements.

Although some assay formats will allow testing of peripheral biological fluid samples without prior processing of the sample, it is expected that most peripheral biological fluid samples will be processed prior to testing. Processing generally takes the form of elimination of cells (nucleated and non-nucleated), such as erythrocytes, leukocytes, and platelets in blood samples, and may also include the elimination of certain proteins, such as certain clotting cascade proteins from blood. In some examples, the peripheral biological fluid sample is collected in a container comprising EDTA. See Example 12 for additional sample collection procedures. Commonly, AD biomarker levels will be measured using an affinity-based measurement technology. "Affinity" as relates to an antibody is a term well understood in the art and means the extent, or strength, of binding of antibody to the binding partner, such as an AD diagnosis biomarker as described herein (or epitope thereof). Affinity may be measured and/or expressed in a number of ways known in the art, including, but not limited to, equilibrium dissociation constant ($K_D$ or $K_d$), apparent equilibrium dissociation constant ($K_D'$ or $K_d'$), and $IC_{50}$ (amount needed to effect 50% inhibition in a competition assay; used interchangeably herein with "$I_{50}$"). It is understood that, for purposes of this invention, an affinity is an average affinity for a given population of antibodies which bind to an epitope. Values of $K_D'$ reported herein in terms of mg IgG per ml or mg/ml indicate mg Ig per ml of serum, although plasma can be used.

Affinity-based measurement technology utilizes a molecule that specifically binds to the AD biomarker being measured (an "affinity reagent," such as an antibody or aptamer), although other technologies, such as spectroscopy-based technologies (e.g., matrix-assisted laser desorption ionization-time of flight, or MALDI-TOF, spectroscopy) or assays measuring bioactivity (e.g., assays measuring mitogenicity of growth factors) may be used.

Affinity-based technologies include antibody-based assays (immunoassays) and assays utilizing aptamers (nucleic acid molecules which specifically bind to other molecules), such as ELONA. Additionally, assays utilizing both antibodies and aptamers are also contemplated (e.g., a sandwich format assay utilizing an antibody for capture and an aptamer for detection).

If immunoassay technology is employed, any immunoassay technology which can quantitatively or qualitatively measure the level of a AD biomarker in a biological sample may be used. Suitable immunoassay technology includes radioimmunoassay, immunofluorescent assay, enzyme immunoassay, chemiluminescent assay, ELISA, immuno-PCR, and western blot assay.

Likewise, aptamer-based assays which can quantitatively or qualitatively measure the level of a AD biomarker in a biological sample may be used in the methods of the invention. Generally, aptamers may be substituted for antibodies in nearly all formats of immunoassay, although aptamers allow additional assay formats (such as amplification of bound aptamers using nucleic acid amplification technology such as PCR (U.S. Pat. No. 4,683,202) or isothermal amplification with composite primers (U.S. Pat. Nos. 6,251,639 and 6,692,918).

A wide variety of affinity-based assays are known in the art. Affinity-based assays will utilize at least one epitope derived from the AD biomarker of interest, and many affinity-based assay formats utilize more than one epitope (e.g., two or more epitopes are involved in "sandwich" format assays; at least one epitope is used to capture the marker, and at least one different epitope is used to detect the marker).

Affinity-based assays may be in competition or direct reaction formats, utilize sandwich-type formats, and may further be heterogeneous (e.g., utilize solid supports) or homogenous (e.g., take place in a single phase) and/or utilize or immunoprecipitation. Most assays involve the use of labeled affinity reagent (e.g., antibody, polypeptide, or aptamer); the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA and ELONA assays. Herein, the examples referred to as "quantitative data" the biomarker concentrations were obtained using ELISA. Either of the biomarker or reagent specific for the biomarker can be attached to a surface and levels can be measured directly or indirectly.

In a heterogeneous format, the assay utilizes two phases (typically aqueous liquid and solid). Typically an AD biomarker-specific affinity reagent is bound to a solid support to facilitate separation of the AD biomarker from the bulk of the biological sample. After reaction for a time sufficient to allow for formation of affinity reagent/AD biomarker complexes, the solid support or surface containing the antibody is typically washed prior to detection of bound polypeptides. The affinity reagent in the assay for measurement of AD biomarkers may be provided on a support (e.g., solid or semi-solid); alternatively, the polypeptides in the sample can be immobilized on a support or surface. Examples of supports that can be used are nitrocellulose (e.g., in membrane or microtiter well form), polyvinyl chloride (e.g., in sheets or microtiter wells), polystyrene latex (e.g., in beads or microtiter plates), polyvinylidine fluoride, diazotized paper, nylon membranes, activated beads, glass and Protein A beads. Both standard and competitive formats for these assays are known in the art. Accordingly, provided herein are complexes comprising at least one AD diagnosis biomarker bound to a reagent specific for the biomarker, wherein said reagent is attached to a surface. Also provided herein are complexs comprising at least one AD diagnosis biomarker bound to a reagent specific for the biomarker, wherein said biomarker is attached to a surface.

Array-type heterogeneous assays are suitable for measuring levels of AD biomarkers when the methods of the invention are practiced utilizing multiple AD biomarkers. Array-type assays used in the practice of the methods of the invention will commonly utilize a solid substrate with two or more capture reagents specific for different AD biomarkers bound to the substrate a predetermined pattern (e.g., a grid). The peripheral biological fluid sample is applied to the substrate and AD biomarkers in the sample are bound by the capture reagents. After removal of the sample (and appropriate washing), the bound AD biomarkers are detected using a mixture of appropriate detection reagents that specifically bind the various AD biomarkers. Binding of the detection reagent is commonly accomplished using a visual system, such as a fluorescent dye-based system. Because the capture reagents are arranged on the substrate in a predetermined pattern, array-type assays provide the advantage of detection of multiple AD biomarkers without the need for a multiplexed detection system.

In a homogeneous format the assay takes place in single phase (e.g., aqueous liquid phase). Typically, the biological sample is incubated with an affinity reagent specific for the AD biomarker in solution. For example, it may be under conditions that will precipitate any affinity reagent/antibody complexes which are formed. Both standard and competitive formats for these assays are known in the art.

In a standard (direct reaction) format, the level of AD biomarker/affinity reagent complex is directly monitored. This may be accomplished by, for example, determining the amount of a labeled detection reagent that forms is bound to AD biomarker/affinity reagent complexes. In a competitive format, the amount of AD biomarker in the sample is deduced by monitoring the competitive effect on the binding of a known amount of labeled AD biomarker (or other competing ligand) in the complex. Amounts of binding or complex formation can be determined either qualitatively or quantitatively.

The methods described in this patent may be implemented using any device capable of implementing the methods. Examples of devices that may be used include but are not limited to electronic computational devices, including computers of all types. When the methods described in this patent are implemented in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods may also be provided over an electronic network, for example, over the internet, world wide web, an intranet, or other network.

In one example, the methods described in this patent may be implemented in a system comprising a processor and a computer readable medium that includes program code means for causing the system to carry out the steps of the methods described in this patent. The processor may be any processor capable of carrying out the operations needed for implementation of the methods. The program code means may be any code that when implemented in the system can cause the system to carry out the steps of the methods described in this patent. Examples of program code means include but are not limited to instructions to carry out the methods described in this patent written in a high level computer language such as C++, Java, or Fortran; instructions to carry out the methods described in this patent written in a low level computer language such as assembly language; or instructions to carry out the methods described in this patent in a computer executable form such as compiled and linked machine language.

Complexes formed comprising AD biomarker and an affinity reagent are detected by any of a number of known techniques known in the art, depending on the format of the assay and the preference of the user. For example, unlabelled affinity reagents may be detected with DNA amplification technology (e.g., for aptamers and DNA-labeled antibodies) or labeled "secondary" antibodies which bind the affinity reagent. Alternately, the affinity reagent may be labeled, and the amount of complex may be determined directly (as for dye—(fluorescent or visible), bead-, or enzyme-labeled affinity reagent) or indirectly (as for affinity reagents "tagged" with biotin, expression tags, and the like). Herein the examples provided referred to as "qualitative data" filter based antibody arrays using chemiluminesense were used to obtain measurements for biomarkers.

As will be understood by those of skill in the art, the mode of detection of the signal will depend on the exact detection system utilized in the assay. For example, if a radiolabeled detection reagent is utilized, the signal will be measured using a technology capable of quantitating the signal from the biological sample or of comparing the signal from the biological sample with the signal from a reference sample, such as scintillation counting, autoradiography (typically combined with scanning densitometry), and the like. If a chemiluminescent detection system is used, then the signal will typically be detected using a luminometer. Methods for detecting signal from detection systems are well known in the art and need not be further described here.

When more than one AD biomarker is measured, the biological sample may be divided into a number of aliquots, with separate aliquots used to measure different AD biomarkers (although division of the biological sample into multiple aliquots to allow multiple determinations of the levels of the AD biomarker in a particular sample are also contemplated). Alternately the biological sample (or an aliquot therefrom) may be tested to determine the levels of multiple AD biomarkers in a single reaction using an assay capable of measuring the individual levels of different AD biomarkers in a single assay, such as an array-type assay or assay utilizing multiplexed detection technology (e.g., an assay utilizing detection reagents labeled with different fluorescent dye markers).

It is common in the art to perform 'replicate' measurements when measuring biomarkers. Replicate measurements are ordinarily obtained by splitting a sample into multiple aliquots, and separately measuring the biomarker(s) in separate reactions of the same assay system. Replicate measurements are not necessary to the methods of the invention, but many embodiments of the invention will utilize replicate testing, particularly duplicate and triplicate testing.

Reference Levels

The reference level used for comparison with the measured level for a AD biomarker may vary, depending on aspect of the invention being practiced, as will be understood from the foregoing discussion. For AD diagnosis methods, the "reference level" is typically a predetermined reference level, such as an average of levels obtained from a population that is not afflicted with AD or MCI, but in some instances, the reference level can be a mean or median level from a group of individuals including AD patients. In some instances, the predetermined reference level is derived from (e.g., is the mean or median of) levels obtained from an age-matched population. In some examples disclosed herein, the age-matched population comprises individuals with non-AD neurodegenerative disorders. See Examples 11 and 12.

For MCI diagnosis methods (i.e., methods of diagnosing or aiding in the diagnosis of MCI), the reference level is typically a predetermined reference level, such as an average of levels obtained from a population that is not afflicted with AD or MCI, but in some instances, the reference level can be a mean or median level from a group of individuals including MCI and/or AD patients. In some instances, the predetermined reference level is derived from (e.g., is the mean or median of) levels obtained from an age-matched population.

For AD monitoring methods (e.g., methods of diagnosing or aiding in the diagnosis of AD progression in an AD patient), the reference level may be a predetermined level, such as an average of levels obtained from a population that is not afflicted with AD or MCI, a population that has been diagnosed with MCI or AD, and, in some instances, the reference level can be a mean or median level from a group of individuals including MCI and/or AD patients. Alternately, the reference level may be a historical reference level for the particular patient (e.g., a Leptin level that was obtained from a sample derived from the same individual, but at an earlier point in time). In some instances, the predetermined reference level is derived from (e.g., is the mean or median of) levels obtained from an age-matched population.

For AD stratification methods (i.e., methods of stratifying AD patients into mild, moderate and severe stages of AD), the reference level is normally a predetermined reference level that is the mean or median of levels from a population which has been diagnosed with AD or MCI (preferably a population diagnosed with AD) In some instances, the predetermined reference level is derived from (e.g., is the mean or median of) levels obtained from an age-matched population.

Age-matched populations (from which reference values may be obtained) are ideally the same age as the individual being tested, but approximately age-matched populations are also acceptable. Approximately age-matched populations may be within 1, 2, 3, 4, or 5 years of the age of the individual tested, or may be groups of different ages which encompass the age of the individual being tested. Approximately age-matched populations may be in 2, 3, 4, 5, 6, 7, 8, 9, or year increments (e.g. a "5 year increment" group which serves as the source for reference values for a 62 year old individual might include 58-62 year old individuals, 59-63 year old individuals, 60-64 year old individuals, 61-65 year old individuals, or 62-66 year old individuals).

Comparing Levels of AD Biomarkers

The process of comparing a measured value and a reference value can be carried out in any convenient manner appropriate to the type of measured value and reference value for the AD biomarker at issue. As discussed above, 'measuring' can be performed using quantitative or qualitative measurement techniques, and the mode of comparing a measured value and a reference value can vary depending on the measurement technology employed. For example, when a qualitative colorimetric assay is used to measure AD biomarker levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values (e.g., quantitative measurements of concentration, such as nanograms of AD biomarker per milliliter of sample, or absolute amount). In other examples, measured values are qualitative. As with qualitative measurements, the comparison can be made by inspecting the numerical data, by inspecting representations of the data (e.g., inspecting graphical representations such as bar or line graphs).

A measured value is generally considered to be substantially equal to or greater than a reference value if it is at least 95% of the value of the reference value (e.g., a measured value of 1.71 would be considered substantially equal to a reference value of 1.80). A measured value is considered less than a reference value if the measured value is less than 95% of the reference value (e.g., a measured value of 1.7 would be considered less than a reference value of 1.80). A measured value is considered more than a reference value if the measured value is at least more than 5% greater than the reference value (e.g., a measured value of 1.89 would be considered more than a reference value of 1.80).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for an AD biomarker. Alternately, a separate device (e.g., a digital computer) may be used to compare the measured value(s) and the reference value(s). Automated devices for comparison may include stored reference values for the AD biomarker(s) being measured, or they may compare the measured value(s) with reference values that are derived from contemporaneously measured reference samples.

In some embodiments, the methods of the invention utilize 'simple' or 'binary' comparison between the measured level(s) and the reference level(s) (e.g., the comparison between a measured level and a reference level determines whether the measured level is higher or lower than the reference level). For AD diagnosis biomarkers, a comparison showing that the measured value for the biomarker is lower than the reference value indicates or suggests a diagnosis of AD. For methods relating to the diagnosis of MCI, a comparison showing that measured value for RANTES is lower than the reference value indicates or suggests a diagnosis of AD. In those embodiments relating to diagnosis of MCI which additionally utilize a measured value for Leptin, a comparison showing that RANTES is less than the reference value while Leptin is substantially equal to or greater than the reference level suggests or indicates a diagnosis of MCI.

As described herein, biological fluid samples may be measured quantitatively (absolute values) or qualitatively (relative values). The respective AD biomarker levels for a given assessment may or may not overlap. As described herein, for some embodiments, qualitative data indicate a given level of cognitive impairment (mild, moderate or severe AD) (which can be measured by MMSE scores) and in other embodiments, quantitative data indicate a given level of cognitive impairment. As shown in Example 4 and under the conditions provided in Example 4 (qualitative data), in those embodiments relating to stratification of AD, a comparison which shows BDNF levels lower than the reference level suggests or indicates mild AD, while a comparison which shows BDNF levels higher than the reference level suggests more advanced AD (i.e., moderate or severe AD), and amongst those samples with BDNF levels higher than the reference level, those also having PDGF-BB levels below the reference level suggest or indicate moderate AD, while those samples also having PDGF-BB levels above the reference level suggest or indicate severe AD. In those embodiments relating to stratification of AD shown in Example 7 (quantitative data), a comparison which shows BDNF levels lower than the reference level where the reference level is Normal suggests or indicates mild AD, while a comparison which shows BDNF levels lower than the reference level where the reference level is Mild AD suggests more advanced AD (i.e., moderate, severe AD), while those samples with leptin levels equal to the reference level where the reference level is Mild AD, those having RANTES levels below the reference level suggest or indicate moderate AD, while those samples with leptin levels equal to the reference level where the reference level is Moderate AD those having PDGF-BB, RANTES, or BDNF levels lower than the reference level suggest or indicate severe AD.

However, in certain aspects of the invention, the comparison is performed to determine the magnitude of the difference between the measured and reference values (e.g., comparing the 'fold' or percentage difference between the measured value and the reference value). A fold difference that is about equal to or greater than the minimum fold difference disclosed herein suggests or indicates a diagnosis of AD, MCI, progression from MCI to AD, or progression from mild AD to moderate AD, as appropriate to the particular method being practiced. A fold difference can be determined by measuring the absolute concentration of a protein and comparing that to the absolute value of a reference, or a fold difference can be measured by the relative difference between a reference value and a sample value, where neither value is a measure of absolute concentration, and/or where both values are measured simultaneously. A fold difference and be in the range of 10% to 95%. An ELISA measures the absolute content or concentration of a protein from which a fold change is determined in comparison to the absolute concentration of the same protein in the reference. An antibody array measures the relative concentration from which a fold change is determined. Accordingly, the magnitude of the difference between the measured value and the reference value that suggests or indicates a particular diagnosis will depend on the particular AD biomarker being measured to produce the measured value and the reference value used (which in turn depends on the method being practiced). Tables 2A-2B list minimum fold difference values for AD biomarkers for use in methods of the invention which utilize a fold difference in making the comparison between the measured value and the reference value. In those embodiments utilizing fold difference values, a fold difference of about the fold difference indicated in Table 2A suggests a diagnosis of AD, wherein the fold change is a negative value. For example, as described herein, BDNF levels (as measured by ELISA) are decreased in AD patients with mild AD, and BDNF levels decrease further as the severity of the AD intensifies. As shown in Table 6, a BDNF fold change of −46% means a reduction of BDNF levels by 46%. As shown in Table 2A, for qualitative measurements using antibodies, a BDNF fold change of 0.60 means a reduction in BDNF levels by about 60%. Table 2B provides additional information regarding fold changes.

TABLE 2A

| Biomarker | Fold Change (as negative value or decrease) |
|---|---|
| BDNF | 0.60 |
| bFGF | 0.75 |
| EGF | 0.60 |
| FGF-6 | 0.70 |
| IL-3 | 0.80 |
| sIL-6 R | 0.75 |
| Leptin | 0.55 |
| MIP-1δ | 0.60 |
| MSP-α | 0.80 |
| NAP-2 | 0.75 |
| NT-3 | 0.75 |
| PDGF-BB | 0.60 |
| RANTES | 0.75 |
| SCF | 0.80 |
| sTNF RII | 0.75 |
| TGF-β3 | 0.80 |
| TIMP-1 | 0.75 |
| TIMP-2 | 0.80 |
| TNF-β | 0.70 |
| TPO | 0.75 |

TABLE 2B

| Protein | Relative Fold Change (n = 51) | q-value | Absolute Fold Change (n = 187) | p-value |
|---|---|---|---|---|
| MIP-1d | −0.54291 | 0.0165 | | |
| PDGF-BB | −0.53687 | 0.0165 | −0.135 | 0.891 |
| LEPTIN(OB) | −0.47625 | 0.0165 | −0.357 | 0.0018 |
| IL-6 R | −0.6763 | 0.0165 | | |
| BDNF | −0.53628 | 0.0165 | −0.355 | 0.0006 |
| TIMP-1 | −0.71622 | 0.0165 | | |
| RANTES | −0.68299 | 0.0165 | −0.184 | 0.0144 |
| EGF | −0.56182 | 0.0165 | | |
| TIMP-2 | −0.75011 | 0.0165 | | |
| NAP-2 | −0.67257 | 0.0165 | | |
| sTNF RII | −0.70029 | 0.0165 | | |
| TNF-b | −0.64998 | 0.0165 | | |
| TPO | −0.71405 | 0.0165 | | |
| FGF-6 | −0.66467 | 0.0165 | | |
| NT-3 | −0.69805 | 0.0165 | | |
| bFGF | −0.67351 | 0.0165 | | |
| IL-3 | −0.75802 | 0.0165 | | |
| SCF | −0.73041 | 0.0165 | | |
| TGF-b3 | −0.76912 | 0.0165 | | |
| MSP-a | −0.76466 | 0.0165 | | |

As will be apparent to those of skill in the art, when replicate measurements are taken for the biomarker(s) tested, the measured value that is compared with the reference value is a value that takes into account the replicate measurements. The replicate measurements may be taken into account by using either the mean or median of the measured values as the "measured value."

Screening Prospective Agents for AD Biomarker Modulation Activity

The invention also provides methods of screening for candidate agents for the treatment of AD and/or MCI by assaying prospective candidate agents for activity in modulating AD biomarkers. The screening assay may be performed either in vitro and/or in vivo. Candidate agents identified in the screening methods described herein may be useful as therapeutic agents for the treatment of AD and/or MCI.

The screening methods of the invention utilize the AD biomarkers described herein and AD biomarker polynucleotides as "drug targets." Prospective agents are tested for activity in modulating a drug target in an assay system. As will be understood by those of skill in the art, the mode of testing for modulation activity will depend on the AD biomarker and the form of the drug target used (e.g., protein or gene). A wide variety of suitable assays are known in the art.

When the AD biomarker protein itself is the drug target, prospective agents are tested for activity in modulating levels or activity of the protein itself. Modulation of levels of an AD biomarker can be accomplished by, for example, increasing or reducing half-life of the biomarker protein. Modulation of activity of an AD biomarker can be accomplished by increasing or reducing the availability of the AD biomarker to bind to its cognate receptor(s) or ligand(s).

When an AD biomarker polynucleotide is the drug target, the prospective agent is tested for activity in modulating synthesis of the AD biomarker. The exact mode of testing for modulatory activity of a prospective agent will depend, of course, on the form of the AD biomarker polynucleotide selected for testing. For example, if the drug target is an AD biomarker polynucleotide, modulatory activity is typically tested by measuring either mRNA transcribed from the gene (transcriptional modulation) or by measuring protein produced as a consequence of such transcription (translational modulation). As will be understood by those in the art, many assay formats will utilize a modified form of the AD biomarker gene where a heterologous sequence (e.g., encoding an expression marker such as an enzyme or an expression tag such as oligo-histidine or a sequence derived from another protein, such as myc) is fused to (or even replaces) the sequence encoding the AD biomarker protein. Such heterologous sequence(s) allow for convenient detection of levels of protein transcribed from the drug target.

Prospective agents for use in the screening methods of the invention may be chemical compounds and/or complexes of any sort, including both organic and inorganic molecules (and complexes thereof). As will be understood in the art, organic molecules are most commonly screened for AD biomarker modulatory activity. In some situations, the prospective agents for testing will exclude the target AD biomarker protein.

Screening assays may be in any format known in the art, including cell-free in vitro assays, cell culture assays, organ culture assays, and in vivo assays (i.e., assays utilizing animal models of AD and MCI). Accordingly, the invention provides a variety of embodiments for screening prospective agents to identify candidate agents for the treatment of AD and/or MCI.

In some embodiments, prospective agents are screened to identify candidate agents for the treatment of AD and/or MCI in a cell-free assay. Each prospective agent is incubated with the drug target in a cell-free environment, and modulation of the AD biomarker is measured. Cell-free environments useful in the screening methods of the invention include cell lysates (particularly useful when the drug target is an AD biomarker gene) and biological fluids such as whole blood or fractionated fluids derived therefrom such as plasma and serum (particularly useful when the AD biomarker protein is the drug target). When the drug target is an AD biomarker gene, the modulation measured may be modulation of transcription or translation. When the drug target is the AD biomarker protein, the modulation may of the half-life of the protein or of the availability of the AD biomarker protein to bind to its cognate receptor or ligand.

In other embodiments, prospective agents are screened to identify candidate agents for the treatment of AD and/or MCI in a cell-based assay. Each prospective agent is incubated with cultured cells, and modulation of target AD biomarker is measured. In certain embodiments, the cultured cells are astrocytes, neuronal cells (such as hippocampal neurons), fibroblasts, or glial cells. When the drug target is an AD biomarker gene, transcriptional or translational modulation may be measured. When the drug target is the AD biomarker protein, the AD biomarker protein is also added to the assay mixture, and modulation of the half-life of the protein or of the availability of the AD biomarker protein to bind to its cognate receptor or ligand is measured.

Further embodiments relate to screening prospective agents to identify candidate agents for the treatment of AD and/or MCI in organ culture-based assays. In this format, each prospective agent is incubated with either a whole organ or a portion of an organ (such as a portion of brain tissue, such as a brain slice) derived from a non-human animal and modulation of the target AD biomarker is measured. When the drug target is an AD biomarker gene, transcriptional or translational modulation may be measured. When the drug target is the AD biomarker protein, the AD biomarker protein is also added to the assay mixture, and modulation of the half-life of the protein or of the availability of the AD biomarker protein to bind to its cognate receptor is measured.

Additional embodiments relate to screening prospective agents to identify candidate agents for the treatment of AD and/or MCI utilizing in vivo assays. In this format, each prospective agent is administered to a non-human animal and modulation of the target AD biomarker is measured. Depending on the particular drug target and the aspect of AD and/or MCI treatment that is sought to be addressed, the animal used in such assays may either be a "normal" animal (e.g., C57 mouse) or an animal which is a model of AD or MCI. A number of animal models of AD are known in the art, including the 3xTg-AD mouse (Oddo, S et al., 2003, *Neuron* 39(3): 409-21), mice over expressing human amyloid beta precursor protein (APP) and presenilin genes (Citron, M et al., 1997, *Nat. Med.* 3(1):67-72), and others (see Higgins et al., 2003, *Behav. Pharmacol.* 14(5-6):419-38). When the drug target is an AD biomarker gene, transcriptional or translational modulation may be measured. When the drug target is the AD biomarker protein, modulation of the half-life of the target AD biomarker or of the availability of the AD biomarker protein to bind to its cognate receptor or ligand is measured. The exact mode of measuring modulation of the target AD biomarker will, of course, depend on the identity of the AD biomarker, the format of the assay, and the preference of the practitioner. A wide variety of methods are known in the art for measuring modulation of transcription, translation, protein half-life, protein availability, and other aspects which can be measured. In view of the common knowledge of these techniques, they need not be further described here.

Kits

The invention provides kits for carrying out any of the methods described herein. Kits of the invention may comprise at least one reagent specific for an AD biomarker, and may further include instructions for carrying out a method described herein. Kits may also comprise AD biomarker reference samples, that is, useful as reference values. Kits comprise any biomarker and/or sets of biomarkers as described herein. "AD diagnosis markers" for use in kits provided herein include, but are not limited to GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In other examples, "AD diagnosis biomarkers" for use in kits provided herein include but are not limited to basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β). In other examples, kits comprise any one, two, three or four of the AD diagnosis markers Leptin, RANTES, PDFG-BB and BDNF. In other examples, "AD diagnosis biomarkers" for use in kits provided herein include but are not limited to at least one biomarker selected from the group consisting of the biomarkers listed in Tables 9A1-9A2 and 9B that are significantly increased (9A1-9A2) or decreased (9B) in AD compared to age-matched normal controls plus other non-AD forms of neurodegeneration, such as for example PD and PN (that is, as compared to all controls). In some examples, any one or more of the biomarkers listed in Tables 9A1-9A2 and 9B, that is reagents specific for the biomarkers, can be used in kits for use in the methods as disclosed herein, including for example, methods to diagnose AD, or to diagnose AD as distinguished from other non-AD neurodegenerative diseases or disorders, such as for example PD and PN.

Tables 10A1-10A2 and 10B provide a listing of biomarkers that are significantly increased (10A1-10A2) or decreased (10B) in AD compared to healthy age-matched controls. Any one or more of the biomarkers listed in Tables 10A1-10A2 and 10B, that is, reagents specific for the biomarker, can be used in kits for use in the methods disclosed herein, such as for example, for aiding in the diagnosis of or diagnosing AD. In some examples, biomarkers are selected for use in methods disclosed herein, for aiding in the diagnosis of or diagnosing AD that have a p-value of equal to or less than 0.05, (or a q-value (%) of equal to or less than 5.00). Tables 11A1-11A2 and 11B provide a listing of biomarkers that are significantly increased (11A1-11A2) or decreased (11B) in AD compared to age-matched degenerative controls. Any one or more of the biomarkers listed in Tables 11A1-11A2 and 11B, that is, reagents specific for the biomarker, can be used in kits for use in the methods disclosed herein, such as for example, for aiding in the diagnosis of or diagnosing AD.

Tables 12A-12B provide a listing of biomarkers that are significantly increased (12A) or decreased (12B) in AD plus other non-AD degenerative controls with reference to age matched controls. Any one or more of the biomarkers listed in Tables 12A-12B, that is, reagents specific for the biomarker, can be used in kits for use in the methods disclosed herein, such as for example, for aiding in the diagnosis of or diagnosing neurodegenerative diseases, including AD. In further examples, kits comprise reagents specific for Lymphotactin and/or IL-11; and/or reagents specific for BTC; SDF-1; MCP-2; IFN-gamma; IGFBP-4; IGF-1SR; IL-8; GM-CSF; and/or ANG-2; and/or reagents specific for IFN-gamma and/or IL-8, and/or reagents specific for sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and/or FGF-6. In additional examples, a kit comprises at least one AD diagnosis biomarker for use in normalizing data from experiments. In some examples, a kit comprises at least one of TGF-beta and TGF-beta 3 for use in normalizing data and in other examples, a kit comprises both TGF-beta and TGF-beta 3 for use in normalizing data. More commonly, kits of the invention comprise at least two different AD biomarker-specific affinity reagents, where each reagent is specific for a different AD biomarker. In some embodiments, kits comprise at least 3, at least 4, at least 5, at least 6, at least 7, at least 8, at least 9, or at least 10 reagents specific for an AD biomarker. In some embodiments, the reagent(s) specific for an AD biomarker is an affinity reagent.

Kits comprising a single reagent specific for an AD biomarker will generally have the reagent enclosed in a container (e.g., a vial, ampoule, or other suitable storage container), although kits including the reagent bound to a substrate (e.g., an inner surface of an assay reaction vessel) are also contemplated. Likewise, kits including more than one reagent may also have the reagents in containers (separately or in a mixture) or may have the reagents bound to a substrate.

In some embodiments, the AD biomarker-specific reagent(s) will be labeled with a detectable marker (such as a fluorescent dye or a detectable enzyme), or be modified to facilitate detection (e.g., biotinylated to allow for detection with a avidin- or streptavidin-based detection system). In other embodiments, the AD biomarker-specific reagent will not be directly labeled or modified.

Certain kits of the invention will also include one or more agents for detection of bound AD biomarker-specific reagent. As will be apparent to those of skill in the art, the identity of the detection agents will depend on the type of AD biomarker-specific reagent(s) included in the kit, and the intended detection system. Detection agents include antibodies specific for the AD biomarker-specific reagent (e.g., secondary antibodies), primers for amplification of an AD biomarker-specific reagent that is nucleotide based (e.g., aptamer) or of a nucleotide 'tag' attached to the AD biomarker-specific reagent, avidin- or streptavidin-conjugates for detection of biotin-modified AD biomarker-specific reagent(s), and the like. Detection systems are well known in the art, and need not be further described here. Accordingly, provided herein are kits for identifying an individual with mild cognitive impairment (MCI), comprising at least one reagent specific for RANTES; and instructions for carrying out the method. In some examples, the kits further comprise a reagent specific for leptin. In other examples, provided herein are kits for monitoring progression of Alzheimer's disease (AD) in an AD patient, comprising at least one reagent specific for leptin; and instructions for carrying out the method. Also provided herein are kits for stratifying an Alzheimer's disease (AD) patient, comprising at least one reagent specific for brain derived neurotrophic factor (BDNF); at least one reagent specific for BB homodimeric platelet derived growth factor (PDGF-BB); and instructions for carrying out the method.

A modified substrate or other system for capture of AD biomarkers may also be included in the kits of the invention, particularly when the kit is designed for use in a sandwich-format assay. The capture system may be any capture system useful in an AD biomarker assay system, such as a multi-well plate coated with an AD biomarker-specific reagent, beads coated with an AD biomarker-specific reagent, and the like. Capture systems are well known in the art and need not be further described here.

In certain embodiments, kits for use in the methods disclosed herein include the reagents in the form of an array. The array includes at least two different reagents specific for AD biomarkers (each reagent specific for a different AD biomarker) bound to a substrate in a predetermined pattern (e.g., a grid). Accordingly, the present invention provides arrays comprising "AD diagnosis markers" including, but not limited to GCSF; IFN-g; IGFBP-1; BMP-6; BMP-4; Eotaxin-2; IGFBP-2; TARC; RANTES; ANG; PARC; Acrp30; AgRP (ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. In other examples, "AD diagnosis biomarkers" include but are not limited to basic fibroblast growth factor (bFGF), BB homodimeric platelet derived growth factor (PDGF-BB), brain derived neurotrophic factor (BDNF), epidermal growth factor (EGF), fibroblast growth factor 6 (FGF-6), interleukin-3 (IL-3), soluble interleukin-6 receptor (sIL-6R), Leptin (also known as ob), macrophage inflammatory protein-1 delta (MIP-1δ), macrophage stimulating protein alpha chain (MSP-α), neurotrophin-3 (NT-3), neutrophil activating peptide-2 (NAP-2), RANTES, soluble tumor necrosis factor receptor-2 (sTNF RII), stem cell factor (SCF), thrombopoietin (TPO), tissue inhibitor of metalloproteases-1 (TIMP-1), tissue inhibitor of metalloproteases-2 (TIMP-2), transforming growth factor-beta 3 (TGF-β3), tumor necrosis factor beta (TNF-β). In other examples, arrays comprise any one, two, three or four of the AD diagnosis markers Leptin, RANTES, PDFG-BB and BDNF. Other examples of markers and sets of markers are described herein. The localization of the different AD biomarker-specific reagents (the "capture reagents") allows measurement of levels of a number of different AD biomarkers in the same reaction. Kits including the reagents in array form are commonly in a sandwich format, so such kits may also comprise detection reagents. Normally, the kit will include different detection reagents, each detection reagent specific to a different AD biomarker. The detection reagents in such embodiments are normally reagents specific for the same AD biomarkers as the reagents bound to the substrate (although the detection reagents typically bind to a different portion or site on the AD biomarker target than the substrate-bound reagents), and are generally affinity-type detection reagents. As with detection reagents for any other format assay, the detection reagents may be modified with a detectable moiety, modified to allow binding of a separate detectable moiety, or be unmodified. Array-type kits including detection reagents that are either unmodified or modified to allow binding of a separate detectable moiety may also contain additional detectable moieties (e.g., detectable moieties which bind to the detection reagent, such as labeled antibodies which bind unmodified detection reagents or streptavidin modified with a detectable moiety for detecting biotin-modified detection reagents).

The instructions relating to the use of the kit for carrying out the invention generally describe how the contents of the kit are used to carry out the methods of the invention. Instructions may include information as sample requirements (e.g., form, pre-assay processing, and size), steps necessary to measure the AD biomarker(s), and interpretation of results.

Instructions supplied in the kits of the invention are typically written instructions on a label or package insert (e.g., a paper sheet included in the kit), but machine-readable instructions (e.g., instructions carried on a magnetic or optical storage disk) are also acceptable. In certain embodiments, machine-readable instructions comprise software for a programmable digital computer for comparing the measured values obtained using the reagents included in the kit.

The following Examples are provided to illustrate the invention, but are not intended to limit the scope of the invention in any way.

EXAMPLES

Example 1

AD Diagnosis Biomarkers

We compared plasma protein expression levels for 120 proteins in 32 cases of serum collected from patients with Alzheimer's Disease (with a mean age of 74) to 19 cases of serum collected from control subjects (also with mean age of 74). Alzheimer's Disease subjects were clinically diagnosed with AD by a neurologist, and had Mini Mental State Exam (MMSE) scores ranging from 26-14.

Plasma samples were assayed using a sandwich-format ELISA on a nitrocellulose filter substrate. Plasma samples were diluted 1:10 in phosphate buffer and incubated with the capture substrate (a nitrocellulose membrane spotted with capture antibodies). The samples were incubated with the capture substrate for two hours at room temperature, then decanted from the capture substrate. The substrate was washed twice with 2 ml of washing buffer (1×PBS; 0.05% Tween-20) at room temp, then incubated with biotinylated detection antibodies for two hours at room temperature. The capture antibody solution was decanted and the substrate was washed twice for 5 min with washing buffer. The washed substrate was then incubated with horseradish peroxidase/streptavidin conjugate for 45 minutes, at which time the conjugate solution was decanted and the membranes were washed with washing buffer twice for 5 minutes. The substrate was transferred onto a piece of filter paper, incubated in enhanced chemiluminescence (ECL) Detection Buffer solution purchased from Raybiotech, Inc. Chemiluminescence was detected and quantified with a chemiluminescence imaging camera. Signal intensities were normalized to standard proteins blotted on the substrate and used to calculate relative levels of biomarkers. In other examples, signal intensities were normalized to the median and used to calculate relative levels of biomarkers. Measured levels of any individual biomarkers can be normalized by comparing the level to the mean or median measured level of two or more biomarkers from the same individual.

Relative biomarker levels in plasma are compared between control and AD groups revealing 46 discriminatory biomarkers: GCSF; IFN-g; IGFBP-1; BMP-6; BMP-4; Eotaxin-2; IGFBP-2; TARC; RANTES; ANG; PARC; Acrp30; AgRP (ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. An unsupervised clustering (that is, the clustering algorithm does not know which cases are AD and which are normal) of the 46 discriminatory markers results in the clustering of the samples into 2 groups or clusters, a cluster of control samples, and a cluster of AD samples. Sensitivity was calculated as the number of correctly classed AD samples in the AD cluster/total number of AD samples, which is 29/32 or 90.6%. Specificity was calculated as total number of correctly classed control samples in the control cluster/total number of controls, which is (14/19=73.6%).

Biomarker levels were compared between control and AD groups, revealing 20 biomarkers (shown in Table 3) that are differentially regulated (each is decreased in AD as compared to control) between the two groups. Statistical analysis was performed to find the probability that the finding of differential levels was in error (the "q" value) for any one biomarker. Biomarkers with differential levels and associated q values (shown as percentage values) are shown in Table 3 (fold change indicates the fold change between levels in control vs. AD samples). Sensitivity was calculated as number of AD samples in AD cluster/total number of AD samples, which is 29/32 or 90.6%. Specificity was calculated as total correctly predicted AD/total predicted AD (29/34=85%).

TABLE 3

| Qualitative Biomarker | Fold Change (as negative value or decrease) | q-value (%) |
| --- | --- | --- |
| Brain derived neurotrophic factor (BDNF) | 0.536 | 1.656 |
| Basic fibroblast growth factor (bFGF) | 0.673 | 1.656 |
| Epidermal growth factor (EGF) | 0.561 | 1.656 |
| Fibroblast growth factor-6 (FGF-6) | 0.664 | 1.656 |
| Interleukin-3 (IL-3) | 0.758 | 1.656 |
| Soluble interleukin-6 receptor (sIL-6 R) | 0.676 | 1.656 |
| Leptin (also known as OB) | 0.476 | 1.656 |
| Macrophage inflammatory protein 1-delta (MIP-1δ) | 0.542 | 1.656 |
| MSP-a | 0.764 | 1.656 |
| NAP-2 | 0.672 | 1.656 |
| Neurotrophin-3 (NT-3) | 0.698 | 1.656 |
| Platelet derived growth factor, BB dimer (PDGF-BB) | 0.536 | 1.656 |

TABLE 3-continued

| Qualitative Biomarker | Fold Change (as negative value or decrease) | q-value (%) |
| --- | --- | --- |
| RANTES | 0.682 | 1.656 |
| Stem cell factor (SCF) | 0.730 | 1.656 |
| sTNF RII | 0.700 | 1.656 |
| Transforming growth factor beta-3 (TGF-β3) | 0.769 | 1.656 |
| Tissue inhibitor of metalloproteases-1 (TIMP-1) | 0.716 | 1.656 |
| Tissue inhibitor of metalloproteases-2 (TIMP-2) | 0.750 | 1.656 |
| Tumor necrosis factor beta (TNF-β) | 0.649 | 1.656 |
| TPO | 0.714 | 1.656 |

Example 2

Decision Trees from AD Diagnosis Marker Data

Upon further analysis of the data from example 1, two different decision trees were formulated for diagnosis of AD using AD diagnosis biomarkers.

The first decision tree utilizes sIL-6R, IL-8, and TIMP-1 levels. The rules which make up the decision tree are: (1) If sIL-6R>5.18 and IL-8 is >0.957, the indication is normal; (2) if sIL-6R>5.18 and IL-8>0.957, the indication is AD; (3) if sIL-6R>5.18 and TIMP-1≦7.978, the indication is AD; and (4) if sIL-6R>5.18 and TIMP-1 is >7.978, the indication is normal, wherein the values expressed are relative concentrations.

Accuracy of this decision tree was measured using 10-fold cross-validation testing feature in CART to generate misclassification rates for learning samples and testing samples. Sensitivity was calculated from the testing scores as number of AD samples correctly predicted as AD/total number of AD samples (29/32=0.906). Specificity was calculated from the testing scores as total correctly predicted cases of AD/total number of cases predicted AD (29/33=0.878).

A second decision tree was formulating using BDNF, TIMP-1 and MIP-16 levels. The rules which make up the decision tree are: (1) if BDNF>4.476, the indication is normal; (2) if BDNF≦4.476 and TIMP-1≦8.942, the indication is AD; (3) if BDNF≦4.476, TIMP-1>8.942, and MIP-1δ≦1.89, the indication is AD; and (4) if BDNF<4.476, TIMP-1>8.942, and MIP-1δ>1.89, the indication is normal. Accuracy of this decision tree was measured using 10-fold cross-validation testing feature in CART to generate misclassification rates for learning samples and testing samples. Sensitivity was calculated from the testing scores as number of AD samples correctly predicted as AD/total number of AD samples (0.875). Specificity was calculated from the testing scores as total correctly predicted cases of AD/total number of cases predicted AD (0.82).

Example 3

Diagnosis of MCI

Levels of RANTES and Leptin were measured in 18 samples from control subjects (mean age=74) and 6 samples from patients diagnosed with mild cognitive impairment (MCI). MCI patients had been clinically diagnosed by a neurologist, and had an AULT-A7 score of less than 5 and Mini Mental State Exam (MMSE) scores ranging from 30-28. Control subjects had an AULT-A7 score greater than or equal to 5 and MMSE score ranging from 30-28.

RANTES and Leptin levels were measured using an ELISA kit from R&D systems according to the manufacturer's instructions. The raw ELISA expressions values were normalized by dividing each value by the median of all the samples. Analysis of the data showed (a) Leptin is not decreased in MCI patients as compared to control subjects (in the six MCI samples, Leptin was actually 11% higher than the control subjects), and (b) a bimodal distribution of RANTES, where MCI patients had RANTES levels of between 1.043 and 1.183 (levels from control subjects were either$\leq 1.043$ or $>1.183$). However, closer inspection of the data led us to believe that those control subjects with RANTES$\leq 1.043$ had been incorrectly classified as normal (and should have been diagnosed as MCI).

Reclassification of control subjects with RANTES$\leq 1.043$ as MCI patients allows the creation of a simple rule: if RANTES$\leq 1.183$ and Leptin$>=0.676$, the indication is MCI. Sensitivity and specificity, calculated as described in Example 2, were 83.3% and 88.88%, respectively.

Example 4

Monitoring and Stratification of AD Patients

Levels of RANTES, Leptin, PDGF-BB, and BDNF were measured in serum samples collected from 36 patients diagnosed with Alzheimer's Disease. (mean age of 74) using ELISA kits from R&D systems according to the manufacturer's instructions. The raw ELISA expressions values were normalized by dividing each value by the median of all the samples. The samples were grouped into three classes on the basis of MMSE score: Class 1 (mild AD), MMSE 27-22; Class 2 (moderate AD), MMSE 21-16; and Class 3 (severe AD), MMSE 15-12.

Upon analysis of the ELISA data, we formulated a decision tree using BDNF and PDGF-BB. The rules which make up the decision tree are: (1) if BDNF<0.626, the indication is mild AD; (2) if BDNF>0.626 and PDGF-BB<0.919, the indication is moderate AD; and (3) if BDNF>0.626 and PDGF-BB>0.919, the indication is severe AD. The values expressed are relative concentrations that have been normalized to the median. Average normalized levels for Leptin were: Class I=0.886; class II=0.757; class III=0.589. Average normalized levels for BDNF were: Class I=0.595; class II=0.956; class III=1.23. When applied to a set of "test" data, the decision tree produced 58%, 47%, and 57% percent correct stratification of the test samples into mild, moderate, and severe categories.

Example 5

Four Discriminatory Markers

The absolute concentrations in plasma of only 4 discriminatory markers, BDNF, PDGF-BB, LEPTIN, and RANTES measured by ELISA was used to classify samples. ELISA kits were purchased from R&D Systems, and measurements were obtained according to manufacturer recommendations. For example for RANTES, the following protocol was followed.

1. Add 50 µL standards, specimens or controls to appropriate wells.
2. Add 50 µL anti-RANTES Biotin Conjugate to each well.
3. Incubate wells at 37° C. for 1 hour.
4. Aspirate and wash wells 4× with Working Wash Buffer.
5. Add 100 µL Streptavidin-HRP Working Conjugate to each well.
6. Incubate for 30 minutes at room temperature.
7. Aspirate and wash wells 4× with Working Wash Buffer.
8. Add 100 µL of Stabilized Chromogen to each well.
9. Incubate at room temperature for 30 minutes in the dark.
10. Add 100 µL of Stop Solution to each well.
11. Read absorbance at 450 nm.

Following the above protocol, an unsupervised clustering of BDNF, PDGF-BB, LEPTIN, and RANTES was performed using the publicly available web based clustering software wCLUTO at cluto.ccgb.umn.edu/cgi-bin/wCluto/wCluto.cgi. Here the clustering of the 4 proteins resulted in the clustering of the samples into 2 groups or clusters, a cluster of control samples and a cluster of AD samples. Sensitivity was calculated as the number of correctly classed AD samples in the AD cluster/total number of AD samples, which is 21/24 or 87.5%. Specificity was calculated as total number of correctly classed control samples in the control cluster/total number of controls, which is 20/24=83.3%.

Additionally, absolute biomarker levels in plasma (as measured by ELISA) for BDNF, PDGF-BB, and LEPTIN, were correlated with MMSE scores (range 12-30). AD could be identified in MMSE scores in a range of 12-28 and control samples were identified in MMSE scores in the range of 25-30. Table 4 shows the correlations and their statistical significance (p-value). The upper and lower correlations show whether the upper end of the range of MMSE scores and biomarker concentrations or the lower end of the range of MMSE scores and biomarker concentrations are more correlated. Therefore, the correlations show that higher levels of BDNF and Leptin are significantly correlated with better MMSE scores, and that increase in the concentration of BDNF and Leptin from a reference point or an earlier collection is an indication of improvement in cognition as measured by MMSE. Simultaneously, or by itself, the lower the levels of PDGF-BB in men is significantly correlated with better MMSE scores, and a decrease in the concentration of PDGF-BB in male sample compared to an earlier collection in that male, is an indication of improvement in cognition as measured by MMSE.

The results show (Table 4) the correlation between the plasma concentration of 3 discriminatory proteins for AD to the MMSE score of the subjects and the correlation between concentrations of proteins that are discriminatory for AD. There was no correlation between MMSE score and Age among AD subjects and there was no correlation between Age and the concentration of BDNF, PDGF-BB, or LEPTIN in plasma among AD subjects. The p-values show that the correlations are statistically significant. The count shows the number of cases. BDNF has a statistically significant positive correlation with MMSE scores. PDGF-BB has a statistically significant negative correlation with MMSE scores in men. LEPTIN has a statistically significant positive correlation with MMSE scores. This experiment demonstrates that plasma concentrations for PDGF-BB, LEPTIN, and BDNF can be used to monitor the progression of cognitive decline.

TABLE 4

|  | Correlation | Count | Z-value | P-value | 95% Lower | 95% Upper |
|---|---|---|---|---|---|---|
| BDNF to MMSE | 0.184 | 165 | 2.373 | 0.0176 | 0.032 | 0.328 |
| BDNF to MMSE (Females) | 0.229 | 91 | 2.18 | 0.0289 | 0.024 | 0.415 |

TABLE 4-continued

|  | Correlation | Count | Z-value | P-value | 95% Lower | 95% Upper |
|---|---|---|---|---|---|---|
| PDGF-BB to MMSE (Males) | −0.207 | 74 | −1.769 | 0.0768 | −0.416 | 0.023 |
| LEPTIN to MMSE | 0.193 | 164 | 2.478 | 0.0132 | 0.041 | 0.336 |
| BDNF to PDGF-BB | 0.700 | 181 | 11.575 | 0.0001 | 0.617 | 0.768 |
| PDGF-BB to RANTES | 0.563 | 181 | 8.5 | 0.0001 | 0.454 | 0.655 |
| BDNF to RANTES | 0.714 | 181 | 11.9 | 0.0001 | 0.634 | 0.779 |

Controls and AD cases were age matched, and had a mean age of 74. The mean MMSE score for AD cases (n=24) was 20, while the mean MMSE score for Control cases (n=24) was 30.

Classification of the samples was performed with unsupervised clustering of protein concentration. The total accuracy of classification was 85.4%. This results demonstrated that plasma protein concentrations for BDNF, PDGF-BB, LEPTIN, and RANTES, as measured by ELISA can be used to accurately discriminate between AD and controls.

Example 6

Validation of Mean Protein Concentrations in AD and Controls by ELISA

Figure 1B:
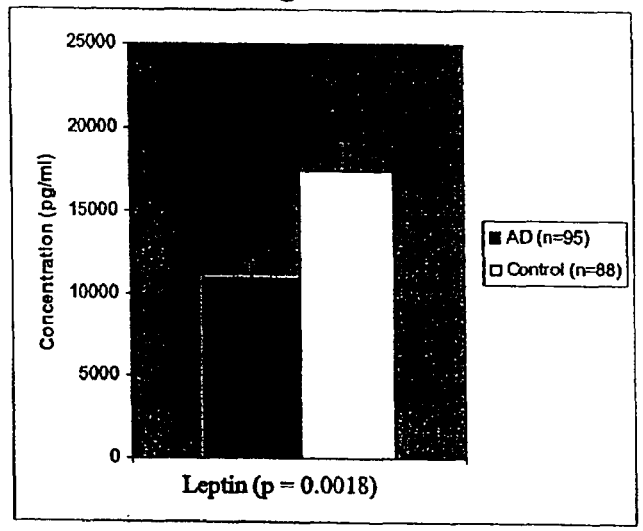
Figure 1C:
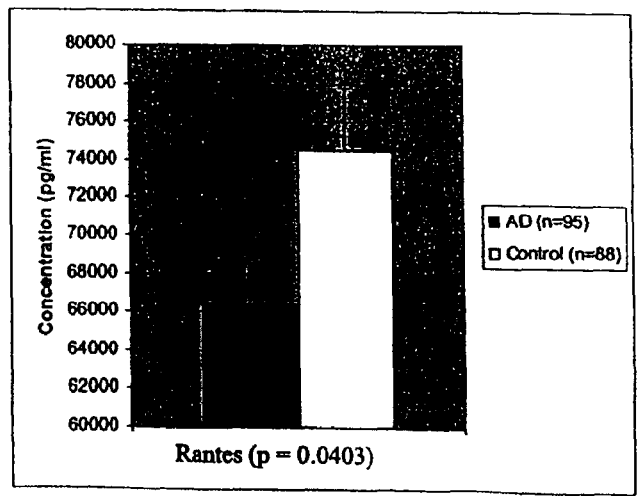

Protein concentrations for proteins, LEPTIN, BDNF and RANTES, in plasma samples of AD (n=95) to age matched Controls (n=88) are shown in FIGS. 1A-1C. One of the four proteins we measured was Brain Derived Neurotrophic Factor (BDNF). The mean concentration of BDNF in AD plasma was 8.1 ng/ml (SE+/−0.4) compared to the mean of control plasma 10.8 ng/ml (SE+/−0.68) and the difference was found to be extremely statistically significant (p-value=0.0006). We also found that the concentrations of BDNF were lower in other forms of dementia (5.74 ng/ml, n=20) than AD. The mean concentration of a second protein Leptin in AD plasma was found to be 10.9 ng/ml (SE+/−1.06) compared to the mean of control plasma 17.4 ng/ml (SE+/−1.8) and the difference was found to be statistically very significant (p-value=0.0018). The mean concentration of a third protein Rantes in AD plasma was found to be 66.3 ng/ml (SE+/−2.4) compared to control samples 74.5 ng/ml (SE+/−3.2) and the difference was found to be statistically significant (p-value=0.0403). No difference in the means of concentrations for RANTES, PDGF-BB, and BDNF were observed among AD subjects with MMSE scores=1>20 (n=54) and those <20 (n=41).

Example 7

Absolute Biomarker Concentrations in Plasma

Figure 2:
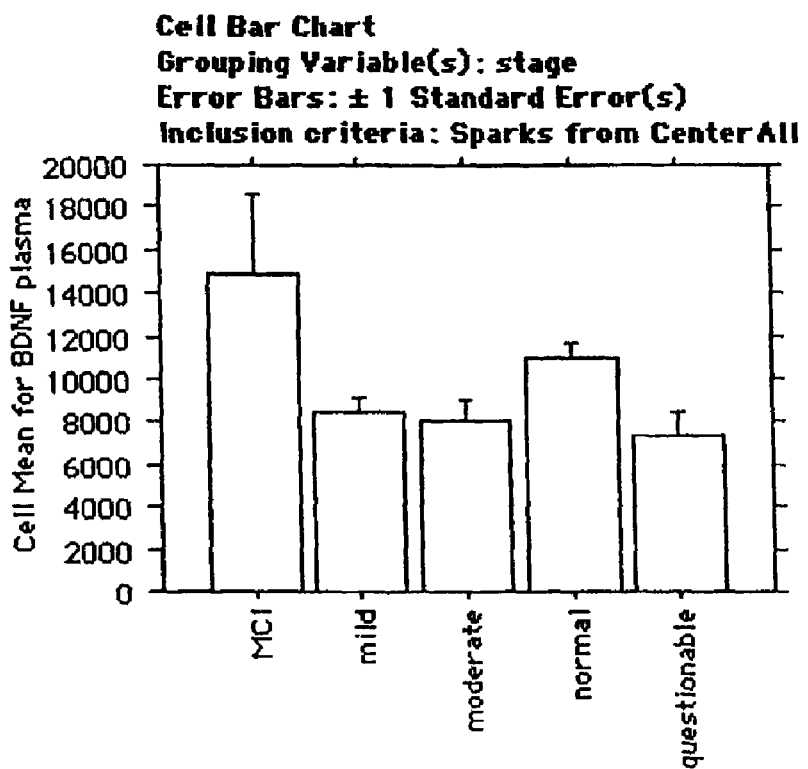
FIG. 2 shows a Cell Bar Chart for concentration of BDNF in plasma. (Cell Bar Chart Grouping Variable(s): stage Error Bars: ±1 Standard error(s) Inclusion criteria: Sparks from Center All)

Additionally, absolute biomarker concentrations in plasma were measured for BDNF, and mean concentrations for Controls was compared to MCI (Mild Cognitive Impairment), MMSE 25-28, MMSE 20-25, and MMSE 10-20. For the purposes of this experiment, the index used in the following example is: questionable AD is =MMSE score in the range of 25-28; mild AD=MMSE score in the range of 20-25; and moderate AD=MMSE score in the range of 10-20 and severe AD=MMSE score in the range of 10-20. For the purpose of Example 7, all individuals assessed as having Questionable AD were diagnosed by a physician as having AD. The FIG. 2 shows that mean concentrations of BDNF in plasma for MMSE 25-28; MMSE 20-25; MMSE 10-20 are significantly lower than the mean concentration in Controls (Normal, mean age 74) and the mean concentration of BDNF in MCI is significantly higher than in Controls and all cases of AD. FIG. 2.

Unpaired T-Test for BDHF Plasma
Grouping Variable: stage
Hypothesized Difference=0
Inclusion criteria: Sparks from Center All

|  | Mean Diff. | DF | t-Value | P-Value |
|---|---|---|---|---|
| MCI, mild | 6349.252 | 47 | 3.050 | .0038 |
| MCI, moderate | 6828.574 | 31 | 2.651 | .0125 |
| MCI, normal | 3961.358 | 86 | 1.442 | .1529 |
| MCI, questionable | 7547.218 | 17 | 2.550 | .0207 |
| mild, moderate | 479.322 | 68 | .460 | .6467 |
| mild, normal | −2387.894 | 123 | −2.270 | .0250 |
| mild, questionable | 1197.966 | 54 | .969 | .3369 |
| moderate, normal | −2867.216 | 107 | −2.175 | .0319 |
| moderate, questionable | 718.644 | 38 | .475 | .6372 |
| normal, questionable | 3585.860 | 93 | 1.993 | .0492 |

Group Info for BDNF Plasma
Grouping Variable: stage
Inclusion criteria: Sparks from Center All

|  | Count | Mean | Variance | Std. Dev. | Std. Err |
|---|---|---|---|---|---|
| MCI | 6 | 14879.833 | 85932530.967 | 9269.980 | 3784.454 |
| mild | 43 | 8530.581 | 15299257.963 | 3911.427 | 596.487 |
| moderate | 27 | 8051.259 | 22317487.815 | 4724.139 | 909.161 |
| normal | 82 | 10918.476 | 39478328.993 | 6283.178 | 693.861 |
| questionable | 13 | 7332.615 | 15122872.923 | 3888.814 | 1078.563 |

Figure 3:
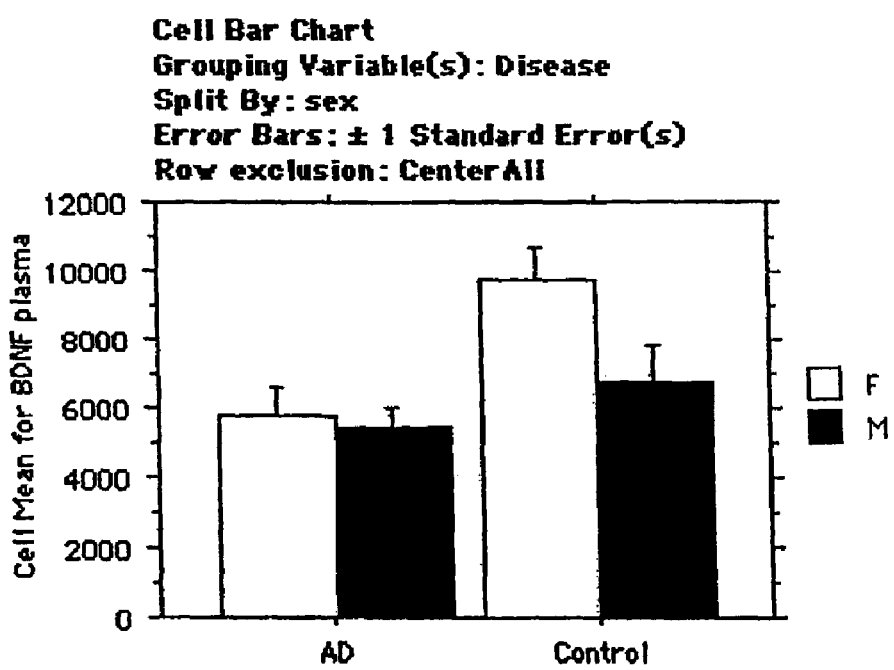
FIG. 3 shows BDNF in control vs AD for male and female. (Cell Bar Chart Grouping Variable(s): Disease Split By: sex Error Bars: ±1 Standard Error(s) Row exclusion: Center All)

Additionally, absolute concentrations of BDNF, in plasma samples collected from four separate Alzheimer's Centers was compared for gender differences in mean concentrations between AD (Females) and Control (Females) and AD (Males) and Control (Males). FIG. 3 shows that there is 40% difference in the concentration of BDNF in AD Females compared to Control Females and the difference is highly statistically significant (p-value=0.004). The difference in the mean concentration of BDNF for all AD cases compared to all Control case was found to be extremely statistically significant (p-value=0.0006).

Unpaired T-Test for BDHF Plasma
Grouping Variable: Disease
Split By: sex
Hypothesized Difference=0
Row exclusion: Center All

|  | Mean Diff. | DF | t-Value | P-Value |
|---|---|---|---|---|
| AD, Control: Total | −2974.140 | 187 | −3.482 | .0006 |
| AD, Control: F | −3939.353 | 87 | −2.924 | .0044 |
| AD, Control: M | −1348.601 | 92 | −1.165 | .2469 |

Results for totals may not agree with results for individual cells because of missing values for split variables.

Group Info for BDHF Plasma
Grouping Variable: Disease
Split By: sex
Row exclusion: CenterAll

|  | Count | Mean | Variance | Std. Dev. | Std. Err |
|---|---|---|---|---|---|
| AD: Total | 106 | 5596.113 | 24323422.844 | 4931.878 | 479.026 |
| AD: F | 38 | 5775.921 | 25121499.318 | 5012.135 | 813.076 |
| AD: M | 62 | 5396.774 | 24336564.079 | 4933.210 | 626.518 |
| Control: Total | 83 | 8570.253 | 46322420.606 | 6806.058 | 747.062 |
| Control: F | 51 | 9715.275 | 50173107.603 | 7083.298 | 991.860 |
| Control: M | 32 | 6745.375 | 36011373.274 | 6000.948 | 1060.828 |

Results for totals may not agree with results for individual cells because of missing values for split variables.

Figure 4:
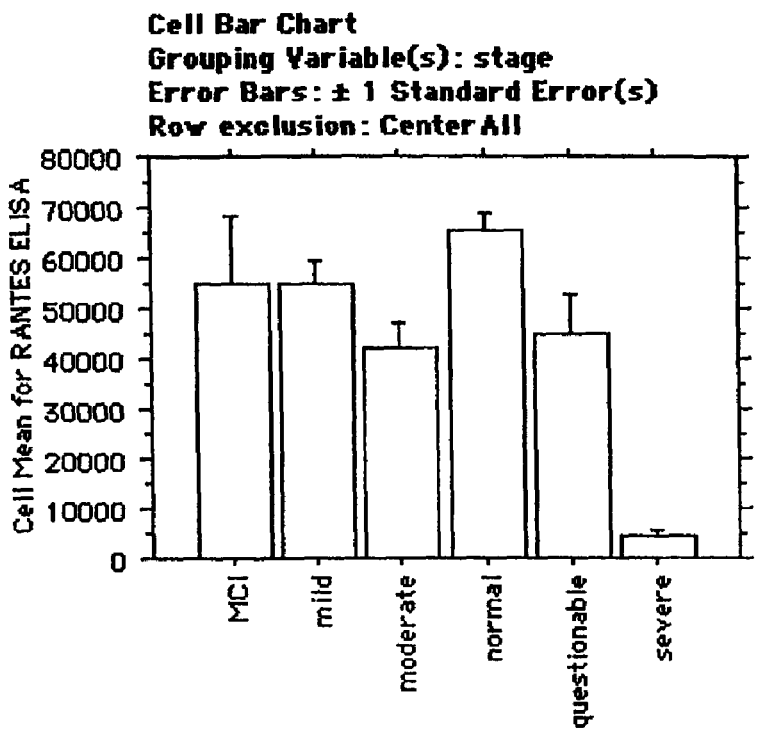
FIG. 4 shows RANTES concentration in plasma. (Cell Bar Chart Grouping Variable(s): stage Error Bars: ±1 Standard Error(s) Row exclusion: Center All)

Additionally, absolute biomarker concentrations in plasma were measured for RANTES in plasma samples collected from four different Alzheimer's Centers, and mean concentrations for Controls were compared to MCI (Mild Cognitive Impairment), MMSE 25-28; (MMSE 20-25; MMSE 10-20; and MMSE 10-20. The index is described above. The mean differences between Mild AD compared to Moderate AD, Mild AD compared to Normal, Mild AD compared to Severe AD, Moderate AD compared to Normal, Questionable AD compared to Normal, Normal to Severe AD were all found to be statistically significant. FIG. 4.

Unpaired t-Test for RANTES ELISA
Grouping Variable: stage
Hypothesized Difference=0
Row exclusion: CenterAll

|  | Mean Diff. | DF | t-Value | P-Value |
|---|---|---|---|---|
| MCI, mild | 84.789 | 64 | .007 | .9945 |
| MCI, moderate | 12454.688 | 51 | 1.042 | .3022 |
| MCI, normal | −10422.892 | 106 | −.866 | .3884 |
| MCI, questionable | 9682.438 | 29 | .682 | .5007 |
| MCI, severe | 50349.200 | 10 | 1.647 | .1305 |
| mild, moderate | 12369.899 | 97 | 1.814 | .0728 |
| mild, normal | −10507.681 | 152 | −1.775 | .0780 |
| mild, questionable | 9597.649 | 75 | 1.081 | .2830 |
| mild, severe | 50264.411 | 56 | 2.031 | .0470 |
| moderate, normal | −22877.580 | 139 | −3.606 | .0004 |
| moderate, questionable | −2772.250 | 62 | −.315 | .7535 |
| moderate, severe | 37894.512 | 43 | 1.647 | .1069 |
| normal, questionable | 20105.330 | 117 | 2.353 | .0203 |
| normal, severe | 60772.092 | 98 | 2.395 | .0185 |
| questionable, severe | 40666.762 | 21 | 1.624 | .1192 |

Group Info for RANTES ELISA
Grouping Variable: stage
Row exclusion: CenterAll

|  | Count | Mean | Variance | Std. Dev. | Std. Err |
|---|---|---|---|---|---|
| MCI | 10 | 54919.200 | 1729660285.733 | 41589.185 | 13151.655 |
| mild | 56 | 54834.411 | 1203622609.701 | 34693.265 | 4636.082 |
| moderate | 43 | 42464.512 | 1036226732.256 | 32190.476 | 4909.002 |
| normal | 98 | 65342.092 | 1275358885.672 | 35712.167 | 3607.474 |
| questionable | 21 | 45236.762 | 1201710117.890 | 34665.691 | 7564.674 |
| severe | 2 | 4570.000 | 2976800.000 | 1725.341 | 1220.000 |

Figure 5:
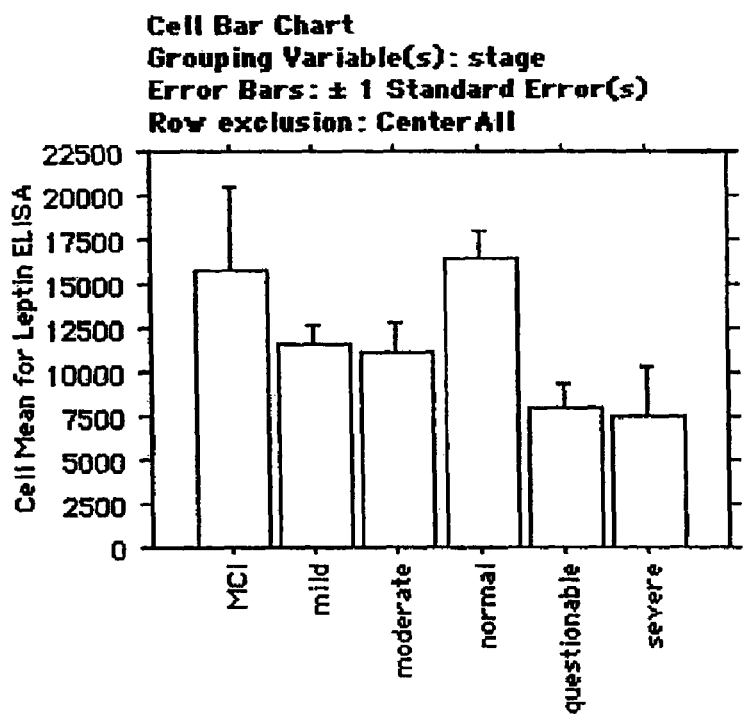
FIG. 5 shows concentration of Leptin in plasma. (Cell Bar Chart Grouping Variable(s): stage Error Bars: ±1 Standard Error(s) Row exclusion: Center All)

Additionally, absolute biomarker concentrations in plasma were measured for Leptin in plasma samples collected from four different Alzheimer's Centers, and mean concentrations for Controls were compared to MCI (Mild Cognitive Impairment); MMSE 25-28; MMSE 20-25; MMSE 10-20; and MMSE 10-20. The mean differences between Questionable AD compared to MCI, Mild AD compared to Normal, Mild AD compared to Questionable AD, Questionable AD compared to Normal, and Moderate AD compared to Normal were all found to be statistically significant. FIG. 5.

Unpaired T-Test for Leptin ELISA
Grouping Variable: stage
Hypothesized Difference=0
Row exclusion: Center All

|  | Mean Diff. | DF | t-Value | P-Value |
|---|---|---|---|---|
| MCI, mild | 4164.889 | 64 | 1.338 | .1856 |
| MCI, moderate | 4707.044 | 51 | 1.061 | .2939 |
| MCI, normal | −650.092 | 105 | −.123 | .9022 |
| MCI, questionable | 7793.348 | 29 | 2.000 | .0550 |
| MCI, severe | 8187.800 | 10 | .739 | .4767 |
| mild, moderate | 542.155 | 97 | .272 | .7860 |
| mild, normal | −4814.981 | 151 | −2.117 | .0359 |
| mild, questionable | 3628.458 | 75 | 1.897 | .0617 |
| mild, severe | 4022.911 | 56 | .734 | .4661 |
| moderate, normal | −5357.136 | 138 | −1.963 | .0516 |
| moderate, questionable | 3086.303 | 62 | 1.085 | .2822 |
| moderate, severe | 3480.756 | 43 | .403 | .6892 |
| normal, questionable | 8443.439 | 116 | 2.368 | .0195 |
| normal, severe | 8837.892 | 97 | .778 | .4383 |
| questionable, severe | 394.452 | 21 | .078 | .9383 |

Group Info for Leptin ELISA
Grouping Variable: stage
Row exclusion: Center All

|  | Count | Mean | Variance | Std. Dev. | Std. Err |
|---|---|---|---|---|---|
| MCI | 10 | 15727.300 | 225300738.678 | 15010.021 | 4746.585 |
| mild | 56 | 11562.411 | 58790550.756 | 7667.500 | 1024.613 |
| moderate | 43 | 11020.256 | 145797834.909 | 12074.677 | 1841.371 |
| normal | 97 | 16377.392 | 255125297.032 | 15972.642 | 1621.776 |
| questionable | 21 | 7933.952 | 47833192.348 | 6916.154 | 1509.229 |
| severe | 2 | 7539.500 | 16125520.500 | 4015.659 | 2839.500 |

Figure 6:
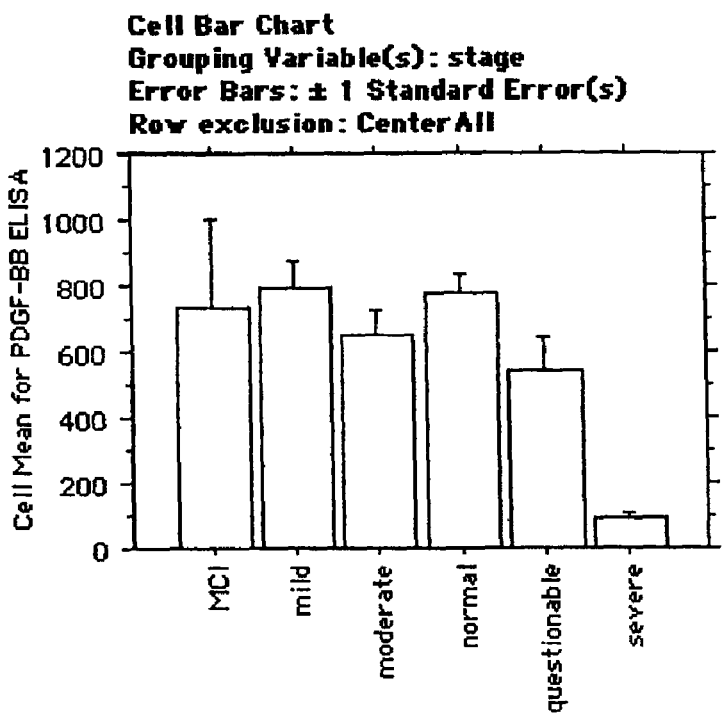
FIG. 6 shows PDGF-BB concentration in plasma. (Cell Bar Chart Grouping Variable(s): stage Error Bars: ±1 Standard Error(s) Row exclusion: Center All)

Additionally, absolute biomarker concentrations in plasma were measured for PDGF-BB in plasma samples collected from four different Alzheimer's Centers, and mean concentrations for Controls were compared to MCI (Mild Cognitive Impairment); MMSE 25-28; MMSE 20-25; MMSE 10-20; and MMSE 10-20. The mean differences between Questionable AD compared to Mild AD, Mild AD compared to Severe AD, Moderate AD compared to Severe AD, Normal compared to Questionable AD, and Normal to Severe AD were all found to be statistically significant. FIG. 6.

Unpaired T-Test for PDGF-BB ELISA
Grouping Variable: stage
Hypothesized Difference=0
Row exclusion: Center All

|  | Mean Diff. | DF | t-Value | P-Value |
|---|---|---|---|---|
| MCI, mild | −62.275 | 58 | −.286 | .7756 |
| MCI, moderate | 81.595 | 44 | .411 | .6831 |
| MCI, normal | −42.865 | 103 | −.210 | .8343 |
| MCI, questionable | 191.571 | 28 | .810 | .4246 |
| MCI, severe | 637.000 | 9 | 1.072 | .3117 |
| mild, moderate | 143.869 | 86 | 1.285 | .2023 |
| mild, normal | 19.410 | 145 | .199 | .8426 |
| mild, questionable | 253.846 | 70 | 1.812 | .0742 |
| mild, severe | 699.275 | 51 | 1.745 | .0871 |
| moderate, normal | −124.459 | 131 | −1.201 | .2320 |
| moderate, questionable | 109.977 | 56 | .869 | .3885 |
| moderate, severe | 555.405 | 37 | 1.716 | .0945 |
| normal, questionable | 234.436 | 115 | 1.767 | .0799 |
| normal, severe | 679.865 | 96 | 1.696 | .0931 |
| questionable, severe | 445.429 | 21 | 1.278 | .2153 |

Group Info for PDGF-BB ELISA
Grouping Variable: stage
Row exclusion: Center All

|   | Count | Mean | Variance | Std. Dev. | Std. Err |
|---|---|---|---|---|---|
| MCI | 9 | 731.000 | 650139.000 | 806.312 | 268.771 |
| mild | 51 | 793.275 | 315391.883 | 561.598 | 78.639 |
| moderate | 37 | 649.405 | 204231.470 | 451.920 | 74.295 |
| normal | 96 | 773.865 | 318171.171 | 564.067 | 57.570 |
| questionable | 21 | 539.429 | 233024.657 | 482.726 | 105.340 |
| severe | 2 | 94.000 | 648.000 | 25.456 | 18.000 |

Figure 7:
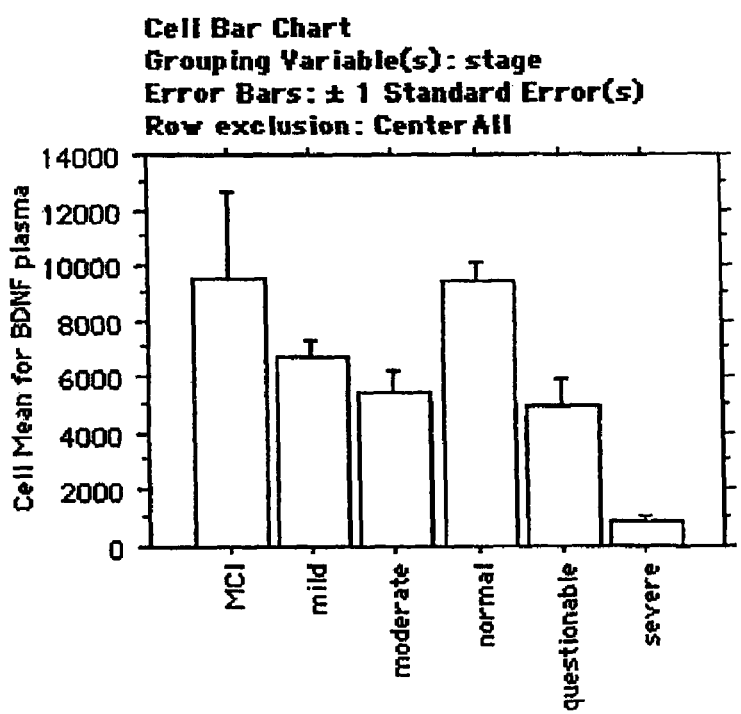
FIG. 7 shows BDNF concentration in plasma. (Cell Bar Chart Grouping Variable(s): stage Error Bars: ±1 Standard Error(s) Row exclusion: Center All)

Additionally, absolute biomarker concentrations in plasma were measured for BDNF in plasma samples collected from four different Alzheimer's centers, and means concentrations for Controls were compared to MCI (Mild Cognitive Impairment), Questionable AD (MMSE 25-28), Mild differences between MCI compared to Moderate AD, MCI compared to Questionable AS, Mild AD to Normal, Mild AD to sever AD, Moderate to Normal, Normal to Questionable AD, and Normal to Severe were all found to be statistically significant. FIG. 7.

Unpaired T-Test for BDNF Plasma
Grouping Variable: stage
Hypothesized Difference=0
Row exclusion: Center All

|   | Mean Diff. | DF | t-Value | P-Value |
|---|---|---|---|---|
| MCI, mild | 2819.186 | 64 | 1.433 | .1568 |
| MCI, moderate | 4071.016 | 51 | 1.877 | .0663 |
| MCI, normal | 124.278 | 106 | .053 | .9578 |
| MCI, questionable | 4535.757 | 29 | 1.806 | .0813 |
| MCI, severe | 8660.400 | 10 | 1.202 | .2570 |
| mild, moderate | 1251.831 | 97 | 1.262 | .2098 |
| mild, normal | −2694.908 | 152 | −2.638 | .0092 |
| mild, questionable | 1716.571 | 75 | 1.447 | .1520 |
| mild, severe | 5841.214 | 56 | 1.726 | .0898 |
| moderate, normal | −3946.739 | 139 | −3.431 | .0008 |
| moderate, questionable | 464.741 | 62 | .360 | .7199 |
| moderate, severe | 4589.384 | 43 | 1.265 | .2128 |
| normal, questionable | 4411.480 | 117 | 2.868 | .0049 |
| normal, severe | 8536.122 | 98 | 1.781 | .0781 |
| questionable, severe | 4124.643 | 21 | 1.321 | .2006 |

Group Info for BDNF Plasma
Grouping Variable: stage
Row exclusion: Center All

|   | Count | Mean | Variance | Std. Dev. | Std. Err |
|---|---|---|---|---|---|
| MCI | 10 | 9511.900 | 96113654.322 | 9803.757 | 3100.220 |
| mild | 56 | 6692.714 | 22509096.208 | 4744.375 | 633.994 |
| moderate | 43 | 5440.884 | 25765123.534 | 5075.936 | 774.073 |
| normal | 98 | 9387.622 | 45504479.969 | 6745.701 | 681.419 |
| questionable | 21 | 4976.143 | 18681976.129 | 4322.265 | 943.196 |
| severe | 2 | 851.500 | 63724.500 | 252.437 | 178.500 |

It has been found that for Questionable AD (MMSE score in the range of 25-28) the levels of Leptin and PDGF-BB increase significantly whereas BDNF and RANTES do not change significantly. It has been found that from Mild AD (MMSE score in the range of 20-25) to Moderate AD (MMSE score in the range of 10-20) the level of LEPTIN does not decline whereas the levels for RANTES, BDNF and PDGF-BB declines.

Example 8

In an attempt to identify proteins that are altered in the peripheral immune system in AD, expression levels of 120 cytokines, chemokines, and growth factors in plasma from 32 AD patients and 19 nondemented age-matched controls were measured using spotted antibody microarrays on filters. Statistical analysis identified 20 proteins as significantly different between AD and controls. Six of them including brain derived neurotrophic factor (BDNF) and NT-3, and PDGF-BB, EGF, FGF-6, bFGF, TGF-b3 have known neurotrophic activity and were significantly reduced in AD plasma. BDNF levels correlated with better cognitive function in the mini mental state exam (MMSE). BDNF measurements in plasma from two hundred AD cases and controls using commercial sandwich ELISA showed a highly significant 25% reduction in AD cases. Consistent with the array data, reduced plasma BDNF levels were associated with impaired memory function. BDNF is critical for neuronal maintenance, survival, and function. Without being bound by theory decreased blood levels of neurotrophins and BDNF may be linked with neurodegeneration and cognitive dysfunction in AD.

Example 9

Additional Biomarkers

Additionally, qualitative biomarker levels for GDNF, SDF-1, IGFBP3, FGF-6, TGF-b3, BMP-4, NT-3, EGF, BDNF, IGFBP-2 were correlated with MMSE scores (range 12-30) for AD (MMSE range 12-28) and control samples (MMSE range 25-30). Table 5 shows the correlations and their statistical significance (p-value). The upper and lower correlations show whether the upper end of the range of MMSE Scores and biomarker concentrations or the lower end of the range of MMSE scores and biomarker concentrations are more correlated. A negative correlation means that MMSE scores increase with decreasing levels of biomarker and vice versa. A positive correlation mean that MMSE scores increase with increasing levels of biomarker.

TABLE 5

|   | Correlation | Count | Z-value | P-value | 95% Lower | 95% Upper |
|---|---|---|---|---|---|---|
| GDNF to MMSE | −0.258 | 42 | −1.646 | 0.0997 | −0.521 | 0.05 |
| SDF-1 to MMSE | −0.363 | 42 | −2.375 | 0.0175 | −0.601 | −0.066 |
| IGFBP-3 to MMSE | 0.293 | 42 | 1.886 | 0.0593 | −0.012 | 0.548 |
| FGF-6 to MMSE | 0.471 | 42 | 3.192 | 0.0014 | 0.195 | 0.687 |
| TGF-b3 to MMSE | 0.317 | 42 | 2.049 | 0.0405 | 0.014 | 0.566 |
| BMP-4 to MMSE | 0.294 | 42 | 1.845 | 0.0583 | −0.011 | 0.545 |
| NT-3 to MMSE | 0.327 | 42 | 2.118 | 0.0342 | 0.025 | 0.574 |
| EGF to MMSE | 0.409 | 42 | 2.711 | 0.0067 | 0.12 | 0.634 |
| BDNF to MMSE | 0.464 | 42 | 3.139 | 0.0017 | 0.187 | 0.673 |
| IGFBP-2 to MMSE (Females) | 0.498 | 24 | 2.5 | 0.0123 | 0.118 | 0.75 |

Example 10

This example shows Table 6, a Summary of Quantitative Markers for Identification and Stratification of AD.

TABLE 6

| References | Samples | Plasma BioMarker | % Difference in Samples | p-value |
|---|---|---|---|---|
| Normal | Questionable AD | BDNF | −46% | 0.0049 |
| Normal | Questionable AD | Leptin | −52% | 0.0195 |
| Normal | Questionable AD | RANTES | −31% | 0.0203 |
| Normal | Questionable AD | PDGF-BB | −30% | 0.0799 |
| Normal | Mild AD | BDNF | −29% | 0.0092 |
| Normal | Mild AD | Leptin | −29% | 0.0359 |
| Normal | Mild AD | RANTES | −16% | 0.0780 |
| Normal | Moderate AD | BDNF | −42% | 0.0008 |
| Normal | Moderate AD | Leptin | −33% | 0.0359 |
| Normal | Moderate AD | RANTES | −35% | 0.0004 |
| Normal | Severe AD | BDNF | −90% | 0.0781 |
| Normal | Severe AD | RANTES | −93% | 0.0185 |
| Normal | Severe AD | PDGF-BB | −89% | 0.0931 |
| Questionable AD | Mild AD | Leptin | 45% | 0.0617 |
| Questionable AD | Mild AD | PDGF-BB | 46% | 0.0742 |
| Mild AD | Moderate AD | RANTES | −23% | 0.0780 |
| Mild AD | Severe AD | BDNF | −87% | 0.0898 |
| Mild AD | Severe AD | RANTES | −92% | 0.0470 |
| Mild AD | Severe AD | PDGF-BB | −88% | 0.0871 |
| Questionable AD | MCI | BDNF | 91% | 0.0813 |
| Questionable AD | MCI | Leptin | 98% | 0.0550 |
| MCI | Mild AD | BDNF | −42% | 0.0038 |

Accordingly, the present invention provides methods of aiding diagnosis of Alzheimer's disease ("AD"), comprising comparing a measured level of at least 4 AD diagnosis biomarkers, wherein said biomarkers comprise BDNF, PDGF-BB, Leptin and RANTES, in a biological fluid sample from an individual to a reference level for each AD diagnosis biomarker. Accordingly, methods are provided in which BDNF decreased at least about 10%, about 15%, about 20%, about 25% or about 30% as compared to a reference level of BDNF, indicates cognitive impairment, such as for example, an indication of AD. Accordingly, methods are provided in which Leptin decreased at least about 10%, about 15%, about 20%, about 25% or about 30% as compared to a reference level of Leptin, indicates cognitive impairment, such as for example, an indication of AD. Accordingly, methods are provided in which RANTES decreased at least about 5%, about 10%, or about 15% as compared to a reference level of RANTES, indicates cognitive impairment, such as for example, an indication of AD. Accordingly, methods are provided in which PDGF-BB decreased at least about 80%, about 85% or about 90% as compared to a reference level of PDGF-BB, indicates cognitive impairment, such as for example, an indication of severe AD.

TABLE 7

| Protein | Alternate names | Class | Protein ID |
|---|---|---|---|
| alpha-1 acid glycoprotein | | acute phase | |
| alpha-1 antitrypsin | | acute phase | |
| Ceruloplasmin | | acute phase | |
| Haptoglobin | | acute phase | |
| Hemopexin | | acute phase | |
| Hemoxygenase | | acute phase | |
| plasminogen activator inhibitor-1 | PAI-1 | acute phase | |
| serum amyloid A | SAA | acute phase | |
| serum amyloid P | SAP | acute phase | |
| 4-11313 ligand | 4-1BBL/CD137L | apoptosis | P41273 |
| BAFF | TALL-1 | apoptosis | Q9Y275 |
| soluble TRAIL receptor 3 | TRAIL sR3/TNFR S10C | apoptosis | O14755 |
| soluble TRAIL receptor 4 | TRAIL sR4/TNFR S10D | apoptosis | Q9UBN6 |
| TNF-related death ligand 1a | TRDL-1a/APRIL | apoptosis | AF046888 |
| TNFSF-14 | LIGHT | apoptosis | O43557 |
| TRAIL | Apo2L | apoptosis | P50591 |
| BCA-1 | BLC | chemokine | O43927 |
| CCL-28 | CCK-1 | chemokine | |
| cutaneous T cell attracting chemokine | CTACK, CCL27 | chemokine | Qgz1X0 |
| ENA-78 | | chemokine | P42830 |
| Eotaxin-1 | | chemokine | P51671 |
| Eotaxin-2 | MPIF-2 | chemokine | O00175 |
| Eotaxin-3 | CCL26 | chemokine | Q9Y258 |
| Fractalkine | neurotactin | chemokine | P78423 |
| Granulocyte chemotactic protein 2 | GCP-2 | chemokine | P80162 |
| GRO alpha | MGSA | chemokine | P09341 |
| GRO beta | MIP-2alpha | chemokine | P19875 |
| GRO gamma | MIP-2beta | chemokine | P19876 |
| haemoinfiltrate CC chemokine 1 | HCC-1 | chemokine | Q16627 |
| haemoinfiltrate CC chemokine 4 | HCC-4/CCL16 | chemokine | O15476 |
| I-309 | TCA-3/CCL-1 | chemokine | P22362 |
| IFNgamma inducible protein-10 | IP-10 | chemokine | P02778 |
| IFN-inducible T cell alpha chemokine | I-TAC/CXCL11 | chemokine | AF030514 |
| interleukin-8 | IL-8/NAP-1 | chemokine | P10145 |
| leucocyte cell-derived chemotaxin-2 | LECT2 | chemokine | |
| Lungkine | CXCL-15/WECHE | chemokine | |
| Lymphotactin | Lptn/ATAC | chemokine | P47992 |
| | | | MIP-1alpha/ pLD78/ |

TABLE 7-continued

| Protein | Alternate names | Class | Protein ID |
|---|---|---|---|
| macrophage inflammatory protein 1alpha | CCL3 | chemokine | P10147 |
| macrophage inflammatory protein 1beta | MIP-1beta/ACT-2/CCL4 | chemokine | P13236 |
| macrophage inflammatory protein 1d | MIP-1d/CCL15/LKN-1 | chemokine | |
| macrophage inflammatory protein 1gamma | MIP-1gamma/CCL9/MIP-3alpha/CCL20/ | chemokine | |
| macrophage inflammatory protein 3alpha | LARC | chemokine | P78556 |
| macrophage inflammatory protein 3beta | MIP-3beta/ELC/CCL19 | chemokine | Q99731 |
| macrophage-derived chemokine | MDC/STCP-1 | chemokine | O00626 |
| monocyte chemoattractant protein-1 | MCP-1/CCL2 | chemokine | P13500 |
| monocyte chemoattractant protein-2 | MCP-2/CCL8 | chemokine | P78388 |
| monocyte chemoattractant protein-3 | MCP-3/CCL7 | chemokine | P80098 |
| monocyte chemoattractant protein-4 | MCP-4/CCL13 | chemokine | Q99616 |
| monocyte chemoattractant protein-5 | MCP-5/CCL12 | chemokine | |
| monokine induced by IFN gamma | MIG | chemokine | Q07325 |
| mucosa-associated chemokine | MEC | chemokine | AF266504 |
| Myeloid progenitor inhibitory factor | MPIF/CKbeta8/CCL23 | chemokine | |
| platelet basic protein | PBP/CTAP-III/NAP-2 | chemokine | P02775 |
| platelet factor 4 | PF-4/CXCL4 | chemokine | P02776 |
| pulmonary activation regulated chemokine | PARC/CCL18/MIP-4 | chemokine | |
| RANTES | CCL5 | chemokine | P13501 |
| secondary lymphoid tissue chemokine | SLC/6Ckine | chemokine | O00585 |
| stromal cell derived factor 1 | SDF-1/CXCL12 | chemokine | P48061 |
| thymus activation regulated chemokine | TARC/CCL17 | chemokine | Q92583 |
| thymus expressed chemokine | TECK/CCL25 | chemokine | O15444 |
| C1q | | collectin | |
| mannose binding lectin | MBL | collectin | |
| surfactant protein A | SP-A | collectin | |
| surfactant protein D | SP-D | collectin | |
| C1 inhibitor | | complement | |
| C3a | | complement | |
| C4b binding protein | C4BP | complement | |
| C5a | | complement | |
| complement C3 | C3 | complement | |
| complement C5 | C5 | complement | |
| complement C8 | C8 | complement | |
| complement C9 | C9 | complement | |
| decay accelerating factor | DAF | complement | |
| Factor H | | complement | |
| membrane inhibitor of reactive lysis | MIRL/CD59 | complement | |
| Properdin | | complement | |
| soluble complement receptor 1 | sCR1 | complement | |
| soluble complement receptor 2 | sCR2 | complement | |
| cardiotrophin-1 | CT-1 | cytokine | Q16619 |
| CD27 | | cytokine | P26842 |
| CD27L | CD70 | cytokine | P32970 |
| CD30 | Ki-1 | cytokine | P28908 |
| CD30L | TNFSF8 | cytokine | P32971 |
| CD40L | TRAP/CD154 | cytokine | P29965 |
| interferon alpha | IFNalpha | cytokine | P01562 |
| interferon beta | IFNbeta | cytokine | P01574 |
| interferon gamma | IFNgamma | cytokine | P01579 |
| interferon omega | IFNomega | cytokine | P05000 |
| interferon-sensitive gene 15 | ISG-15 | cytokine | P05161 |
| Leptin | OB | cytokine | P41159 |
| leukemia inhibitory factor | LIF/CNDF | cytokine | P15018 |
| Lymphotoxin | LT/TNF beta | cytokine | P01374 |
| macrophage colony stimulating factor | M-CSF/CSF-1 | cytokine | P09603 |
| macrophage stimulating protein-alpha | MSPalpha/HGF1 | cytokine | P26927 |
| macrophage stimulating protein-beta | MSPbeta/HGF1 | cytokine | P26927 |
| migration inhibition factor | MIF/GIF | cytokine | P14174 |
| oncostatin M | OSM | cytokine | P13725 |
| RANKL | TRANCE/TNFSF-11 | cytokine | O14788 |
| soluble IL6 R complex | sIL6RC (gp130 + sIL6R) | cytokine | |
| soluble Fas ligand | sCD95L | cytokine | P48023 |
| TNF type I receptor | TNF-RI p55 | cytokine | P19438 |
| TNF type II receptor | TNF-R p75 | cytokine | P20333 |
| TNFSF-18 | GITRL/AITRL | cytokine | O95852 |
| tumor necrosis factor alpha | TNF-alpha/Apo3L/DR3-L/TNFSF-12 | cytokine | P01375 |
| TWEAK | | cytokine | O43508 |
| acidic fibroblast growth factor | aFGF | growth factor | P05230 |
| activin beta A | | growth factor | P08476 |
| agouti related protein | AGRP | growth factor | AAB52240 |
| Amphiregulin | AR/SDGF | growth factor | P15514 |
| angiopoietin-like factor | ALF | growth factor | |
| basic fibroblast growth factor | bFGF | growth factor | P09038 |
| Betacellulin | | growth factor | P35070 |

TABLE 7-continued

| Protein | Alternate names | Class | Protein ID |
|---|---|---|---|
| bone morphogenic protein 2 | BMP2 | growth factor | P12643 |
| bone morphogenic protein 4 | BMP4 | growth factor | |
| bone morphogenic protein 5 | BMP5 | growth factor | |
| bone morphogenic protein 6 | BMP6 | growth factor | |
| bone morphogenic protein 7 | BMP7 | growth factor | |
| cripto-1 | CRGF | growth factor | |
| epidermal growth factor | EGF | growth factor | P01133 |
| Erythropoietin | Epo | growth factor | |
| fibroblast growth factor 17 | FGF-17 | growth factor | |
| fibroblast growth factor 18 | FGF-18 | growth factor | |
| fibroblast growth factor 19 | FGF-19 | growth factor | |
| fibroblast growth factor 2 | FGF-2 | growth factor | |
| fibroblast growth factor 4 | FGF-4 | growth factor | |
| fibroblast growth factor 6 | FGF-6 | growth factor | |
| fibroblast growth factor 7 | FGF-7/KGF | growth factor | |
| fibroblast growth factor 8 | FGF-8 | growth factor | |
| fibroblast growth factor 9 | FGF-9 | growth factor | |
| Flt3 ligand | Flt L | growth factor | P49771 |
| Follistatin | FSP | growth factor | |
| Granulocyte colony stimulating factor | G-CSF | growth factor | P09919 |
| granulocyte/macrophage CSF | GM-CSF | growth factor | P04141 |
| growth and differentiation factor 11 | GDF-11 | growth factor | |
| growth and differentiation factor 15 | GDF-15 | growth factor | |
| growth arrest specific gene 6 | Gas-6 | growth factor | |
| heparin-binding epidermal growth factor | HB-EGF | growth factor | Q99075. |
| hepatocyte growth factor | HGF/SF | growth factor | P14210 |
| hepatopoietin A | HPTA/HRG alpha/ neuregulin | growth factor | |
| heregulin alpha | NDF/HRG beta/neuregulin/ | growth factor | |
| heregulin beta | NDF | growth factor | |
| IGF binding protein-1 | IGFBP-1 | growth factor | |
| IGF binding protein-2 | IGFBP-2 | growth factor | |
| IGF binding protein-3 | IGFBP-3 | growth factor | |
| IGF binding protein-4 | IGFBP-4 | growth factor | |
| inhibin A | | growth factor | |
| inhibin B | | growth factor | |
| insulin-like growth factor IA | IGF-IA | growth factor | P01343 |
| insulin-like growth factor IB | IGF-IB | growth factor | P05019 |
| insulin-like growth factor II | IGF-II | growth factor | P01344 |
| macrophage galatose-specific lectin 1 | MAC-1 | growth factor | |
| Neuritin | | growth factor | |
| Neurturin | | growth factor | |
| orexin A | | growth factor | |
| Osteonectin | SPARC | growth factor | |
| Osteoprotegrin | TNFRSF11B | growth factor | |
| placenta growth factor | PGIF | growth factor | |
| platelet derived growth factor alpha | PDGF-A | growth factor | P04085 |
| platelet derived growth factor beta | PDGF-B | growth factor | P01127 |
| pregnancy zone protein | | growth factor | |
| Prolactin | PRL | growth factor | P01236 |
| sensory and motor neuron-derived factor | SMDF | growth factor | |
| soluble GM-CSF receptor | sGM-CSF R | growth factor | P15509 |
| stem cell factor | SLF/SCF/kit ligand/MGF | growth factor | P21583 |
| Thrombopoietin | TPO/c-MPL ligand | growth factor | P40225 |
| thymic stromal lymphoprotein | TSLP | growth factor | |
| Thymopoietin | Tpo | growth factor | |
| transforming growth factor alpha | TGF-alpha | growth factor | P01135 |
| transforming growth factor beta 1 | TGF-beta1 | growth factor | P01137 |
| transforming growth factor beta 2 | TGF-beta2 | growth factor | P08112 |
| transforming growth factor beta 3 | TGF-beta3 | growth factor | P10600 |
| vascular endothelial growth factor | VEGF | growth factor | P15692 |
| interleukin-1 receptor antagonist | ILiRa | interleukin | P18510 |
| interleukin-10 | IL-10 | interleukin | P22301 |
| interleukin-11 | IL-11 | interleukin | P20809 |
| interleukin-12p35 | IL-12p35 | interleukin | P29459 |
| interleukin-12p40 | IL-12p40 | interleukin | P29460 |
| interleukin-13 | IL-13 | interleukin | P35225 |
| interleukin-14 | IL-14 | interleukin | L15344 |
| interleukin-15 | IL-15 | interleukin | P40933 |
| interleukin-16 | IL-16 | interleukin | Q14005 |
| interleukin-17 | IL-17 | interleukin | Q16552 |
| interleukin-18 | IL-18 | interleukin | Q14116 |
| interleukin-1alpha | IL-1al.pha | interleukin | P01583 |
| interleukin-1beta | IL-1beta | interleukin | P01584 |
| interleukin-2 | IL-2 | interleukin | P01585 |
| interleukin-3 | IL-3 | interleukin | P08700 |
| interleukin-4 | IL-4 | interleukin | P05112 |

TABLE 7-continued

| Protein | Alternate names | Class | Protein ID |
|---|---|---|---|
| interleukin-5 | IL-5 | interleukin | P05113 |
| interleukin-6 | IL-6 | interleukin | P05231 |
| interleukin-7 | IL-7 | interleukin | P13232 |
| interleukin-9 | IL-9 | interleukin | P15248 |
| soluble interleukin-1 receptor I | sIL1R/CD121a | interleukin | P14778 |
| soluble interleukin-1 receptor II | sIL1R/CD121b | interleukin | P27930 |
| soluble interleukin-2 receptor | IL-2R/CD25 | interleukin | P01589 |
| soluble interleukin-5 receptor | sIL-5R/CD125 | interleukin | Q01344 |
| soluble interleukin-6 receptor | sIL-6R/CD126 | interleukin | P08887 |
| soluble interleukin-7 receptor | sIL-7R/CD127 | interleukin | P16871 |
| soluble interleukin-9 receptor | sIL-9R | interleukin | PQ01113 |
| AD7C | NTP | neuronal | AF010144 |
| alpha synuclein | | neuronal | AAH13293 |
| GAP-43 | | neuronal | |
| Neurofilament | | neuronal | |
| Synaptogamin | | neuronal | |
| Synaptophysin | | neuronal | |
| tau P199 | | neuronal | |
| brain derived neurotrophic factor | BDNF | neurotrophin | P23560 |
| ciliary neurotrophic factor | CNTF | neurotrophin | P26441 |
| glial derived neurotrophic factor | GDNF | neurotrophin | P39905 |
| nerve growth factor | NGF | neurotrophin | P01138 |
| neurotrophin 3 | NT-3 | neurotrophin | P20783 |
| neurotrophin 4 | NT-4 | neurotrophin | P34130 |
| soluble CNTF receptor | sCNTFR | neurotrophin | P26992 |
| alpha2-macroglobulin | alpha 2M | others | |
| Alzheimer associated protein | ALZAS | others | |
| amyloid beta protein | Abeta 1-x | others | |
| apolipoprotein A | apoA | others | |
| apolipoprotein B | apoB | others | |
| apolipoprotein D | apoD | others | |
| apolipoprotein E | apoE | others | |
| apolipoprotein J | apoD/clusterin | others | |
| C reactive protein | CRP | others | |
| clara cell protein | CC16 | others | |
| glial fibrillary acidic protein | GFAP | others | |
| Melanotransferrin | | others | |
| soluble transferring receptor | TfR | others | |
| Thrombomodulin | | others | |
| Thrombospondin | Tsp | others | |
| tissue transglutaminase | | others | |
| Transferrin | | others | |
| alpha 1-antichymotrypsin | ACT | protease | NP001076 |
| C1r | | protease | |
| C1s | | protease | |
| complement C2 | C2 | protease | |
| Factor B | | protease | |
| Factor D | adipsin | protease | |
| FactorI | | protease | |
| Kallikrein | | protease | |
| MBL-associated serine protease 1 | MASP-1 | protease | |
| MBL-associated serine protease 2 | MASP-2 | protease | |
| Neuroserpin | | protease | AAH18043 |
| secretory leukocyte protease inhibitor | SLPI | protease | |
| Angiogenin | | vascular | |
| Angiostatin | | vascular | P00747 |
| Endostatin | | vascular | |
| Endothelin | | vascular | |
| soluble E selectin | s E selectin | vascular | |
| vascular endothelial growth inhibitor | VEGI | vascular | |

Example 11

This example describes methods useful for measuring the levels of AD biomarkers and/or analyzing data regarding measurements of the levels of AD biomarkers and/or correlating data based on the measurements of the levels of AD biomarkers and/or identifying AD biomarkers by analyzing and/or correlating data based on the measurements of the levels of AD biomarkers obtained from biological samples from subjects across different test centers. These methods are also applicable to biological samples obtained from an individual and/or single collection center. The methods are designed to minimize or reduce test center variability resulting from collection procedures and/or storage and handling conditions. This example, along with Example 12, provides methods for identifying additional biomarkers that are useful in the detection of AD, including markers which provide a high degree of sensitivity (calculated as the number of AD samples in the AD cluster divided by the total number of AD samples used in the experiment) and specificity (calculated as the number of controls in the control cluster divided by total number of controls used in the experiment for diagnosing AD), as well as identifying such biomarkers.

Collection procedures as well as storage and handling conditions can introduce variability in the concentration of biomarkers measured in biological samples, such as plasma, of AD and Control Subjects. This in turn could cause misclassification of subjects without appropriate normalization and/or standardization and/or controls. For example, protein concentrations may be affected, in part, by whether a particular plasma sample is platelet rich or platelet poor. In general, plasma samples that are platelet rich will have greater quantitative levels of many biomarkers, while samples that are platelet poor will have reduced quantitative levels of many biomarkers (as compared to appropriate controls, for example population controls). For example, the concentration of BDNF, which is tightly held within platelets, was measured as a surrogate for platelet degranulation and therefore the release of BDNF from platelets. It was observed that carefully prepared platelet poor plasma has a concentration of BDNF that is equivalent to 10 pg/ml whereas platelet rich preparations of plasma can have concentrations as high as 20 ng/ml. The correlation of BDNF measured by ELISA and BDNF measured by spotted filter antibody array has an r=0.679, with p<0.0001. The samples used in the experimental design were prepared in a manner such that they did not include platelet poor preparation of BDNF, as these are not representative of plasma collection in common practice. In some examples, plasma is used as the biological sample for the methods disclosed herein rather than serum. Plasma was used in the methods of Example 1, and Examples 11-14. This is due, in part, to the variables involved in the blood clotting process used to make serum. These variables may lead to varying degrees of proteolysis of biomarkers contained in the serum. Also, if plasma is used, there is less chance of inadvertently removing a protein of interest. If large amounts of fibrinogen or albumin do present a problem, there are depletion kits publicly available to deplete the plasma of these proteins, although if this is done, associated proteins may be removed as well. If depletion kits are used, appropriate controls to monitor removal of the associated proteins may be used in the methods.

Sterile blood collection tubes that are pre-loaded with protease inhibitors, as well as a self-contained system for removing red blood cells and platelets are publicly available. See for example, the Beckton Dickenson Company product lists at: bd.com/vacutainer/products/venous/ordering_info_tubes.asp.

The protocol below is one illustrative example of sample collection procedures.

Becton Dickenson BD P100 tubes are stored at 4° C., until use. A full 8.5 mL of blood is collected to produce about 2.5-3 mL of plasma. Immediately after collection, the tube is inverted 8-10 times to mix the protease inhibitors and anticoagulent with the blood sample. The tube is placed in wet ice before centrifuging. (Centrifugation should be done within 30 minutes of collection). The tubes are centrifuged at 2000-3000 RCF at 4° C. for 15 min. (See BD P100 package insert for converting rpm to RCF). Do not exceed 3000 g, or 10,000 RCF.

Within 30 minutes of centrifugation, the plasma is transferred in 1-mL aliquots to pre-labeled Fisherbrand 4-mL self-standing cryovials (Fisher Scientific # 0566966) and immediately placed on dry ice. Aliquots are frozen at −80° C. until used. (Avoid freeze-thaw cycles). To remove microplatelets, the plasma is transferred to a different centrifuge tube, and is centrifuged at 12,000 g at 4° C. for 15 min.

The objective of this experiment, in part, was to determine methods, including identification of appropriate controls, for use in analyzing data that minimize individual variations in the immune response and variations produced by collection and storage conditions while identifying AD subjects with a high degree of specificity and sensitivity.

The methods used in the experiments were the same as described herein in Example 1 with filter based antibody arrays consisting of 120 antibodies specific for the proteins, that is biomarkers, listed in Table 8. In some previous experiments using filter based antibody arrays of 120 antibodies specific for the biomarkers listed in Table 8 (the designation of "_1" after each biomarker name in Tables 8, 9A1-9A2 and 9B, 10A1-10A2 and 10B, 11A1-11A2 and 11B, and 12A-12B is a function of the program and is not part of the name of each biomarker) when a signal was not detectable, it was not clear if this was a false negative result (for example, due to problems with the use of certain of the reagents) or a true negative result. In the following experiments, due to improvements made by the manufacturer of the reagents (RayBiotech), it was determined that a signal could be detected for all of the 120 proteins screened using the antibody arrays. This improvement in reagents resulted in identification of additional biomarkers (as shown in Example 12) for use in the methods as disclosed herein, such as for example, in methods for aiding in the diagnosis of and/or diagnosing AD, which biomarkers may or may not have been detectable in previous experiments.

In this experiment, the levels of the 120 biomarkers listed in Table 8 were measured for biological samples collected at five different Alzheimer's centers (n=34, mean age=74, Mean MMSE=20) including 16 samples collected 1.5 yrs apart from 8 subjects with AD, who were later confirmed by autopsy to have AD, were compared to controls, for example, age matched controls collected from two centers (n=17) and other non-AD neurodegenerative age-matched controls (n=16) consisting of 4 subjects diagnosed with Parkinson's disease, and 12 subjects diagnosed with peripheral neuropathy. Power calculations show that 10 samples of autopsy confirmed AD samples are necessary to have an Alpha of 0.001 and power of 0.999.

Experimental data for all 120 biomarkers were extracted using Imagene software licensed from Biodiscovery. The extracted data was then normalized to the positive control for the experiment spotted on the blot. An example of a positive control is IgG. The data for each individual biomarker was then normalized to the median concentration of all 120 proteins measured by the antibody array. The Significance analysis of microarrays (SAM) was used to determine significance of each biomarker. This method for normalizing data extracted from a blot experiment minimizes or reduces variability due to the fact that individual samples can have slightly higher or lower levels of proteins based on the individual's immune response status. Following the determination of significance using SAM, the biomarkers with p-values less than or equal to 0.1% (53 markers) were used for cluster analysis to classify AD from controls. (See Tables 13A (biomarkers that are positively correlated) and 13B (biomarkers that are negatively correlated for the markers listed that have a p-value % of about 0.1). All biomarkers with p-values less than or equal to 5% (Tables 9A1-9A2 and 9B) were all used in cluster analysis to classify samples as AD based on the controls used. Results of analysis of extracted data that were normalized as described above are disclosed in Example 12 and Tables 13A-13B (unclustered, and in order of highest ranked biomarker to lowest ranked biomarker, significantly increased (13A) or decreased (13B) in AD compared to age-matched normal controls plus other non-AD forms of neurodegeneration, such as PD an PN (that is, as compared to all controls). The columns from left to right for Tables 13A-13B are biomarker Name, Score (d), fold change and p-value (%). Tables 9A1-9A2 and 9B as described in Example 12 show an additional analysis of data for biomarkers having a p-value of greater than 0.1% and less than 5%.

Example 12

This example describes methods for identifying AD biomarkers that are either increased or decreased in individuals diagnosed with AD compared to healthy age matched controls and/or neurodegenerative age matched controls that are non-AD, that is, non-AD neurodegenerative controls, such as Parkinson's Disease (PD), and peripheral neuropathy (PN). This is important because AD is a neurodegenerative disease, and it is advantageous to identify biomarker patterns of neurodegeneration associated with AD, in terms of identification of biomarkers that are either decreased or increased with respect to an appropriate control(s), that are unique to AD and/or distinguishable from other non-AD forms of neurodegeneration, such as for example PD and PN, in the same age group, as well as with respect to healthy age-matched controls.

Previous experiments (see Example 1) determined that any one or more of the following biomarkers could be used for the detection of AD: GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; EGF-R. Based upon the experimental conditions and analysis described in Example 11, additional biomarkers useful for detecting AD were identified. The measured values for the biomarkers from Table 8 were subjected to hierarchical clustering based on classification of samples with normalized concentration surveyed. Based upon the clustering analysis, the proteins were segregated into 9 classes of similarities based on correlation. Biomarkers with greater than a 5% p value (%) were eliminated from the analysis. Sensitivity of the classification is calculated as the number of AD samples in the AD cluster divided by the total number of AD samples used in the experiment (in this case 31/34=91%). Specificity is calculated as the number of controls in the control cluster divided by total number of controls used in the experiment (in this case 31/33=94%).

Tables 13A-13B provide a listing of biomarkers as described in Example 11. Tables 9A1-9A2 and 9B provide a listing of biomarkers (clustered by methods as described above) in order of highest ranked biomarker to lowest ranked biomarker within each cluster based on score value) that are significantly increased (9A1-9A2) or decreased (9B) in AD compared to age-matched normal controls plus other non-AD forms of neurodegeneration, such as for example PD and PN (that is, as compared to all controls). The columns from left to right for Table 9A1-A2 and 9B are: biomarker name; Score (d); Fold change; q-value(%) and cluster number. Significance analysis of microarrays is discussed in for example Tusher et al., 2001, PNAS, vol. 98:5116. Any one or more of the biomarkers listed in Table 9A1-A2 and 9B can be used in the methods disclosed herein, such as for examples, methods for aiding in the diagnosis of or diagnosing AD. As described herein, multiple AD diagnosis biomarkers may be selected from the AD diagnosis biomarkers disclosed in Tables 9A1-9A2 and 9B by selecting for cluster diversity. The highest ranked biomarkers from each of the 9 clusters shown in Tables 9A1-9A2 and 9B (both positively correlated and negatively correlated) are: BTC (cluster 0); SDF-1 (cluster 1); MCP-2 (cluster 2); IFN-gamma (cluster 3); IGFBP-4 (cluster 4); IGF-1SR (cluster 5); IL-8 (cluster 6); GM-CSF (cluster 7); and ANG-2 (cluster 8). In some examples, biomarkers for use in the methods disclosed herein, such as for example, methods for aiding in the diagnosis of AD or diagnosing AD, include at least one marker selected from the group consisting of BTC; SDF-1; MCP-2; IFN-gamma; IGFBP-4; IGF-1SR; IL-8; GM-CSF; and ANG-2 or at least one marker from Tables 13A-13B. In some examples, additional biomarkers for use in the methods disclosed herein, such as for example, methods for aiding in the diagnosis of AD or diagnosing AD, include biomarkers that correlate with one or more of BTC; SDF-1; MCP-2; IFN-gamma; IGFBP-4; IGF-1SR; IL-8; GM-CSF; and ANG-2, that is, such biomarkers that have a Correlation: greater than 90% (r=0.9 to r=0.99); and a P-value less than 0.001 up to 0.05.

In some examples, biomarkers for use in the methods disclosed herein, such as for example, methods for aiding in the diagnosis of AD or diagnosing AD include two or more markers selected from the group consisting of BTC; SDF-1; MCP-2; IFN-gamma; IGFBP-4; IGF-1SR; IL-8; GM-CSF; and ANG-2. In some examples, biomarkers for use in the methods disclosed herein, such as for example, methods for aiding in the diagnosis of AD or diagnosing AD include markers comprising BTC; SDF-1; MCP-2; IFN-gamma; IGFBP-4; IGF-1SR; IL-8; GM-CSF; and ANG-2. In other examples, the top ranked 2, 3, 4, or 5 biomarkers from one or more clusters represented in Tables 9A1-9A2 and 9B are selected for use in the methods as disclosed herein.

Tables 10A1-10A2 and 10B provide a listing of biomarkers (not clustered and in order of highest ranked biomarker to lowest ranked biomarker based on score value) that are significantly increased (10A1-10A2) or decreased (10B) in AD compared to healthy age-matched controls. The columns from left to right in Tables 10A1-10A2 and 10B, Tables 11A1-11A2 and 11B, and Tables 12A-12B are Biomarker name, Score(d); Fold change; and q-value(%). Based on Tables 10A1-10A2 and 10B, identified biomarkers that are significantly increased in AD as compared to healthy age-matched controls include, but are not limited to (in descending order based on score): BTC; ANG-2; MIF; IGFBP-6; spg130; CTACK; IGFBP3; MIP-1a; TRAIL R4; IL-12 p40; AR; NT-4; VEGF-D; OSM; OST; IL-11; sTNF R1; I-TAC; Eotaxin; TECK; PIGF; bNGF; Lymphotactin; MIP-3b; HCC-4; ICAM-3; DTK; IL-1 RI; IGF-1 SR; GRO; GITR-Light; HGF; IL-1R4/ST; IL-2 Ra; ENA-78; and FGF-9. Based on Tables 10A1-10A2 and 10B, identified biomarkers that are significantly decreased in AD as compared to healthy age-matched controls include, but are not limited to (in descending order based on score): MCP-2; M-CSF; MCP-3; MDC; MCP-4; IL-1b; IL-4; IL-1a; BLC; CK b8-1; IL-2; IL-15; MIP3a; MIG; SCF; IL-6; IL-16; Eotaxin-3; I-309; TGF-beta; TGF-alpha; GDNF; LIGHT; SDF; IFG-1; Fractalkine; IL-5; Flt-3 ligand; GM-CSF; and GCP-2. Any one or more of the biomarkers listed in Tables 10A1-10A2 and 10B can be used in the methods disclosed herein, such as for example, for aiding in the diagnosis of or diagnosing AD.

Tables 11A1-11A2 and 11B provide a listing of biomarkers (not clustered and in order of highest ranked biomarker to lowest ranked biomarker based on score value) that are significantly increased (11A1-11A2) or decreased (11B) in AD compared to age-matched degenerative controls. Based on Tables 11A1-11A2 and 11B, identified biomarkers that are significantly increased in AD as compared to age-matched other non-AD neurodegenerative controls include, but are not limited to (in descending order based on score): TRAIL R4; Eotaxin; IL-12 p40; BTC-1; MIF; OST; MIP-1a; sTNF R1;

IL-11; Lymphotactin; NT-4; VEFG-D; HGF; IGFBP3; IGFBP-1; OSM; IL-1R1; PlGF; IGF-1 SR; CCL-28; IL-2 Ra; IL-12 p70; GRO; IGFBP-6; IL-17; CTACK; I-TAC; ICAM-3; ANG-2; MIP-3b; FGF-9; HCC-4; IL-1R4/ST; GITR; and DTK. Based on Tables 11A1-11A2 and 11B, identified biomarkers that are significantly decreased in AD as compared to age-matched other non-AD neurodegenerative controls include, but are not limited to (in descending order based on score): MCP-2; M-CSF; MCP-3; MDC; MCP-4; IL-1b; IL-4; IL-1a; BLC; CKb8-1; IL-2; IL-15; MIP3a; MIG; SCF; IL-6; IL-16; Eotaxin-3; I-309; TGF-beta; TNF-alpha; GDNF; LIGHT; SDF-1; IFG-1; Fractalkine; IL-5; Flt-3 Ligand; GM-CSF; and GCP-2. Any one or more of the biomarkers listed in Tables 11A1-11A2 and 11B can be used in the methods disclosed herein, such as for example, methods for aiding in the diagnosis of or diagnosing AD.

Tables 12A-12B provide a listing of biomarkers (not clustered and in order of highest ranked biomarker to lowest ranked biomarker based on score value) that are significantly increased (12A) or decreased (12B) in AD plus other non-AD neurodegenerative controls with reference to age matched controls. Any one or more of the biomarkers listed in Tables 12A-12B can be used in the methods disclosed herein, such as for example, methods for aiding in the diagnosis of or diagnosing neurodegenerative diseases, including AD. In other examples, the top ranked 2, 3, 4, or 5 biomarkers listed in Tables 12A-12B are selected for use in the methods as disclosed herein. In some examples, additional biomarkers for use in the methods disclosed herein, such as for example, methods for aiding in the diagnosis of AD or diagnosing AD, include biomarkers that correlate with the top ranked 1, 2, 3, 4, or 5 biomarkers listed in Tables 12A-12B, that is, such biomarkers that have a Correlation: greater than 90% (r=0.9 to r=0.99); and a P-value less than 0.001 up to 0.05.

As will be understood by the skilled artisan, biomarkers disclosed herein in the Examples and Tables can be selected for use in the methods disclosed herein depending on the type of measurement desired. For example, any one or more of the markers selected from the group consisting of the markers listed in Table 7 and/or Table 8 can be used to aid in the diagnosis of AD or for diagnosing AD. In some examples, biomarkers from Table 7 and/or Table 8 are selected for use in the methods disclosed herein based on the following criteria: Correlation: greater than 90% (r=0.9 to r=0.99); P-value less than 0.001 up to 0.05; Fold change greater than 20%; and a Score greater than 1 (for markers that increase, that is, that are positively correlated) or less than 1 (for markers that decrease, that is, that are negatively correlated).

In other examples, one or more markers selected from the group consisting of GCSF; IFN-g; IGFBP-1; BMP-6; BMP-4; Eotaxin-2; IGFBP-2; TARC; RANTES; ANG; PARC; Acrp30; AgRP(ART); TIMP-1; TIMP-2; ICAM-1; TRAIL R3; uPAR; IGFBP-4; LEPTIN(OB); PDGF-BB; EGF; BDNF; NT-3; NAP-2; IL-1ra; MSP-a; SCF; TGF-b3; TNF-b; MIP-1d; IL-3; FGF-6; IL-6 R; sTNF RII; AXL; bFGF; FGF-4; CNTF; MCP-1; MIP-1b; TPO; VEGF-B; IL-8; FAS; and EGF-R can be used in the methods disclosed herein, such as, for example, to aid in the diagnosis of AD or for the diagnosis of AD. In other examples, one or more biomarkers selected from Tables 12A-12B can be used to aid in the detection of general neurodegenerative disorders (including AD) and/or to diagnose neurodegenerative disorders generally while one or more biomarkers selected from Tables 9A1-9A2 and 9B can be used to aid in the diagnosis of AD or to diagnose AD and/or distinguish AD from other non-AD neurodegenerative diseases. In other examples, one or more biomarkers from Tables 10A1-10A2 and 10B or Tables 11A1-11A2 and 11B can be used to aid in the diagnosis of AD or to diagnose AD.

In addition to the biomarkers identified above, additional biomarkers can be identified by the methods described herein and methods known in the art. The parameters for selection of additional biomarkers are as follows:
Correlation: greater than 90% (r=0.9 to r=0.99);
P-value less than 0.001 up to 0.05;
Fold change greater than 20%; and
a Score greater than 1 (for markers that increase) or less than 1 (for markers that decrease).

Example 13

This example provides the biomarkers for aiding in the diagnosis of or diagnosing AD identified in two different experiments (single collection center and multi-collection center) as being significant.

Additional biomarkers, sTNF RII; MSP-alpha; uPAR; TPO; MIP-1beta; VEGF-beta; FAS; MCP-1; NAP-2; ICAM-1; TRAIL R3; PARC; ANG; IL-3; MIP-1delta; IFN-gamma; IL-8; and FGF-6 were identified as significant in both the experiment from a single collection center (see Example 1) and the multi-test center experiment (Examples 11-12) that was normalized as described in Examples 11-12. Of these 18 biomarkers, two, IFN-gamma and IL-8, also appear in Tables 9A1-9A2 and 9B as the highest ranked biomarker from cluster 3 and cluster 6, respectively. Accordingly, biomarkers for use in the methods of the present invention for aiding in the diagnosis of or diagnosing AD include IFN-gamma and/or IL-8. It was found that the following two biomarkers were useful as normalization controls in the methods of the present invention for aiding in the diagnosis of or diagnosing AD: TGF-beta and TGF-beta3. Accordingly, biomarkers for use in the methods of the present invention, such as for example, for aiding in the diagnosis of or diagnosing AD include TGF-beta and/or TGF-beta3 as normalization controls.

TABLE 8

| List of Biomarkers |
|---|
| ANG_1 |
| BDNF_1 |
| BLC_1 |
| BMP-4_1 |
| BMP-6_1 |
| CK b8-1_1 |
| CNTF_1 |
| EGF_1 |
| Eotaxin_1 |
| Eotaxin-2_1 |
| Eotaxin-3_1 |
| FGF-6_1 |
| FGF-7_1 |
| Flt-3 Ligand_1 |
| Fractalkine_1 |
| GCP-2_1 |
| GDNF_1 |
| GM-CSF_1 |
| I-309_1 |
| IFN-g_1 |
| IGF-1_1 |
| IGFBP-1_1 |
| IGFBP-2_1 |
| IGFBP-4_1 |
| IL-10_1 |
| IL-13_1 |
| IL-15_1 |
| IL-16_1 |
| IL-1a_1 |
| IL-1b_1 |

TABLE 8-continued

List of Biomarkers

IL-1ra_1
IL-2_1
IL-3_1
IL-4_1
IL-5_1
IL-6_1
IL-7_1
LEPTIN(OB)_1
LIGHT_1
MCP-1_1
MCP-2_1
MCP-3_1
MCP-4_1
M-CSF_1
MDC_1
MIG_1
MIP-1d_1
MIP-3a_1
NAP-2_1
NT-3_1
PARC_1
PDGF-BB_1
RANTES_1
SCF_1
SDF-1_1
TARC_1
TGF-b_1
TGF-b3_1
TNF-a_1
TNF-b_1
Acrp30_1
AgRP(ART)_1
ANG-2_1
AR_1
AXL_1
bFGF
b-NGF_1
BTC_1
CCL-28_1
CTACK_1
DTK_1
EGF-R_1
ENA-78_1
FAS_1
FGF-4_1
FGF-9_1
GCSF_1
GITR_1
GITR-Light_1
GRO_1
GRO-a_1
HCC-4_1
HGF_1
ICAM-1_1
ICAM-3_1
IGF-1 SR
IGFBP3_1
IGFBP-6_1
IL-1 RI_1
IL-11_1
IL-12 p40_1
IL-12 p70_1
IL-17_1
IL-1R4/ST2_1
IL-2 Ra_1
IL-6 R_1
IL-8_1
I-TAC_1
Lymphotactin_1
MIF_1
MIP-1a_1
MIP-1b_1
MIP-3b_1
MSP-a_1
NT-4_1
OSM_1
OST_1
PIGF_1

TABLE 8-continued

List of Biomarkers spg130_1
sTNF RI_1
sTNF RII_1
TECK_1
TIMP-1_1
TIMP-2_1
TPO_1
TRAIL R3_1
TRAIL R4_1
uPAR_1
VEGF-B_1
VEGF-D_1

TABLE 9A1

| Name | Score (d) | Fold Change | q-value (%) | Cluster |
|---|---|---|---|---|
| BTC_1 | 5.280599 | 2.30404 | 0.102881 | 0 |
| TRAIL R4__ | 4.18957 | 4.38847 | 0.102881 | 0 |
| MIF_1 | 3.78626 | 2.46763 | 0.102881 | 0 |
| MIP-1a_1 | 3.671968 | 2.04509 | 0.102881 | 0 |
| sTNF RII__ | 3.57664 | 1.81136 | 0.102881 | 0 |
| MSP-a_1 | 3.532718 | 2.23649 | 0.102881 | 0 |
| OST_1 | 3.519536 | 2.85493 | 0.102881 | 0 |
| uPAR_1 | 3.42578 | 3.10753 | 0.102881 | 0 |
| TPO_1 | 3.260328 | 2.04533 | 0.102881 | 0 |
| NT-4_1 | 3.182778 | 2.48474 | 0.102881 | 0 |
| MIP-1b_1 | 3.119065 | 2.07252 | 0.102881 | 0 |
| NAP-2_1 | 2.970365 | 1.51262 | 0.102881 | 0 |
| ICAM-1_1 | 2.949073 | 1.6633 | 0.102881 | 0 |
| IGFBP3_1 | 2.868921 | 1.68668 | 0.102881 | 0 |
| TRAIL R3__ | 2.808197 | 1.85516 | 0.102881 | 0 |
| Eotaxin_1 | 2.747874 | 2.23776 | 0.102881 | 0 |
| VEGF-B_1 | 2.73066 | 1.94657 | 0.102881 | 0 |
| PARC_1 | 2.703205 | 1.59801 | 0.102881 | 0 |
| sTNF RI_1 | 2.628389 | 2.27051 | 0.102881 | 0 |
| PIGF_1 | 2.59266 | 2.46572 | 0.102881 | 0 |
| OSM_1 | 2.548107 | 1.79103 | 0.102881 | 0 |
| ANG_1 | 2.527071 | 1.38167 | 0.102881 | 0 |
| FAS_1 | 2.522175 | 1.42939 | 0.102881 | 0 |
| VEGF-D_1 | 2.453761 | 3.08586 | 0.102881 | 0 |
| Acrp30_1 | 2.277494 | 2.1151 | 0.102881 | 0 |
| TIMP-1_1 | 1.815742 | 1.3765 | 0.102881 | 0 |
| TIMP-2_1 | 1.768441 | 1.37666 | 0.102881 | 0 |
| MIP-3b_1 | 1.516186 | 1.55797 | 0.290698 | 0 |
| RANTES__ | 1.482515 | 1.29415 | 0.290698 | 0 |
| EGF-R_1 | 1.461975 | 1.24406 | 0.362319 | 0 |
| CCL-28_1 | 1.332609 | 2.09378 | 0.362319 | 0 |
| GCSF_1 | 1.248565 | 1.39107 | 0.531915 | 0 |
| bFGF | 1.135651 | 1.19806 | 0.687285 | 0 |
| b-NGF_1 | 1.018717 | 1.22647 | 0.948845 | 0 |
| TGF-b3_1 | 1.000846 | 1.16675 | 0.948845 | 3 |
| IGF-1 SR | 2.154497 | 2.01788 | 0.102881 | 5 |
| GRO_1 | 1.12464 | 1.34176 | 0.687285 | 5 |
| FGF-9_1 | 0.908764 | 1.34736 | 1.257862 | 5 |
| GITR-Light | 0.891591 | 1.23962 | 1.323988 | 5 |
| IL-8_1 | 4.611751 | 2.30142 | 0.102881 | 6 |
| IL-12 p40__ | 4.397923 | 2.30237 | 0.102881 | 6 |
| IL-11_1 | 3.428231 | 3.16541 | 0.102881 | 6 |
| Lymphotac | 2.655294 | 1.92588 | 0.102881 | 6 |
| IL-1 RI_1 | 2.299796 | 2.69797 | 0.102881 | 6 |
| CTACK_1 | 2.166969 | 1.4123 | 0.102881 | 6 |
| HGF_1 | 1.917834 | 2.11589 | 0.102881 | 6 |
| I-TAC_1 | 1.761741 | 1.75813 | 0.102881 | 6 |
| ICAM-3_1 | 1.647733 | 1.63994 | 0.102881 | 6 |
| IL-2 Ra_1 | 1.517361 | 1.75028 | 0.290698 | 6 |
| DTK_1 | 1.334052 | 1.36685 | 0.362319 | 6 |
| IL-12 p70__ | 1.136177 | 1.52347 | 0.687285 | 6 |

TABLE 9A2

| Name | Score (d) | Fold Change | q-value (%) | Cluster |
|---|---|---|---|---|
| IL-17_1 | 0.973182 | 1.5033 | 0.948845 | 6 |
| ANG-2_1 | 2.573094 | 1.48217 | 0.102881 | 8 |
| IGFBP-6_1 | 2.559164 | 1.49096 | 0.102881 | 8 |
| IL-6 R_1 | 2.308765 | 1.42281 | 0.102881 | 8 |
| IGFBP-1_1 | 1.641212 | 1.3909 | 0.102881 | 8 |
| AR_1 | 1.388841 | 1.31995 | 0.362319 | 8 |
| IGFBP-2_1 | 1.313148 | 1.18336 | 0.362319 | 8 |
| HCC-4_1 | 1.301826 | 1.48316 | 0.362319 | 8 |
| IL-1R4/ST | 0.973381 | 1.28961 | 0.948845 | 8 |

TABLE 9B

| Name | Score (d) | Fold Change | q-value (%) | Cluster |
|---|---|---|---|---|
| SDF-1_1 | −3.717529 | 0.51302 | 0.102881 | 1 |
| TNF-a_1 | −3.502517 | 0.52906 | 0.102881 | 1 |
| TARC_1 | −2.327413 | 0.47705 | 0.102881 | 1 |
| TNF-b_1 | −1.156171 | 0.86239 | 1.121795 | 1 |
| MCP-2_1 | −5.829911 | 0.25732 | 0.102881 | 2 |
| M-CSF_1 | −5.008296 | 0.42889 | 0.102881 | 2 |
| IL-1a_1 | −4.92065 | 0.29231 | 0.102881 | 2 |
| MDC_1 | −4.362592 | 0.48973 | 0.102881 | 2 |
| MCP-3_1 | −4.034665 | 0.36994 | 0.102881 | 2 |
| BLC_1 | −3.624823 | 0.54297 | 0.102881 | 2 |
| MCP-4_1 | −3.391387 | 0.33264 | 0.102881 | 2 |
| Eotaxin-3__ | −3.378874 | 0.50745 | 0.102881 | 2 |
| IL-3_1 | −3.292671 | 0.45124 | 0.102881 | 2 |
| IL-1b_1 | −3.2351 | 0.33216 | 0.102881 | 2 |
| IL-16_1 | −3.112419 | 0.26418 | 0.102881 | 2 |
| IL-2_1 | −3.091275 | 0.39923 | 0.102881 | 2 |
| FGF-6_1 | −2.995265 | 0.60629 | 0.102881 | 2 |
| IL-15_1 | −2.990886 | 0.2798 | 0.102881 | 2 |
| IL-4_1 | −2.909983 | 0.56937 | 0.102881 | 2 |
| GDNF_1 | −2.898614 | 0.57687 | 0.102881 | 2 |
| I-309_1 | −2.813435 | 0.58059 | 0.102881 | 2 |
| MCP-1_1 | −2.807517 | 0.60158 | 0.102881 | 2 |
| IL-5_1 | −2.533339 | 0.11191 | 0.102881 | 2 |
| IGF-1_1 | −2.429866 | 0.60042 | 0.102881 | 2 |
| LIGHT_1 | −1.739557 | 0.68069 | 0.102881 | 2 |
| GCP-2_1 | −1.69179 | 0.3493 | 0.102881 | 2 |
| Fractalkine | −1.687498 | 0.59612 | 0.102881 | 2 |
| IL-1ra_1 | −1.589684 | 0.78477 | 0.200803 | 2 |
| Flt-3 Ligand | −1.113565 | 0.67551 | 1.190476 | 2 |
| IFN-g_1 | −3.560171 | 0.58458 | 0.102881 | 3 |
| MIP-1d_1 | −3.163485 | 0.71538 | 0.102881 | 3 |
| IL-6_1 | −2.794102 | 0.48921 | 0.102881 | 3 |
| CK b8-1_1 | −2.589929 | 0.68946 | 0.102881 | 3 |
| BMP-6_1 | −2.434357 | 0.72473 | 0.102881 | 3 |
| Eotaxin-2__ | −2.356828 | 0.7222 | 0.102881 | 3 |
| CNTF_1 | −2.309291 | 0.75875 | 0.102881 | 3 |
| MIP-3a_1 | −2.029226 | 0.70276 | 0.102881 | 3 |
| MIG_1 | −1.894224 | 0.72898 | 0.102881 | 3 |
| TGF-b_1 | −1.782306 | 0.70401 | 0.102881 | 3 |
| BMP-4_1 | −0.922924 | 0.92324 | 1.697531 | 3 |
| IGFBP-4_1 | −2.630045 | 0.5017 | 0.102881 | 4 |
| IL-7_1 | −0.692426 | 0.40835 | 2.19697 | 4 |
| PDGF-BB__ | −1.153073 | 0.79665 | 1.121795 | 5 |
| GM-CSF_1 | −3.318119 | 0.16273 | 0.102881 | 7 |
| SCF_1 | −2.478851 | 0.6653 | 0.102881 | 7 |
| IL-10_1 | −1.864524 | 0.3965 | 0.102881 | 7 |
| IL-13_1 | −1.538539 | NA | 0.200803 | 7 |
| GRO-a_1 | −1.338516 | 0.47248 | 0.531915 | 7 |
| FGF-7_1 | −1.147464 | 0.55216 | 1.121795 | 7 |
| BDNF_1 | −0.877883 | 0.9095 | 1.75841 | 7 |

TABLE 10A1

| Name | Score (d) | Fold Change | q-value (%) |
|---|---|---|---|
| NAP-2_1 | 3.015803 | 2.3311 | 0.416666667 |
| ANG_1 | 2.7793114 | 2.0092 | 0.416666667 |
| PARC_1 | 2.7552638 | 2.63872 | 0.416666667 |
| ICAM-1_1 | 2.5183244 | 2.54462 | 0.416666667 |

TABLE 10A1-continued

| Name | Score (d) | Fold Change | q-value (%) |
|---|---|---|---|
| IL-6 R_1 | 2.1634336 | 2.07358 | 0.416666667 |
| BTC_1 | 2.1006544 | 2.19149 | 0.416666667 |
| Acrp30_1 | 2.0335818 | 3.65294 | 0.416666667 |
| MSP-a_1 | 2.0025957 | 2.39185 | 0.416666667 |
| sTNF RII_1 | 1.9686306 | 2.15344 | 0.416666667 |
| TIMP-2_1 | 1.871601 | 1.99706 | 0.416666667 |
| TRAIL R3_1 | 1.833582 | 2.20251 | 0.416666667 |
| ANG-2_1 | 1.7806394 | 2.07536 | 0.416666667 |
| IL-8_1 | 1.7332094 | 2.02022 | 0.416666667 |
| AXL_1 | 1.6501027 | 1.883 | 0.416666667 |
| MIF_1 | 1.6434624 | 2.22659 | 0.416666667 |
| TIMP-1_1 | 1.5836883 | 1.7417 | 0.416666667 |
| MIP-1b_1 | 1.5753303 | 2.36633 | 0.416666667 |
| IGFBP-6_1 | 1.4684802 | 1.92629 | 0.416666667 |
| spg130_1 | 1.391691 | 2.1923 | 0.416666667 |
| CTACK_1 | 1.3483897 | 1.72505 | 0.416666667 |
| IGFBP3_1 | 1.3384955 | 1.84934 | 0.416666667 |
| uPAR_1 | 1.3349356 | 2.42069 | 0.416666667 |
| MIP-1a_1 | 1.3186579 | 1.931 | 0.416666667 |
| TRAIL R4_1 | 1.3116694 | 1.98605 | 0.416666667 |
| IL-12 p40_1 | 1.2911168 | 1.63912 | 0.416666667 |
| AR_1 | 1.2206417 | 2.15904 | 0.416666667 |
| TPO_1 | 1.2044047 | 1.86455 | 0.416666667 |
| NT-4_1 | 1.1793811 | 2.41703 | 0.416666667 |
| FAS_1 | 1.169934 | 1.59942 | 0.416666667 |
| bFGF | 1.1482616 | 1.58016 | 0.416666667 |
| VEGF-B_1 | 1.1358842 | 1.89024 | 0.416666667 |
| VEGF-D_1 | 1.0974084 | 3.07633 | 0.416666667 |
| OSM_1 | 1.0240581 | 1.8449 | 0.416666667 |
| OST_1 | 0.9845184 | 1.82276 | 0.416666667 |
| IL-11_1 | 0.9675503 | 2.26315 | 0.416666667 |
| sTNF RI_1 | 0.9627974 | 1.96913 | 0.416666667 |
| RANTES_1 | 0.9456799 | 1.34024 | 0.416666667 |
| I-TAC_1 | 0.9164841 | 2.27116 | 0.416666667 |
| Eotaxin_1 | 0.8908395 | 1.46174 | 1.215277778 |
| TECK_1 | 0.8828589 | 1.77056 | 1.215277778 |
| PlGF_1 | 0.8283546 | 2.16487 | 1.215277778 |
| b-NGF_1 | 0.8160618 | 1.60576 | 1.215277778 |
| EGF-R_1 | 0.7960517 | 1.41315 | 1.215277778 |
| Lymphotactin_1 | 0.7585063 | 1.55228 | 1.215277778 |
| MIP-3b_1 | 0.7025106 | 1.81688 | 2.5 |
| HCC-4_1 | 0.6557043 | 1.70769 | 2.5 |
| ICAM-3_1 | 0.6370118 | 1.72939 | 3.012048193 |
| IGFBP-2_1 | 0.6208166 | 1.2029 | 3.012048193 |
| DTK_1 | 0.5615526 | 1.50254 | 3.63372093 |
| IL-1 RI_1 | 0.5347156 | 1.73834 | 3.93258427 |
| IGF-1 SR | 0.5135245 | 1.5253 | 3.93258427 |

TABLE 10A2

| Name | Score (d) | Fold Change | q-value (%) |
|---|---|---|---|
| AgRP(ART)_1 | 0.5124192 | 1.82258 | 3.93258427 |
| GRO_1 | 0.4666771 | 1.31521 | 5.163043478 |
| GITR-Light_1 | 0.4504103 | 1.38962 | 5.859375 |
| IGFBP-1_1 | 0.4352987 | 1.20224 | 5.859375 |
| HGF_1 | 0.4038156 | 1.33883 | 6.18556701 |
| IL-1R4/ST | 0.2875716 | 1.22954 | 9.926470588 |
| IL-2 Ra_1 | 0.25742 | 1.2669 | 10.71428571 |
| ENA-78_1 | 0.2468783 | 1.29573 | 10.71428571 |
| FGF-9_1 | 0.2420414 | 1.23628 | 10.71428571 |

TABLE 10B

| Gene Name | Score (d) | Fold Change | q-value (%) |
|---|---|---|---|
| MCP-2_1 | −2.304292 | 0.22807 | 0.416666667 |
| IL-1ra_1 | −2.207305 | 0.55921 | 0.416666667 |
| M-CSF_1 | −2.0793884 | 0.38905 | 0.416666667 |
| MCP-1_1 | −2.0252914 | 0.4534 | 0.416666667 |
| IL-3_1 | −1.9497211 | 0.33125 | 0.416666667 |

TABLE 10B-continued

| Gene Name | Score (d) | Fold Change | q-value (%) |
|---|---|---|---|
| MCP-3_1 | −1.8900971 | 0.29936 | 0.416666667 |
| MDC_1 | −1.7837426 | 0.44485 | 0.416666667 |
| MCP-4_1 | −1.7161914 | 0.24506 | 0.416666667 |
| IL-1b_1 | −1.7090727 | 0.25335 | 0.416666667 |
| BMP-6_1 | −1.601608 | 0.60317 | 0.416666667 |
| IL-4_1 | −1.5566673 | 0.46009 | 0.416666667 |
| IL-1a_1 | −1.5383795 | 0.31159 | 0.416666667 |
| BLC_1 | −1.5068668 | 0.48287 | 0.416666667 |
| CNTF_1 | −1.4946707 | 0.6341 | 0.416666667 |
| CK b8-1_1 | −1.4772423 | 0.56519 | 0.416666667 |
| IL-2_1 | −1.4647542 | 0.30616 | 0.416666667 |
| IFN-g_1 | −1.3743866 | 0.55449 | 0.416666667 |
| IL-15_1 | −1.2793787 | 0.22092 | 0.416666667 |
| Eotaxin-2_1 | −1.2356313 | 0.64369 | 0.416666667 |
| MIP-3a_1 | −1.2249652 | 0.56046 | 0.416666667 |
| MIG_1 | −1.169439 | 0.59839 | 0.416666667 |
| SCF_1 | −1.0907746 | 0.62327 | 0.416666667 |
| IL-6_1 | −1.0435505 | 0.43341 | 1.215277778 |
| PDGF-BB_1 | −1.0262008 | 0.68948 | 1.215277778 |
| IL-16_1 | −0.9969314 | 0.23613 | 1.215277778 |
| Eotaxin-3_1 | −0.9674019 | 0.52064 | 1.215277778 |
| I-309_1 | −0.941786 | 0.54744 | 1.215277778 |
| TGF-b_1 | −0.9411308 | 0.59424 | 1.215277778 |
| TNF-a_1 | −0.9018304 | 0.58157 | 1.623376623 |
| FGF-6_1 | −0.897254 | 0.63694 | 1.623376623 |
| GDNF_1 | −0.8697946 | 0.60042 | 1.623376623 |
| MIP-1d_1 | −0.8577233 | 0.77094 | 1.623376623 |
| LIGHT_1 | −0.8539608 | 0.606 | 1.623376623 |
| SDF-1_1 | −0.807095 | 0.60929 | 2.5 |
| IGF-1_1 | −0.7466459 | 0.61547 | 3.012048193 |
| Fractalkine_1 | −0.7310159 | 0.51894 | 3.63372093 |
| BDNF_1 | −0.7223848 | 0.82491 | 3.63372093 |
| IL-5_1 | −0.6300046 | 0.12006 | 4.532967033 |
| TGF-b3_1 | −0.6228815 | 0.8205 | 4.532967033 |
| BMP-4_1 | −0.5789929 | 0.87844 | 5.319148936 |
| Flt-3 Ligand_1 | −0.5692741 | 0.55604 | 5.319148936 |
| GM-CSF_1 | −0.5288316 | 0.25808 | 6.565656566 |
| IGFBP-4_1 | −0.5086457 | 0.69375 | 6.565656566 |
| GCP-2_1 | −0.4309765 | 0.37597 | 7.5 |
| TARC_1 | −0.4088338 | 0.59042 | 7.673267327 |

TABLE 11A1

| Name | Score (d) | Fold Change | q-value (%) |
|---|---|---|---|
| TRAIL R4_1 | 2.264750916 | NA | 0.904761905 |
| Eotaxin_1 | 1.93445339 | 4.70062 | 0.904761905 |
| IL-12 p40_1 | 1.880163267 | 3.86536 | 0.904761905 |
| BTC_1 | 1.792904474 | 2.4468 | 0.904761905 |
| IL-8_1 | 1.623999996 | 2.67095 | 0.904761905 |
| MIF_1 | 1.578135137 | 2.79532 | 0.904761905 |
| MSP-a_1 | 1.541907487 | 2.11334 | 0.904761905 |
| uPAR_1 | 1.392662122 | 4.38083 | 0.904761905 |
| OST_1 | 1.357147945 | 6.61147 | 0.904761905 |
| MIP-1a_1 | 1.131822882 | 2.18476 | 0.904761905 |
| TPO_1 | 1.127049496 | 2.28982 | 0.904761905 |
| TRAIL R3_1 | 1.092119228 | 1.61261 | 0.904761905 |
| TGF-b3_1 | 1.043970414 | 1.99067 | 0.904761905 |
| sTNF RII_1 | 1.033890515 | 1.55451 | 0.904761905 |
| GCSF_1 | 1.024951701 | 3.10372 | 0.904761905 |
| sTNF RI_1 | 1.014653009 | 2.78772 | 0.904761905 |
| IL-11_1 | 1.00391809 | 5.07851 | 0.904761905 |
| MIP-1b_1 | 0.9966162 | 1.83838 | 0.904761905 |
| VEGF-B_1 | 0.94194004 | 2.00884 | 0.904761905 |
| Lymphotactin_1 | 0.935601365 | 2.41527 | 0.904761905 |
| NT-4_1 | 0.923994255 | 2.57292 | 0.904761905 |
| VEGF-D_1 | 0.898048249 | 3.15089 | 0.904761905 |
| Acrp30_1 | 0.885692332 | 1.51332 | 0.904761905 |
| HGF_1 | 0.84992308 | 4.96263 | 0.904761905 |
| IGFBP3_1 | 0.792485456 | 1.54086 | 0.904761905 |
| IGFBP-1_1 | 0.784580171 | 1.62237 | 0.904761905 |
| OSM_1 | 0.748360453 | 1.76423 | 0.904761905 |
| IL-1 RI_1 | 0.744755448 | 6.0184 | 0.904761905 |

TABLE 11A1-continued

| Name | Score (d) | Fold Change | q-value (%) |
|---|---|---|---|
| PIGF_1 | 0.723608877 | 2.81402 | 1.544715447 |
| IGF-1 SR | 0.708495305 | 3.05733 | 1.544715447 |
| RANTES | 0.701613901 | 1.26004 | 1.544715447 |
| ICAM-1_1 | 0.644564318 | 1.24206 | 2.753623188 |
| CCL-28_1 | 0.587722077 | 5.65125 | 3.298611111 |
| IL-1ra_1 | 0.555953031 | 1.3324 | 5.61827957 |
| IL-2 Ra_1 | 0.551415381 | 2.80849 | 5.61827957 |
| PARC_1 | 0.518735944 | 1.15104 | 5.61827957 |
| FAS_1 | 0.507008801 | 1.28116 | 5.61827957 |
| IL-12 p70_1 | 0.487911594 | 3.29805 | 5.61827957 |
| NAP-2_1 | 0.484247072 | 1.11825 | 5.61827957 |
| GRO_1 | 0.461543045 | 1.44588 | 5.61827957 |
| NT-3_1 | 0.410047836 | 1.32477 | 7.6 |
| IGFBP-6_1 | 0.408420436 | 1.21894 | 7.6 |
| TIMP-1_1 | 0.400113082 | 1.14706 | 7.6 |
| IL-17_1 | 0.392498707 | 2.73288 | 7.6 |
| IGFBP-2_1 | 0.38618776 | 1.16272 | 7.6 |
| CTACK_1 | 0.380915566 | 1.19299 | 7.6 |
| I-TAC_1 | 0.370637104 | 1.4308 | 7.6 |
| ICAM-3_1 | 0.338506181 | 1.47039 | 8.417721519 |
| ANG-2_1 | 0.335369663 | 1.14941 | 8.417721519 |
| FGF-4_1 | 0.311494132 | 1.91614 | 9.104166667 |
| MIP-3b_1 | 0.293878941 | 1.34124 | 9.728915663 |

TABLE 11A2

| Name | Score (d) | Fold Change | q-value (%) |
|---|---|---|---|
| FGF-9_1 | 0.293742777 | 1.46816 | 9.728915663 |
| HCC-4_1 | 0.263286334 | 1.29481 | 11.61111111 |
| IL-1R4/ST | 0.252559948 | 1.32988 | 11.61111111 |
| ANG_1 | 0.248721281 | 1.05528 | 11.61111111 |
| GITR_1 | 0.247865761 | 1.33642 | 11.61111111 |
| DTK_1 | 0.241137412 | 1.25033 | 11.61111111 |
| IL-6 R_1 | 0.225218631 | 1.072 | 12.04710145 |
| EGF-R_1 | 0.193331739 | 1.1082 | 13.81205674 |

TABLE 11B

| Name | Score (d) | Fold Change | q-value (%) |
|---|---|---|---|
| IL-1a_1 | −1.425685763 | 0.28059 | 0.904761905 |
| MCP-2_1 | −1.212675578 | 0.30691 | 0.904761905 |
| IGFBP-4_1 | −1.20895142 | 0.39001 | 0.904761905 |
| spg130_1 | −1.199429488 | 0.61096 | 0.904761905 |
| SDF-1_1 | −1.153623548 | 0.44789 | 0.904761905 |
| M-CSF_1 | −1.111197881 | 0.48295 | 0.904761905 |
| MIP-1d_1 | −1.070072417 | 0.65762 | 0.904761905 |
| IL-10_1 | −1.009846401 | 0.25518 | 1.544715447 |
| GM-CSF_1 | −0.958718459 | 0.11603 | 1.544715447 |
| TNF-a_1 | −0.934948264 | 0.49119 | 1.544715447 |
| MDC_1 | −0.869780931 | 0.55252 | 2.753623188 |
| FGF-6_1 | −0.846319232 | 0.58971 | 2.753623188 |
| TNF-b_1 | −0.842647499 | 0.72752 | 2.753623188 |
| IFN-g_1 | −0.831081042 | 0.60989 | 2.753623188 |
| GDNF_1 | −0.790743331 | 0.55062 | 3.298611111 |
| Eotaxin-3_1 | −0.7492123 | 0.51758 | 5.61827957 |
| MCP-3_1 | −0.643949943 | 0.49699 | 5.61827957 |
| BLC_1 | −0.635584231 | 0.621 | 5.61827957 |
| IGF-1_1 | −0.626811933 | 0.59071 | 5.61827957 |
| TARC_1 | −0.621812924 | 0.407 | 5.61827957 |
| IL-13_1 | −0.606932031 | NA | 5.61827957 |
| AXL_1 | −0.602711809 | 0.80618 | 5.61827957 |
| GRO-a_1 | −0.535561363 | 0.42506 | 5.61827957 |
| IL-1b_1 | −0.527429339 | 0.48739 | 7.6 |
| SCF_1 | −0.523648284 | 0.72671 | 7.6 |
| IL-5_1 | −0.523276967 | 0.10826 | 7.6 |
| IL-16_1 | −0.519147838 | 0.30682 | 7.6 |

TABLE 11B-continued

| Name | Score (d) | Fold Change | q-value (%) |
|---|---|---|---|
| I-309_1 | −0.512084847 | 0.61731 | 7.6 |
| TECK_1 | −0.483535641 | 0.76083 | 8.417721519 |
| AgRP(ART)_1 | −0.472803161 | 0.6455 | 8.417721519 |
| IL-6_1 | −0.44191818 | 0.57236 | 9.728915663 |
| IL-15_1 | −0.41494314 | 0.38371 | 11.61111111 |
| GCP-2_1 | −0.401329611 | 0.31787 | 11.61111111 |
| MCP-4_1 | −0.392420281 | 0.52574 | 12.04710145 |
| Eotaxin-2_1 | −0.354478448 | 0.82923 | 13.81205674 |
| IL-2_1 | −0.343716173 | 0.58707 | 13.85416667 |
| IL-4_1 | −0.334158663 | 0.74801 | 13.85416667 |
| FGF-7_1 | −0.31567674 | 0.48289 | 14.21768707 |
| LIGHT_1 | −0.307045767 | 0.77313 | 14.21768707 |
| IL-3_1 | −0.288230929 | 0.71595 | 14.39393939 |
| Fractalkine_1 | −0.255510085 | 0.69456 | 16.77392739 |
| IL-7_1 | −0.212551274 | 0.37996 | 16.77392739 |
| CK b8-1_1 | −0.171953761 | 0.89232 | 18.0952381 |
| BMP-6_1 | −0.165427865 | 0.918 | 18.0952381 |
| LEPTIN(OB)_1 | −0.162080603 | 0.88435 | 18.0952381 |
| MCP-1_1 | −0.157017681 | 0.8931 | 18.0952381 |

TABLE 12A

| Name | Score (d) | Fold Change | q-value (%) |
|---|---|---|---|
| NAP-2_1 | 4.267334 | 2.25145 | 0.694444 |
| ANG_1 | 4.061566 | 1.97693 | 0.694444 |
| AXL_1 | 3.946682 | 2.03097 | 0.694444 |
| PARC_1 | 3.740647 | 2.53113 | 0.694444 |
| ICAM-1_1 | 3.510347 | 2.38945 | 0.694444 |
| IL-6 R_1 | 3.397778 | 2.02276 | 0.694444 |
| spg130_1 | 3.297869 | 2.61126 | 0.694444 |
| ANG-2_1 | 3.253421 | 1.98738 | 0.694444 |
| AR_1 | 2.780729 | 2.195 | 0.694444 |
| IGFBP-6_1 | 2.766085 | 1.81674 | 0.694444 |
| TIMP-2_1 | 2.746738 | 1.96642 | 0.694444 |
| sTNF RII__ | 2.70119 | 1.9052 | 0.694444 |
| BTC_1 | 2.354153 | 1.77895 | 0.694444 |
| Acrp30_1 | 2.292376 | 3.26933 | 0.694444 |
| CTACK_1 | 2.286645 | 1.63476 | 0.694444 |
| bFGF | 2.254793 | 1.59862 | 0.694444 |
| TIMP-1_1 | 2.203826 | 1.67415 | 0.694444 |
| TRAIL R3__ | 2.143125 | 1.93754 | 0.694444 |
| MSP-a_1 | 2.110976 | 1.99091 | 0.694444 |
| MIP-1b_1 | 2.086051 | 2.01983 | 0.694444 |
| FAS_1 | 2.059914 | 1.48374 | 0.694444 |
| IGFBP3_1 | 1.955992 | 1.63927 | 1.092896 |
| TECK_1 | 1.799893 | 1.93772 | 1.092896 |
| IL-8_1 | 1.798862 | 1.61555 | 1.092896 |
| b-NGF_1 | 1.772438 | 1.60984 | 1.092896 |
| MIF_1 | 1.695812 | 1.77156 | 1.092896 |
| MIP-1a_1 | 1.679684 | 1.59738 | 1.092896 |
| NT-4_1 | 1.61208 | 1.94614 | 1.092896 |
| EGF-R_1 | 1.607028 | 1.36793 | 1.092896 |
| I-TAC_1 | 1.557412 | 2.05114 | 3.196347 |
| OSM_1 | 1.48 | 1.59379 | 3.196347 |
| TPO_1 | 1.401631 | 1.53133 | 3.196347 |
| VEGF-B_1 | 1.386749 | 1.58684 | 3.196347 |
| VEGF-D_1 | 1.343569 | 2.40993 | 3.196347 |
| uPAR_1 | 1.32707 | 1.82461 | 3.196347 |
| MIP-3b_1 | 1.264924 | 1.66183 | 3.196347 |
| AgRP(ART | 1.184203 | 2.12294 | 4.819277 |
| PIGF_1 | 1.121384 | 1.71402 | 4.819277 |

TABLE 12A-continued

| Name | Score (d) | Fold Change | q-value (%) |
|---|---|---|---|
| HCC-4_1 | 1.115816 | 1.57811 | 4.819277 |
| IL-11_1 | 1.111969 | 1.67652 | 4.819277 |
| DTK_1 | 1.089757 | 1.40526 | 4.819277 |
| sTNF RI_1 | 1.083266 | 1.57406 | 4.819277 |
| TNF-b_1 | 1.064988 | 1.18835 | 4.819277 |
| ICAM-3_1 | 1.047944 | 1.5309 | 4.819277 |
| RANTES__ | 1.039346 | 1.25415 | 4.819277 |

TABLE 12B

| Name | Score (d) | Fold Change | q-value (%) |
|---|---|---|---|
| IL-1ra_1 | −5.041602 | 0.51632 | 0.694444 |
| IL-3_1 | −4.65699 | 0.37506 | 0.694444 |
| MCP-1_1 | −4.613776 | 0.47067 | 0.694444 |
| MCP-4_1 | −4.073299 | 0.31815 | 0.694444 |
| MCP-3_1 | −3.883939 | 0.40145 | 0.694444 |
| MCP-2_1 | −3.794381 | 0.40233 | 0.694444 |
| CK b8-1_1 | −3.694038 | 0.58898 | 0.694444 |
| CNTF_1 | −3.611565 | 0.64605 | 0.694444 |
| IL-1b_1 | −3.539065 | 0.34043 | 0.694444 |
| BMP-6_1 | −3.532174 | 0.62281 | 0.694444 |
| IL-2_1 | −3.525665 | 0.37899 | 0.694444 |
| IL-4_1 | −3.512443 | 0.51003 | 0.694444 |
| M-CSF_1 | −3.435204 | 0.5251 | 0.694444 |
| MIP-3a_1 | −3.223006 | 0.57152 | 0.694444 |
| MDC_1 | −3.136714 | 0.56385 | 0.694444 |
| BLC_1 | −2.977992 | 0.57752 | 0.694444 |
| MIG_1 | −2.84823 | 0.61226 | 0.694444 |
| IL-15_1 | −2.83153 | 0.33554 | 0.694444 |
| Eotaxin-2__ | −2.466855 | 0.68813 | 0.694444 |
| IFN-g_1 | −2.339649 | 0.66411 | 0.694444 |
| TGF-b3_1 | −2.302077 | 0.68801 | 0.694444 |
| TGF-b_1 | −2.237739 | 0.6243 | 0.694444 |
| IL-6_1 | −2.232468 | 0.54172 | 0.694444 |
| IL-16_1 | −2.116464 | 0.41262 | 0.694444 |
| IL-1a_1 | −1.926189 | 0.57411 | 0.694444 |
| I-309_1 | −1.895322 | 0.65572 | 0.694444 |
| SCF_1 | −1.888043 | 0.70339 | 0.694444 |
| LIGHT_1 | −1.703026 | 0.66186 | 1.092896 |
| PDGF-BB__ | −1.661166 | 0.70275 | 1.092896 |
| BDNF_1 | −1.610622 | 0.82141 | 1.092896 |
| Fractalkine | −1.601759 | 0.59002 | 1.092896 |
| Eotaxin-3__ | −1.528746 | 0.69067 | 1.092896 |
| Flt-3 Ligand | −1.421242 | 0.58491 | 3.196347 |
| GCSF_1 | −1.236217 | 0.70092 | 3.196347 |
| GDNF_1 | −1.233345 | 0.75441 | 3.196347 |
| BMP-4_1 | −1.194332 | 0.88628 | 3.196347 |
| FGF-6_1 | −1.183592 | 0.78548 | 3.196347 |
| IGF-1_1 | −1.132697 | 0.75456 | 4.819277 |
| IL-5_1 | −1.102411 | 0.44825 | 5.098039 |
| TNF-a_1 | −1.087972 | 0.779 | 5.098039 |

TABLE 13A

| Protein Name | Score (d) | Fold Change | p-value (%) |
|---|---|---|---|
| BTC_1 | 5.280599 | 2.30404 | 0.106838 |
| IL-8_1 | 4.611751 | 2.30142 | 0.106838 |
| IL-12 p40_1 | 4.397923 | 2.30237 | 0.106838 |
| TRAIL R4_1 | 4.18957 | 4.38847 | 0.106838 |
| MIF_1 | 3.78626 | 2.46763 | 0.106838 |
| MIP-1a_1 | 3.671968 | 2.04509 | 0.106838 |
| sTNF RII_1 | 3.57664 | 1.81136 | 0.106838 |
| MSP-a_1 | 3.532718 | 2.23649 | 0.106838 |
| OST_1 | 3.519536 | 2.85493 | 0.106838 |

TABLE 13A-continued

| Protein Name | Score (d) | Fold Change | p-value (%) |
|---|---|---|---|
| IL-11_1 | 3.428231 | 3.16541 | 0.106838 |
| uPAR_1 | 3.42578 | 3.10753 | 0.106838 |
| TPO_1 | 3.260328 | 2.04533 | 0.106838 |
| NT-4_1 | 3.182778 | 2.48474 | 0.106838 |
| MIP-1b_1 | 3.119065 | 2.07252 | 0.106838 |
| NAP-2_1 | 2.970365 | 1.51262 | 0.106838 |
| ICAM-1_1 | 2.949073 | 1.6633 | 0.106838 |
| IGFBP3_1 | 2.868921 | 1.68668 | 0.106838 |
| TRAIL R3_1 | 2.808197 | 1.85516 | 0.106838 |
| Eotaxin_1 | 2.747874 | 2.23776 | 0.106838 |
| VEGF-B_1 | 2.73066 | 1.94657 | 0.106838 |

TABLE 13A-continued

| Protein Name | Score (d) | Fold Change | p-value (%) |
|---|---|---|---|
| PARC_1 | 2.703205 | 1.59801 | 0.106838 |
| Lymphotactin_1 | 2.655294 | 1.92588 | 0.106838 |
| sTNF RI_1 | 2.628389 | 2.27051 | 0.106838 |
| PIGF_1 | 2.59266 | 2.46572 | 0.106838 |
| ANG-2_1 | 2.573094 | 1.48217 | 0.106838 |
| IGFBP-6_1 | 2.559164 | 1.49096 | 0.106838 |
| OSM_1 | 2.548107 | 1.79103 | 0.106838 |
| ANG_1 | 2.527071 | 1.38167 | 0.106838 |
| FAS_1 | 2.522175 | 1.42939 | 0.106838 |

TABLE 13B

| Name | Score (d) | Fold Change | p-value (%) |
|---|---|---|---|
| MCP-2_1 | −5.82991 | 0.25732 | 0.106838 |
| M-CSF_1 | −5.0083 | 0.42889 | 0.106838 |
| IL-1a_1 | −4.92065 | 0.29231 | 0.106838 |
| MDC_1 | −4.36259 | 0.48973 | 0.106838 |
| MCP-3_1 | −4.03467 | 0.36994 | 0.106838 |
| SDF-1_1 | −3.71753 | 0.51302 | 0.106838 |
| BLC_1 | −3.62482 | 0.54297 | 0.106838 |
| IFN-g_1 | −3.56017 | 0.58458 | 0.106838 |
| TNF-a_1 | −3.50252 | 0.52906 | 0.106838 |
| MCP-4_1 | −3.39139 | 0.33264 | 0.106838 |
| Eotaxin-3_1 | −3.37887 | 0.50745 | 0.106838 |
| GM-CSF_1 | −3.31812 | 0.16273 | 0.106838 |
| IL-3_1 | −3.29267 | 0.45124 | 0.106838 |
| IL-1b_1 | −3.2351 | 0.33216 | 0.106838 |
| MIP-1d_1 | −3.16349 | 0.71538 | 0.106838 |
| IL-16_1 | −3.11242 | 0.26418 | 0.106838 |
| IL-2_1 | −3.09127 | 0.39923 | 0.106838 |
| FGF-6_1 | −2.99526 | 0.60629 | 0.106838 |
| IL-15_1 | −2.99089 | 0.2798 | 0.106838 |
| IL-4_1 | −2.90998 | 0.56937 | 0.106838 |
| GDNF_1 | −2.89861 | 0.57687 | 0.106838 |
| I-309_1 | −2.81343 | 0.58059 | 0.106838 |
| MCP-1_1 | −2.80752 | 0.60158 | 0.106838 |
| IL-6_1 | −2.7941 | 0.48921 | 0.106838 |

Example 14

Example 14 discloses the identification of biomarkers found to significantly correlate with MMSE scores (from 8 to 28) of AD subjects as shown below in Table 14. Therefore, Lymphotactin and IL-11 are useful for detection of early to mild AD and for the staging and progression of the disease. Lymphotactin and/or IL-11 can be used alone or together with other AD biomarkers, including those described herein in the methods disclosed herein. Accordingly, provided herein are methods for stratifying AD as well as monitoring the progress of AD that comprise comparing a measured level of Lymphotactin and/or IL-11 in a biological fluid sample, such as plasma, from an individual to a reference level for the biomarker.

TABLE 14

| | Correlation Coefficient Hypothesized Correlation = 0 | | | | | |
|---|---|---|---|---|---|---|
| | Correlation | Count | Z-Value | P-Value | 95% Lower | 95% Upper |
| MMSE, IL-11_1 | .529 | 35 | 3.329 | .0009 | .237 | .733 |
| MMSE, Lymphotactin_1 | .516 | 35 | 3.226 | .0013 | .220 | .724 |
| IL-11_1, Lymphotactin_1 | .488 | 35 | 3.015 | .0026 | .184 | .706 |

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention.

We claim:

1. A method of aiding diagnosis of Alzheimer's disease ("AD"), comprising:
   obtaining a blood sample from a human individual;
   comparing normalized measured levels of a group of at least 4 AD diagnosis biomarkers from the individual's blood sample to a reference level of each AD diagnosis biomarker;
   wherein the group of AD diagnosis biomarkers comprises BDNF, PDGF-BB, Leptin and RANTES;
   wherein the reference level of each AD diagnosis biomarker comprises a normalized measured level of the AD diagnosis biomarker from one or more blood samples of human individuals without AD; and
   wherein levels of AD diagnosis biomarkers less than the reference level of each AD diagnosis biomarker indicate a greater likelihood that the individual suffers from AD.

2. The method of claim 1, wherein a level of BDNF decreased at least 30% compared to the reference level indicates a greater likelihood that the individual suffers from AD.

3. The method of claim 1, wherein a level of PDGF-BB decreased at least 90% compared to the reference level indicates a greater likelihood that the individual suffers from AD.

4. The method of claim 1, wherein a level of Leptin decreased at least 30% compared to the reference level indicates a greater likelihood that the individual suffers from AD.

5. The method of claim 1, wherein a level of RANTES decreased at least 15% compared to the reference level indicates a greater likelihood that the individual suffers from AD.

6. The method of claim 1, wherein a level of BDNF decreased at least 30% compared to the reference level, a level of PDGF-BB decreased at least 90% compared to the reference level, a level of Leptin decreased at least 30% compared to the reference level, and a level of RANTES decreased at least 15% compared to the reference level indicates a greater likelihood that the individual suffers from AD.

* * * * *